Figure 2:
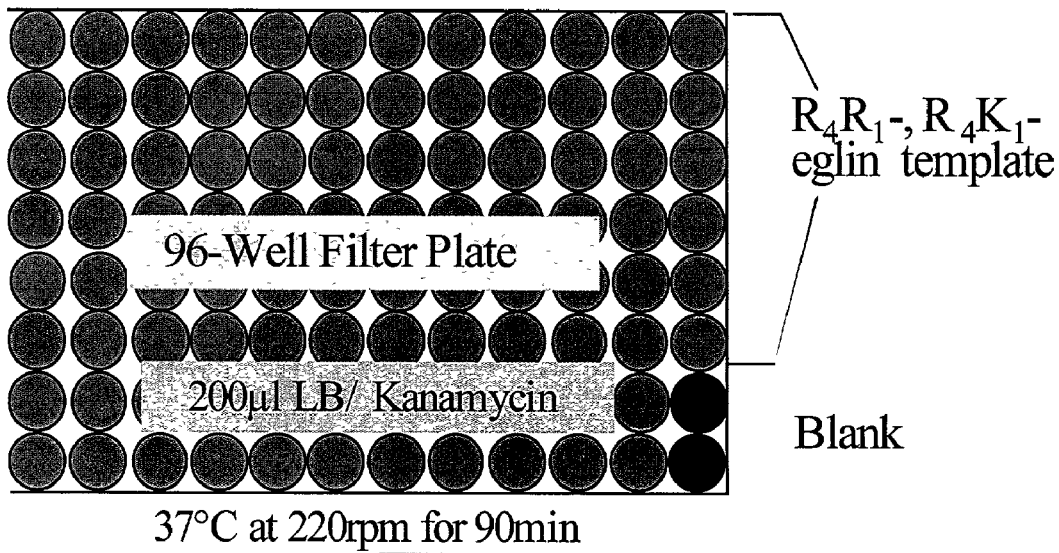

US007001884B2

(12) United States Patent
Komiyama et al.

(10) Patent No.: US 7,001,884 B2
(45) Date of Patent: Feb. 21, 2006

(54) EGLIN C BASED DRUGS FOR TREATMENT OF DISEASE

(75) Inventors: Tomoko Komiyama, Ann Arbor, MI (US); Robert S. Fuller, Ann Arbor, MI (US)

(73) Assignee: Regents of the University of Michigan, Ann Arbor, MI (US)

(*) Notice: Subject to any disclaimer, the term of this patent is extended or adjusted under 35 U.S.C. 154(b) by 429 days.

(21) Appl. No.: 10/173,524

(22) Filed: Jun. 17, 2002

(65) Prior Publication Data

US 2005/0203007 A1 Sep. 15, 2005

Related U.S. Application Data

(60) Provisional application No. 60/299,096, filed on Jun. 18, 2001.

(51) Int. Cl.
*A61K 38/00* (2006.01)

(52) U.S. Cl. ........................................................ 514/12

(58) Field of Classification Search .................. 514/12
See application file for complete search history.

(56) References Cited

U.S. PATENT DOCUMENTS

| | | | | |
|---|---|---|---|---|
| 4,636,489 | A | 1/1987 | Seemuller et al. | |
| 5,079,229 | A | 1/1992 | Grutter et al. | |
| 5,180,667 | A | 1/1993 | Grutter et al. | |
| 5,604,201 | A | 2/1997 | Thomas et al. | |
| 5,952,463 | A | 9/1999 | Shibano et al. | |
| 6,022,855 | A | 2/2000 | Thomas et al. | |
| 6,342,373 | B1 * | 1/2002 | Rink et al. | 435/69.2 |

OTHER PUBLICATIONS

Rudinger. Characteristics of the amino acids as components of a peptide hormone sequence. In Peptide Hormones. Biological Council The Co-ordinating Committee for Symposia on Drug Action. 1976. pp. A0 and 1-6.*

Dahlen, J. R. et al. (1998) J. Biol. Chem. vol. 273, pp. 1851-1854□□.*

Jean, F. et al: (1998) Proc. Natl. Acad. Sci. U.S.A. vol. 95, pp. 7293-7298.*

Lu, W. et al. (1993) J. Biol. Chem. vol. 268, pp. 14583-14585□□.*

Robertson, B. J. et al. (1993) J. Biol. Chem. 268, pp. 24274-24277□□.*

Watanabe, M. et al. (1995) J. Virology vol. 69, pp. 3206-3210□□□□.*

Volchkov, V. et al. (1998) Proc. Natl. Acad. Sci. U.S. vol. 95, pp. 5762-5767.*

Richt, J. A. et a1.. (1998) J. Virology. vol. 72, pp. 4528-4533.*

Gao, P. s et al. (1999) J. Virol. vol. 73, pp. 3184-3189.*

Molloy, S.S. et a1., (1992) J. Biol. Chem.vol. 267, pp. 16396-16402.*

Garred, 0. et al. (1995) J. Biol. Chem. vol. 270, pp. 10817-10821.*
Chiron, M. F. et al. (1994) J. Biol. Chem. vol. 269, pp. 18167-18176.*
Moehring, J.M. et al. (1993) J. Biol. Chem. vol. 268, pp. 2590-4.*

Brenner, C. and Fuller, R. S. (1992) Proc. Natl. Acad. Sci. USA vol. 89, pp. 922-926□□.*

Newport et al. (1997) Journal of Biological Chemistry. vol. 272, pp. 28954-28961.*

Tsuneoka M et al. (1993) J. Biol. Chem. vol. 268, pp. 26461-26465.*

Takahashi S et al. (1995) J. Biol. Chem. vol. 270, pp. 26565-26569□□□□.*

Jean et al. (2000) Proc. Natl. Acad. Sci. U. S. A. vol. 97, pp. 2864-2869.*

Bravo et al. (1994) J. Biol. Chem. vol. 269, pp. 25830-25837□□.*

Watanabe, M. et al. (1993) FEBS vol. 320, pp. 215-218□□.*

Krysan, D.J. et al.(1999) J. Biol. Chem. vol. 36, pp. 23229-23234□□□□.*

Zhou A et al. (1999) J. Biol. Chem. vol. 274, pp. 20745-20748□□□□□□.*

Stadler, K. et al. (1997) J. Virol. vol. 71, pp. 8475-81.*

Brenner et al. (1992) Proc Natl Acad Sci USA vol. 89, pp. 922-926.*

Inocencio et al. (1994) J Biol Chem vol. 269, pp. 31831-31835.*

Anderson et al. J Biol Chem. (1993) vol. 268, pp. 24887-24891.*

Gron, H. et al. (1992) Biochemistry. vol. 31, pp. 6011-6018.*

Laskowski, M. Jr., and Kato, 1. (1980) Ann. Rev. Biochem. vol. 49, pp. 593-626□□□□.*

(Continued)

*Primary Examiner*—Christopher R Tate
*Assistant Examiner*—Marcela M Cordero Garcia
(74) *Attorney, Agent, or Firm*—Medlen & Carroll, LLP

(57) ABSTRACT

The present invention relates to eglin c variants which inhibit proteases, and in particular to eglin c mutants at adventitious contact sites. The present invention also relates to eglin c variants which comprise mutations in both adventitious contact sites and at reactive loop sites. The present invention further relates to methods of preparing the eglin c variants, and methods of using the eglin c variants for treatment of diseases including acute bacterial, viral, and fungal infections.

10 Claims, 10 Drawing Sheets

OTHER PUBLICATIONS

Li, A., and V. Daggett, V. (1995) Protein Engineering vol. 8, pp. 1117-1128☐☐.*
Oda, K. et al. (1996) Biosci. Biotechnol. Biochem. vol. 60, pp. 1388-1389☐☐☐☐.*
Garten, W. et al. (1 994) Biochimie vol. 76, pp. 217-225☐☐☐☐☐☐.*
Braun, N. J. et al. (1987) Biol. Chem. Hoppe Seyler vol. 368, pp. 299-308.*
Moehring, J.M. et al. (1993) J. Biol. Chem. 268: 2590-4.
Chiron, M. F. et al. (1994) J. Biol. Chem. 269: 18167 18176.
Inocencio, N. M. et al. (1994) J. Biol. Chem. 269: 31831 31835.
Garred, O. et al. (1995) J. Biol. Chem. 270: 10817 21.
Molloy, S.S. et al., (1992) J. Biol. Chem. 267:16396-16402.
Gao, P. et al. (1999) J. Viol. 73: 3184 3189.
Richt, J. A. et al.. (1998) J. Viorology 72:4528 4533.
Volchkov, V. et al. (1998) Proc. Natl. Acad. Sci. U.S. 95: 5762 5767.
Watanabe, M. et al. (1995) J. Virology 69: 3206 3210.
Stadler, K. et al. (1997) J. Viol. 71: 8475 81.
Robertson, B. J. et al. (1993) J. Biol. Chem. 268: 24274 24277.
Lu, W. et al. (1993) J. Biol. Chem. 268:14583 14585.
Jean, F. et al. (1998) Proc. Natl. Acad. Sci. U.S.A. 95: 7293 7298.
Dahlen, J. R. et al. (1998) J. Biol. Chem. 273: 1851 1854).
Watanabe, M. et al. (1995) J. Virology 69: 3206 3210.
Anderson, E. D. et al. (1993) J. Biol. Chem. 268: 24887 24891.
Zhou A et al. (1999) J. Biol. Chem. 274(30): 20745 8.
Brenner, C. and Fuller, R. S. (1992) Proc. Natl. Acad. Sci. USA 89: 922 926.
Krysan, D.J. et al.(1999) J. Biol. Chem. 36: 23229 23234.
Watanabe, T. et al. (1993) FEBS Lett. 320: 215 218).
Bravo, D.A., Gleason, J. B. et al. (1994) J. Biol. Chem. 269: 25830 25837.
Jean F et al. (2000) Proc. Natl. Acad. Sci. U. S. A. 97: 2864.
Takahashi S et al. (1995) J. Biol. Chem. 270: 26565 26569.
Tsuneoka M et al. (1993) J. Biol. Chem. 268:26461 26465.
Newport G, and Agabian N. (1997) Journal of Biological Chemistry, Nov. 14, 272(46): 28954 61.
Molloy, S. S. et al. (1999) Trends in Cell Biol. 9: 28 35.
Sariola, M. et al (1995) J. Cell Sci. 106:2465-2475.
Ortmann, D. et al. (1994) J. Virol. 68; 2772 2776.
Stieneke Grober, A. et al. (1992) EMBO J. 11: 2407 2414.
Hallenberger, S. et al. (1992) Nature 360: 358 361.
Bolt, G., and Pedersen, I.R. (1998) Virology 252: 387 98.
Vey, M. et al. (1995) Virology 206: 746 9.
Roebroek, A. J. M.et al. (1998) Development 125: 4863 4876.
Takahashi, S. et al. (1993) Biochem. Biophys. Res. Commun. 195: 1019 1026.
Angliker, H. (1995) J. Med. Chem. 38, 4014 4018.
Garten, W. et al. (1994) Biochimie 76: 217 225.
Oda, K. et al. (1996) Biosci. Biotechnol. Biochem. 60: 1388 1389.
Laskowski, M. Jr., and Kato, I. (1980) Ann. Rev. Biochem. 49: 593 626.
Bode, W., and Huber, R. (1992) Eur. J. Biochem. 204: 433 451.
Greagg, M. A. et al. (1994) Biochim. Biophys. Acta 1222: 179 186.
Bae, S. J., and Sturtevant, J. M. (1995) Biophys. Chem. 55: 247 252.
Li, A., and V. Daggett, V. (1995) Protein Engineering 8: 1117 1128.
Grøn, H., and Breddam, K. (1992) Biochemistry 31: 49 53.
Grøn, H. et al. (1992) Biochemistry 31: 6011 6018.
Rockwell, N. C., and Fuller, R. S. (1998) Biochemistry 37: 3386 3391.
Braun, N. J. et al. (1987) Biol. Chem. Hoppe Seyler 368: 299 308.
Angliker et al. (1993) 293:75-81.
Qasim, M. A. et al. (1997) Biochemistry 36: 1598 1607.
Lu, W. et al. (1999) Chem. and Biol. 6: 419 427.
Rink, H. et al. (1984) Nucleic Acid Research 12: 6369 6387.
Takahashi, S. et al (1993) Biochem. Biophys. Res. Commun. 195:1019-1026.
Hipler et al. (1996) Adv. Exp. Med. Biol. 379:43-47.
Heinz et al. (1991) J. Mol. Biol. 217:353-371.
Komiyama & Fuller (2000) Biochem 39:15156-15165.
Hyberts, S.G. et al. (1992) Protein Sc. 1:736-751.
Rockwell N.C., et al., (1997) Biochemistry 36:1912-1917.
Bode W et al. (1986) EMBO J. 5:813-818.

* cited by examiner

Fig. 1

```
     |NdeI    |NcoI
GGGATTCCA/TATGTC/CATGGGTTCTGAACTGAAATCTTTCCCAGAAGTTGTTGGTAAAACTGTTGAC
            M   S   M   G   S   E   L   K   S   F   P   E   V   V   G   K   T   V   D

|AatII
CAGGCTCGTGAATACTTCACTCTGCATTACCCGCAGTACGACGT/CTACTTCCTGCCGGAAGGTTCT
 Q   A   R   E   Y   F   T   L   H   Y   P   Q   Y   D   V   Y   F   L   P   E   G   S

|BglII                         |MluI
CCTGTTACCCGA/GATCTGCGTTACAACCGTGTA/CGCGTTTTCTACAACCCAGGTACTAACGTTGTT
 P   V   T   R   D   L   R   Y   N   R   V   R   V   F   Y   N   P   G   T   N   V   V

|BamHI
AACCATGTTCCGCATGTTGGTTAACG/GATCCCG    (SEQ ID NO:1)
 N   H   V   P   H   V   G   *         (SEQ ID NO:2)
```

Fig. 5

D33G-R4K1
CAGGCTCGTGAATACTTCACTCTGCATTACCCGCAGTAC<u>GG</u>TGTTTACTTCCTGCG
GAAGGTTCTCGTGTTACCAAAGAT    (SEQ ID NO3:)

D33V-R4K1
CAGGCTCGTGAATACTTCACTCTGCATTACCCGCAGTAC<u>GT</u>CGTTTACTTCCTGCC
GGAAGGTTCTCGTGTTACCAAAGAT    (SEQ ID NO:4)

D33I-R4K1
CAGGCTCGTGAATACTTCACTCTGCATTACCCGCAGTAC<u>ATT</u>GTTTACTTCCTGCC
GGAAGGTTCTCGTGTTACCAAAGAT    (SEQ ID NO:5)

Y35I-R4R1
CGTGAATACTTCACTCTGCATTACCCGCAGTACGACGTT<u>ATC</u>TTCCTGCCGGAAGG
TTCTCGTGTTACCCGTGATCTGCGT    (SEQ ID NO:6)

L37G-R4K1
TACTTCACTCTGCATTACCCGCAGTACGACGTTTACTTC<u>GG</u>TCCGGAAGGTTCTCG
TGTTACCAAAGATCTGCGTTACAAC    (SEQ ID NO:7)

E39S-R4R1
ACTCTGCATTACCCGCAGTACGACGTTTACTTCCTGCCG<u>AGC</u>CCCTCTCGTGTTAC
CCGTGATCTGCGTTACAACCGTGTA    (SEQ ID NO:8)

E39P-R4R1
ACTCTGCATTACCCGCAGTACGACGTTTACTTCCTGCCG<u>CCC</u>CCCTCTCGTGTTAC
CCGTGATCTGCGTTACAACCGTGTA    (SEQ ID NO:9)

E39C-R4R1
ACTCTGCATTACCCGCAGTACGACGTTTACTTCCTGCCG<u>TGT</u>CCCTCTCGTGTTAC
CCGTGATCTGCGTTACAACCGTGTA    (SEQ ID NO:10)

E39G-R4R1
ACTCTGCATTACCCGCAGTACGACGTTTACTTCCTGCCG<u>GGC</u>CCCTCTCGTGTTAC
CCGTGATCTGCGTTACAACCGTGTA    (SEQ ID NO:11)

E39T-R4R1: ACT for Thr
ACTCTGCATTACCCGCAGTACGACGTTTACTTCCTGCCG<u>ACT</u>CCCTCTCGTGTTAC
CCGTGATCTGCGTTACAACCGTGTA    (SEQ ID NO:12)

E39T-R4R1: ACC for Thr
ACTCTGCATTACCCGCAGTACGACGTTTACTTCCTGCCG<u>ACC</u>CCCTCTCGTGTTAC
CCGTGATCTGCGTTACAACCGTGTA    (SEQ ID NO:13)

Fig. 5, continued

E39Y-R4R1
ACTCTGCATTACCCGCAGTACGACGTTTACTTCCTGCCG<u>TAT</u>CCCTCTCGTGTTAC
CCGTGATCTGCGTTACAACCGTGTA (SEQ ID NO:14)

E39H-R4R1
ACTCTGCATTACCCGCAGTACGACGTTTACTTCCTGCCG<u>CAC</u>CCCTCTCGTGTTAC
CCGTGATCTGCGTTACAACCGTGTA (SEQ ID NO:15)

G40P-R4R1
CTGCATTACCCGCAGTACGACGTTTACTTCCTGCCGGAA<u>CCC</u>TCTCGTGTTACCCG
TGATCTGCGTTACAACCGTGTACGC (SEQ ID NO:16)

G40A-R4R1
CTGCATTACCCGCAGTACGACGTTTACTTCCTGCCGGAA<u>GCT</u>TCTCGTGTTACCCG
TGATCTGCGTTACAACCGTGTACGC (SEQ ID NO:17)

L47V-R4R1
GTTTACTTCCTGCCGGAAGGTTCTCGTGTTACCCGTGAT<u>GTT</u>CGTTACAACCGTGT
ACGCGTTTTCTACAACCCAGGTACT (SEQ ID NO:18)

Y49A-R4R1
TTCCTGCCGGAAGGTTCTCGTGTTACCCGTGATCTGCGT<u>GCT</u>AACCGTGTACGCGT
TTTCTACAACCCAGGTACTAACGTT (SEQ ID NO:19)

Y49V-R4R1
TTCCTGCCGGAAGGTTCTCGTGTTACCCGTGATCTGCGT<u>GTT</u>AACCGTGTACGCGT
TTTCTACAACCCAGGTACTAACGTT (SEQ ID NO:20)

Y49D-R4R1: GAT for Asp
TTCCTGCCGGAAGGTTCTCGTGTTACCCGTGATCTGCGT<u>GAT</u>AACCGTGTACGCGT
TTTCTACAACCCAGGTACTAACGTT (SEQ ID NO:21)

Y49D-R4R1: GAC for Asp
TTCCTGCCGGAAGGTTCTCGTGTTACCCGTGATCTGCGT<u>GAC</u>AACCGTGTACGCGT
TTTCTACAACCCAGGTACTAACGTT (SEQ ID NO:22)

Y49C-R4R1
TTCCTGCCGGAAGGTTCTCGTGTTACCCGTGATCTGCGT<u>TGC</u>AACCGTGTACGCGT
TTTCTACAACCCAGGTACTAACGTT (SEQ ID NO:23)

N50D-R4R1
CTGCCGGAAGGTTCTCGTGTTACCCGTGATCTGCGTTAC<u>GAC</u>CGTGTACGCGTTTT
CTACAACCCAGGTACTAACGTTGTT (SEQ ID NO:24)

SEQUENCE LISTING

<160> NUMBER OF SEQ ID NOS: 70

<210> SEQ ID NO 1
<211> LENGTH: 232

-continued

```
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (11)..(223)
<223> OTHER INFORMATION:

<400> SEQUENCE: 1
gggattccat atg tcc atg ggt tct gaa ctg aaa tct ttc cca gaa gtt         49
           Met Ser Met Gly Ser Glu Leu Lys Ser Phe Pro Glu Val
             1               5                  10 gtt ggt aaa act gtt gac cag gct cgt gaa tac ttc act ctg cat tac       97
Val Gly Lys Thr Val Asp Gln Ala Arg Glu Tyr Phe Thr Leu His Tyr
 15                  20                  25 ccg cag tac gac gtc tac ttc ctg ccg gaa ggt tct cct gtt acc cga      145
Pro Gln Tyr Asp Val Tyr Phe Leu Pro Glu Gly Ser Pro Val Thr Arg
 30                  35                  40                  45 gat ctg cgt tac aac cgt gta cgc gtt ttc tac aac cca ggt act aac      193
Asp Leu Arg Tyr Asn Arg Val Arg Val Phe Tyr Asn Pro Gly Thr Asn
                     50                  55                  60 gtt gtt aac cat gtt ccg cat gtt ggt taa cggatcccg                    232
Val Val Asn His Val Pro His Val Gly
             65                  70

<210> SEQ ID NO 2
<211> LENGTH: 70
<212> TYPE: PRT
<213> ORGANISM: Artificial Sequence
<220> FEATURE:
<223> OTHER INFORMATION: Synthetic

<400> SEQUENCE: 2

Met Ser Met Gly Ser Glu Leu Lys Ser Phe Pro Glu Val Val Gly Lys
  1               5                  10                  15

Thr Val Asp Gln Ala Arg Glu Tyr Phe Thr Leu His Tyr Pro Gln Tyr
                 20                  25                  30

Asp Val Tyr Phe Leu Pro Glu Gly Ser Pro Val Thr Arg Asp Leu Arg
             35                  40                  45

Tyr Asn Arg Val Arg Val Phe Tyr Asn Pro Gly Thr Asn Val Val Asn
         50                  55                  60

His Val Pro His Val Gly
 65                  70

<210> SEQ ID NO 3
<211> LENGTH: 80
<212> TYPE: DNA
<213> ORGANISM: Artificial Sequence
<220> FEATURE:
<223> OTHER INFORMATION: Synthetic

<400> SEQUENCE: 3
caggctcgtg aatacttcac tctgcattac ccgcagtacg gtgtttactt cctgcggaag    60
gttctcgtgt taccaaagat                                                80

<210> SEQ ID NO 4
<211> LENGTH: 81
<212> TYPE: DNA
<213> ORGANISM: Artificial Sequence
<220> FEATURE:
<223> OTHER INFORMATION: Synthetic

<400> SEQUENCE: 4
```
caggctcgtg aatacttcac tctgcattac ccgcagtacg tcgtttactt cctgccggaa    60
ggttctcgtg ttaccaaaga t                                              81

<210> SEQ ID NO 5
<211> LENGTH: 81
<212> TYPE: DNA
<213> ORGANISM: Artificial Sequence
<220> FEATURE:
<223> OTHER INFORMATION: Synthetic

<400> SEQUENCE: 5
caggctcgtg aatacttcac tctgcattac ccgcagtaca ttgtttactt cctgccggaa    60
ggttctcgtg ttaccaaaga t                                              81

<210> SEQ ID NO 6
<211> LENGTH: 81
<212> TYPE: DNA
<213> ORGANISM: Artificial Sequence
<220> FEATURE:
<223> OTHER INFORMATION: Synthetic

<400> SEQUENCE: 6
cgtgaatact tcactctgca tttacccgcag tacgacgtta tcttcctgcc ggaaggttct    60
cgtgttaccc gtgatctgcg t                                              81

<210> SEQ ID NO 7
<211> LENGTH: 81
<212> TYPE: DNA
<213> ORGANISM: Artificial Sequence
<220> FEATURE:
<223> OTHER INFORMATION: Synthetic

<400> SEQUENCE: 7
tacttcactc tgcattaccc gcagtacgac gtttacttcg gtccggaagg ttctcgtgtt    60
accaaagatc tgcgttacaa c                                              81

<210> SEQ ID NO 8
<211> LENGTH: 81
<212> TYPE: DNA
<213> ORGANISM: Artificial Sequence
<220> FEATURE:
<223> OTHER INFORMATION: Synthetic

<400> SEQUENCE: 8
actctgcatt acccgcagta cgacgtttac ttcctgccga gcccctctcg tgttacccgt    60
gatctgcgtt acaaccgtgt a                                              81

<210> SEQ ID NO 9
<211> LENGTH: 81
<212> TYPE: DNA
<213> ORGANISM: Artificial Sequence
<220> FEATURE:
<223> OTHER INFORMATION: Synthetic

<400> SEQUENCE: 9
actctgcatt acccgcagta cgacgtttac ttcctgccgc cccctctcg tgttacccgt     60 gatctgcgtt acaaccgtgt a                                              81

<210> SEQ ID NO 10
<211> LENGTH: 81
<212> TYPE: DNA

<213> ORGANISM: Artificial Sequence
<220> FEATURE:
<223> OTHER INFORMATION: Synthetic

<400> SEQUENCE: 10

```
actctgcatt acccgcagta cgacgtttac ttcctgccgt gtccctctcg tgttacccgt    60
gatctgcgtt acaaccgtgt a                                              81
```

<210> SEQ ID NO 11
<211> LENGTH: 81
<212> TYPE: DNA
<213> ORGANISM: Artificial Sequence
<220> FEATURE:
<223> OTHER INFORMATION: Synthetic

<400> SEQUENCE: 11

```
actctgcatt acccgcagta cgacgtttac ttcctgccgg gccctctcg tgttacccgt     60 gatctgcgtt acaaccgtgt a                                              81
```

<210> SEQ ID NO 12
<211> LENGTH: 81
<212> TYPE: DNA
<213> ORGANISM: Artificial Sequence
<220> FEATURE:
<223> OTHER INFORMATION: Synthetic

<400> SEQUENCE: 12

```
actctgcatt acccgcagta cgacgtttac ttcctgccga ctccctctcg tgttacccgt    60
gatctgcgtt acaaccgtgt a                                              81
```

<210> SEQ ID NO 13
<211> LENGTH: 81
<212> TYPE: DNA
<213> ORGANISM: Artificial Sequence
<220> FEATURE:
<223> OTHER INFORMATION: Synthetic

<400> SEQUENCE: 13

```
actctgcatt acccgcagta cgacgtttac ttcctgccga ccccctctcg tgttacccgt    60
gatctgcgtt acaaccgtgt a                                              81
```

<210> SEQ ID NO 14
<211> LENGTH: 81
<212> TYPE: DNA
<213> ORGANISM: Artificial Sequence
<220> FEATURE:
<223> OTHER INFORMATION: Synthetic

<400> SEQUENCE: 14

```
actctgcatt acccgcagta cgacgtttac ttcctgccgt atccctctcg tgttacccgt    60
gatctgcgtt acaaccgtgt a                                              81
```

<210> SEQ ID NO 15
<211> LENGTH: 81
<212> TYPE: DNA
<213> ORGANISM: Artificial Sequence
<220> FEATURE:
<223> OTHER INFORMATION: Synthetic

<400> SEQUENCE: 15

```
actctgcatt acccgcagta cgacgtttac ttcctgccgc accctctcg tgttacccgt     60 gatctgcgtt acaaccgtgt a                                              81
```

<210> SEQ ID NO 16
<211> LENGTH: 81
<212> TYPE: DNA
<213> ORGANISM: Artificial Sequence
<220> FEATURE:
<223> OTHER INFORMATION: Synthetic

<400> SEQUENCE: 16
ctgcattacc cgcagtacga cgtttacttc ctgccggaac cctctcgtgt tacccgtgat    60
ctgcgttaca accgtgtacg c                                              81

<210> SEQ ID NO 17
<211> LENGTH: 81
<212> TYPE: DNA
<213> ORGANISM: Artificial Sequence
<220> FEATURE:
<223> OTHER INFORMATION: Synthetic

<400> SEQUENCE: 17
ctgcattacc cgcagtacga cgtttacttc ctgccggaag cttctcgtgt tacccgtgat    60
ctgcgttaca accgtgtacg c                                              81

<210> SEQ ID NO 18
<211> LENGTH: 81
<212> TYPE: DNA
<213> ORGANISM: Artificial Sequence
<220> FEATURE:
<223> OTHER INFORMATION: Synthetic

<400> SEQUENCE: 18
gtttacttcc tgccggaagg ttctcgtgtt acccgtgatg ttcgttacaa ccgtgtacgc    60
gttttctaca acccaggtac t                                              81

<210> SEQ ID NO 19
<211> LENGTH: 81
<212> TYPE: DNA
<213> ORGANISM: Artificial Sequence
<220> FEATURE:
<223> OTHER INFORMATION: Synthetic

<400> SEQUENCE: 19
ttcctgccgg aaggttctcg tgttacccgt gatctgcgtg ctaaccgtgt acgcgttttc    60
tacaacccag gtactaacgt t                                              81

<210> SEQ ID NO 20
<211> LENGTH: 81
<212> TYPE: DNA
<213> ORGANISM: Artificial Sequence
<220> FEATURE:
<223> OTHER INFORMATION: Synthetic

<400> SEQUENCE: 20
ttcctgccgg aaggttctcg tgttacccgt gatctgcgtg ttaaccgtgt acgcgttttc    60
tacaacccag gtactaacgt t                                              81

<210> SEQ ID NO 21
<211> LENGTH: 81
<212> TYPE: DNA
<213> ORGANISM: Artificial Sequence
<220> FEATURE:
<223> OTHER INFORMATION: Synthetic

```
<400> SEQUENCE: 21
ttcctgccgg aaggttctcg tgttacccgt gatctgcgtg ataaccgtgt acgcgttttc      60
tacaacccag gtactaacgt t                                               81

<210> SEQ ID NO 22
<211> LENGTH: 81
<212> TYPE: DNA
<213> ORGANISM: Artificial Sequence
<220> FEATURE:
<223> OTHER INFORMATION: Synthetic

<400> SEQUENCE: 22
ttcctgccgg aaggttctcg tgttacccgt gatctgcgtg acaaccgtgt acgcgttttc      60
tacaacccag gtactaacgt t                                               81

<210> SEQ ID NO 23
<211> LENGTH: 81
<212> TYPE: DNA
<213> ORGANISM: Artificial Sequence
<220> FEATURE:
<223> OTHER INFORMATION: Synthetic

<400> SEQUENCE: 23
ttcctgccgg aaggttctcg tgttacccgt gatctgcgtt gcaaccgtgt acgcgttttc      60
tacaacccag gtactaacgt t                                               81

<210> SEQ ID NO 24
<211> LENGTH: 81
<212> TYPE: DNA
<213> ORGANISM: Artificial Sequence
<220> FEATURE:
<223> OTHER INFORMATION: Synthetic

<400> SEQUENCE: 24
ctgccggaag gttctcgtgt tacccgtgat ctgcgttacg accgtgtacg cgttttctac      60
aacccaggta ctaacgttgt t                                               81

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Ser Met Gly Ser Glu Leu Lys
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Thr Glu Phe Gly Ser Glu Leu Lys
1               5

<210> SEQ ID NO 27
<211> LENGTH: 6
<212> TYPE: PRT
<213> ORGANISM: Artificial Sequence
```

-continued

<220> FEATURE:
<223> OTHER INFORMATION: Synthetic

<400> SEQUENCE: 27

Ser Met Gly Ser Glu Leu
1               5

<210> SEQ ID NO 28
<211> LENGTH: 34
<212> TYPE: DNA
<213> ORGANISM: Artificial Sequence
<220> FEATURE:
<223> OTHER INFORMATION: Synthetic

<400> SEQUENCE: 28
ttacttcctg ccggaaggtt ctcctgttac cctg                              34

<210> SEQ ID NO 29
<211> LENGTH: 42
<212> TYPE: DNA
<213> ORGANISM: Artificial Sequence
<220> FEATURE:
<223> OTHER INFORMATION: Synthetic

<400> SEQUENCE: 29
gatccagggt aacaggagaa ccttccggca ggaagtaaac gt                     42

<210> SEQ ID NO 30
<211> LENGTH: 34
<212> TYPE: DNA
<213> ORGANISM: Artificial Sequence
<220> FEATURE:
<223> OTHER INFORMATION: Synthetic

<400> SEQUENCE: 30
ttacttcctg ccggaaggtt ctcctgttac ccgt                              34

<210> SEQ ID NO 31
<211> LENGTH: 42
<212> TYPE: DNA
<213> ORGANISM: Artificial Sequence
<220> FEATURE:
<223> OTHER INFORMATION: Synthetic

<400> SEQUENCE: 31
gatcacgggt aacaggagaa ccttccggca ggaagtaaac gt                     42

<210> SEQ ID NO 32
<211> LENGTH: 34
<212> TYPE: DNA
<213> ORGANISM: Artificial Sequence
<220> FEATURE:
<223> OTHER INFORMATION: Synthetic

<400> SEQUENCE: 32
ttacttcctg ccggaaggtt ctcgtgttac cctg                              34

<210> SEQ ID NO 33
<211> LENGTH: 42
<212> TYPE: DNA
<213> ORGANISM: Artificial Sequence
<220> FEATURE:
<223> OTHER INFORMATION: Synthetic

<400> SEQUENCE: 33
gatccagggt aacaggagaa ccttccggca ggaagtaaac gt                     42

<210> SEQ ID NO 34
<211> LENGTH: 34
<212> TYPE: DNA
<213> ORGANISM: Artificial Sequence
<220> FEATURE:
<223> OTHER INFORMATION: Synthetic

<400> SEQUENCE: 34
ttacttcctg ccggaaggtt ctatggttac ccgt                                    34

<210> SEQ ID NO 35
<211> LENGTH: 42
<212> TYPE: DNA
<213> ORGANISM: Artificial Sequence
<220> FEATURE:
<223> OTHER INFORMATION: Synthetic

<400> SEQUENCE: 35
gatcacgggt aaccatagaa ccttccggca ggaagtaaac gt                           42

<210> SEQ ID NO 36
<211> LENGTH: 34
<212> TYPE: DNA
<213> ORGANISM: Artificial Sequence
<220> FEATURE:
<223> OTHER INFORMATION: Synthetic

<400> SEQUENCE: 36
ttacttcctg ccggaaggtt ctcgtgttac ccgt                                    34

<210> SEQ ID NO 37
<211> LENGTH: 42
<212> TYPE: DNA
<213> ORGANISM: Artificial Sequence
<220> FEATURE:
<223> OTHER INFORMATION: Synthetic

<400> SEQUENCE: 37
gatcacgggt aacacgagaa ccttccggca ggaagtaaac gt                           42

<210> SEQ ID NO 38
<211> LENGTH: 34
<212> TYPE: DNA
<213> ORGANISM: Artificial Sequence
<220> FEATURE:
<223> OTHER INFORMATION: Synthetic

<400> SEQUENCE: 38
ttacttcctg ccggaacgtt ctcgtgttac ccgt                                    34

<210> SEQ ID NO 39
<211> LENGTH: 42
<212> TYPE: DNA
<213> ORGANISM: Artificial Sequence
<220> FEATURE:
<223> OTHER INFORMATION: Synthetic

<400> SEQUENCE: 39
gatcacgggt aacacgagaa cgttccggca ggaagtaaac gt                           42

<210> SEQ ID NO 40
<211> LENGTH: 34
<212> TYPE: DNA
<213> ORGANISM: Artificial Sequence
<220> FEATURE:

```
<223> OTHER INFORMATION: Synthetic

<400> SEQUENCE: 40
ttacttcctg ccggaaggtt ctcctgttaa acgt                                34

<210> SEQ ID NO 41
<211> LENGTH: 42
<212> TYPE: DNA
<213> ORGANISM: Artificial Sequence
<220> FEATURE:
<223> OTHER INFORMATION: Synthetic

<400> SEQUENCE: 41
gatcacgttt aacaggagaa ccttccggca ggaagtaaac gt                       42

<210> SEQ ID NO 42
<211> LENGTH: 34
<212> TYPE: DNA
<213> ORGANISM: Artificial Sequence
<220> FEATURE:
<223> OTHER INFORMATION: Synthetic

<400> SEQUENCE: 42
ttacttcctg ccggaaggtt ctatggttaa acgt                                34

<210> SEQ ID NO 43
<211> LENGTH: 42
<212> TYPE: DNA
<213> ORGANISM: Artificial Sequence
<220> FEATURE:
<223> OTHER INFORMATION: Synthetic

<400> SEQUENCE: 43
gatcacgttt aaccatagaa ccttccggca ggaagtaaac gt                       42

<210> SEQ ID NO 44
<211> LENGTH: 34
<212> TYPE: DNA
<213> ORGANISM: Artificial Sequence
<220> FEATURE:
<223> OTHER INFORMATION: Synthetic

<400> SEQUENCE: 44
ttacttcctg ccggaaggtt ctcctgttaa acgt                                34

<210> SEQ ID NO 45
<211> LENGTH: 42
<212> TYPE: DNA
<213> ORGANISM: Artificial Sequence
<220> FEATURE:
<223> OTHER INFORMATION: Synthetic

<400> SEQUENCE: 45
gatcacgttt aacacgagaa ccttccggca ggaagtaaac gt                       42

<210> SEQ ID NO 46
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: The n at these positions can be any nucleotide.

<400> SEQUENCE: 46
```
ccgcagtacn nygtttactt cctgccggaa                                        30

<210> SEQ ID NO 47
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: The n at these positions can be any nucleotide.

<400> SEQUENCE: 47
gaagtaaacr nngtactgcg ggtaatgcag                                        30

<210> SEQ ID NO 48
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: The n at these positions can be any nucleotide.

<400> SEQUENCE: 48
tnnyttcctg ccggaaggtt ctcgtgttac ccgt                                   34

<210> SEQ ID NO 49
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(37)
<223> OTHER INFORMATION: The n at these positions can be any nucleotide.

<400> SEQUENCE: 49
gatcacgggt aacacgagaa ccttccggca ggaarnnaac gt                          42

<210> SEQ ID NO 50
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: The n at these positions can be any nucleotide.

<400> SEQUENCE: 50
ttacttcnny ccggaaggtt ctcgtgttac ccgt                                   34

<210> SEQ ID NO 51
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(31)
<223> OTHER INFORMATION: The n at these positions can be any nucleotide.

```
<400> SEQUENCE: 51
gatcacgggt aacacgagaa ccttccggrn ngaagtaaac gt                        42

<210> SEQ ID NO 52
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(15)
<223> OTHER INFORMATION: The n at these positions can be any nucleotide.

<400> SEQUENCE: 52
ttacttcctg ccgnnyggtt ctcgtgttac ccgt                                 34

<210> SEQ ID NO 53
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(25)
<223> OTHER INFORMATION: The n at these positions can be any nucleotide.

<400> SEQUENCE: 53
gatcacgggt aacacgagaa ccrnncggca ggaagtaaac gt                        42

<210> SEQ ID NO 54
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(18)
<223> OTHER INFORMATION: The n at these positions can be any nucleotide.

<400> SEQUENCE: 54
ttacttcctg ccggaannyt ctcgtgttac ccgt                                 34

<210> SEQ ID NO 55
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(22)
<223> OTHER INFORMATION: The n at these positions can be any nucleotide.

<400> SEQUENCE: 55
gatcacgggt aacacgagar nnttccggca ggaagtaaac gt                        42

<210> SEQ ID NO 56
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: The n at these positions can be any nucleotide.
```

<400> SEQUENCE: 56
acccgtgatn nycgttacaa ccgtgttcgc                                              30

<210> SEQ ID NO 57
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: The n at these positions can be any nucleotide.

<400> SEQUENCE: 57
gttgtaacgr nnatcacggg taacacgaga                                              30

<210> SEQ ID NO 58
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: The n at these positions can be any nucleotide.

<400> SEQUENCE: 58
gatctgcgtn nyaaccgtgt tcgcgttttc                                              30

<210> SEQ ID NO 59
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: The n at these positions can be any nucleotide.

<400> SEQUENCE: 59
aacacggttr nnacgcagat cacgggtcaa                                              30

<210> SEQ ID NO 60
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: The n at these positions can be any nucleotide.

<400> SEQUENCE: 60
ctgcgttacn nycgtgttcg cgttttctac                                              30

<210> SEQ ID NO 61
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)

<223> OTHER INFORMATION: The n at these positions can be any nucleotide.

<400> SEQUENCE: 61
gcgaacacgr nngtaacgca gatcacgggt                                30

<210> SEQ ID NO 62
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: The n at these positions can be any nucleotide.

<400> SEQUENCE: 62
ctgcgtnnna accgtgtacg cgttttc                                   27

<210> SEQ ID NO 63
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(16)
<223> OTHER INFORMATION: The n at these positons can be any nucleotide.

<400> SEQUENCE: 63
cgcgtacacg gttnnnacgc agatcac                                   27

<210> SEQ ID NO 64
<211> LENGTH: 13
<212> TYPE: PRT
<213> ORGANISM: Artificial Sequence
<220> FEATURE:
<223> OTHER INFORMATION: Synthetic

<400> SEQUENCE: 64

Arg Glu Pro Met Tyr Lys Arg Glu Ala Glu Ala Lys Arg
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(6)
<223> OTHER INFORMATION: The residues at these positions can be any
      amino acid.

<400> SEQUENCE: 65

Arg Lys Xaa Xaa Xaa Xaa Glu Ala Glu Ala Glu Arg
1               5                   10

<210> SEQ ID NO 66
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)

-continued

```
<223> OTHER INFORMATION: The residues at these positions can be any
      amino acid.

<400> SEQUENCE: 66

Asp Xaa Xaa Asp
1

<210> SEQ ID NO 67
<211> LENGTH: 6
<212> TYPE: PRT
<213> ORGANISM: Artificial Sequence
<220> FEATURE:
<223> OTHER INFORMATION: Synthetic

<400> SEQUENCE: 67

Ser Met Gly Ser Glu Leu
1               5

<210> SEQ ID NO 68
<211> LENGTH: 4
<212> TYPE: PRT
<213> ORGANISM: Artificial Sequence
<220> FEATURE:
<223> OTHER INFORMATION: Synthetic

<400> SEQUENCE: 68

Arg Thr Lys Arg
1

<210> SEQ ID NO 69
<211> LENGTH: 4
<212> TYPE: PRT
<213> ORGANISM: Artificial Sequence
<220> FEATURE:
<223> OTHER INFORMATION: Synthetic

<400> SEQUENCE: 69

Arg Val Arg Arg
1

<210> SEQ ID NO 70
<211> LENGTH: 5
<212> TYPE: PRT
<213> ORGANISM: Artificial Sequence
<220> FEATURE:
<223> OTHER INFORMATION: Synthetic

<400> SEQUENCE: 70

Glu Arg Thr Lys Arg
1               5
```

EGLIN C BASED DRUGS FOR TREATMENT OF DISEASE

This application claims priority from provisional application Ser. No. 60/299,096, filed Jun. 18, 2001, which it incorporates by reference in its entirety.

This invention was made in part during work partially supported by the U.S. National Institutes of Health, Institute of General Medical Sciences grant #GM39697. The United States government may have certain rights in the invention.

FIELD OF THE INVENTION

The present invention relates to eglin c variants that inhibit proprotein convertases, and in particular to eglin c variants with mutations at adventitious contact sites for treatment of diseases including acute bacterial and viral infections.

BACKGROUND OF THE INVENTION

Processing of latent precursor proteins by proprotein convertases (PCs) into their biologically active products is a common mechanism required for many important biological functions. This process is tightly regulated, leading to the generation of active peptides and proteins, including neuropeptides and polypeptide hormones, protein tyrosine phosphatases, growth factors and hormones and their respective receptors, and enzymes including matrix metalloproteases. These processing reactions occurs at pairs of basic amino acids. Within the past several years, a novel family of Ca2+-dependent serine proteases has been identified, all of which possess homology to the endoproteases subtilisin (from bacteria) and kexin (from yeast). This family of PCs, or furin/kexin family, is currently comprised of fewer than a dozen members, which include furin/paired basic amino-acid cleaving enzyme (PACE), PC1/PC3, PC2, PC4, PACE4, PC5/PC6, and PC7/PC8 lymphoma proprotein convertase. They share a high degree of amino-acid identity of 50–70% within their catalytic domains.

Recent reports have supported a possible functional role for PCs in a number of diseases. These diseases include tumorigenesis, Alzheimer's disease, and acute bacterial and viral diseases. For example, the role of PCs in tumorigenesis may be due to their activation of matrix metalloproteases precursors into their mature form, such as stromelysin 3 and membrane-type metallproteinases, as well as growth factors and adhesion molecules such as E-cadherin, all of which show similar amino-acid motifs. The role of PCs in bacterial and viral diseases are thought to be due to their ability to cleave and thus render active bacterial enterotoxins and viral envelope glycoproteins.

Thus, furin, and possibly other members of the kexin/furin family, may also play important roles in bacterial and viral pathogenesis. Several bacterial toxins, including *Pseudomonas* exotoxin A, Diphtheria toxin, and Anthrax protective antigen, are synthesized as precursors that undergo processing by a host cell protease at furin-type cleavage sites (Arg-Xaa-Xaa-Arg-) (Molloy, S. S. et at (1999). Trends in Cell Biol. 9: 28–35). Purified furin has been shown to cleave several bacterial protoxins, and tissue culture cell lines that lack a gene encoding furin are resistant to toxins (Molloy, S. S. et al (1992). J. Biol. Chem. 267: 16396–16402; Chiron, M. F. et al (1994) J. Biol. Chem. 269: 18167–18176; Inocencio, N. M. et al. (1994) J. Biol. Chem. 269: 31831–31835; Garred, O. et al. (1994) J. Biol. Chem. 270: 10817–21). Additionally, the viral envelope glycoproteins of numerous lipid-enveloped viruses require processing by a furin-like enzyme (Molloy, S. S. et al (1999). Trends in Cell Biol. 9, 28–35). These include the glycoproteins of many pathogenic human and animal viruses that include the fowl plague influenza virus, Semliki forest virus, Newcastle disease virus, parainfluenza viruses, measles, Herpes viruses, Ebola virus, and various retroviruses (Sariola, M. et al. (1995) J. Cell Sci. 106: 2465–2475; Moehring, J. M. et al. (1993) J. Biol. Chem. 268: 2590–4; Ortmann, D. et al (1994) J. Virol. 68; 2772–2776; Stieneke-Grober, A. et al (1992) EMBO J. 11: 2407–2414; Hallenberger, S. et al (1992) Nature 360: 358–361; Gao, P. et at (1999) J. Viol. 73: 3184–3189; Bolt, G., and Pedersen, I. R. (1998) Virology 252: 387–98; Volchkov, V. et al (1998) Proc. Natl. Acad. Sci. U.S. 95: 5762–5767; Richt, J. A. et al. (1998) J. Viorology 72: 4528–4533; Watanabe, M. et al (1995) J. Virology 69: 3206–3210; Vey, M. et al (1995) Virology 206: 746–9; Stadler, K. et al. (1997) J. Viol. 71: 8475–81).

Although knocking out the fur gene in mouse results in developmental lethality (Roebroek, A. J. M. et al. (1998) Development 125: 4863–4876), the viability of furin-deficient cell lines (Robertson, B. J. et al. (1993) J. Biol. Chem. 268: 24274–24277; Takahashi, S. et al (1993) Biochem. Biophys. Res. Commun. 195: 1019–1026) which were selected based upon their resistance to bacterial and viral infections (Moehring J M et al. (1993) J. Biol. Chem. February 5, 268 (4): 2590–4) suggests that this host processing pathway might offer a novel target for the development of broad-spectrum drugs for treatment of acute bacterial and viral infection. Peptidyl chloromethylketones have been synthesized that inhibit both kexin (Angliker, H. et al. (1993) Biochem. J. 293: 75–81) and furin (Angliker, H. (1995) J. Med. Chem. 38, 4014–4018). Acylated peptidyl-chloromethylketones have been shown to inhibit furin-type processing in cell culture (Garten, W. et al (1994) Biochimie 76: 217–225). However, concerns about toxicity limit the possible therapeutic applications of these molecules. Several protein inhibitors of processing proteases have been described, including engineered ovomucoid third-domain inhibitors (Lu, W. et at (1993) J. Biol. Chem. 268: 14583–14585), serpin variants (Jean, F. et al (1998) Proc. Natl. Acad. Sci. U.S.A. 95: 7293–7298; Dahlen, J. R. et al (1998) J. Biol. Chem. 273: 1851–1854), and "kexstatin," a molecule related to the *Streptomyces* subtilisin inhibitor (Oda, K. et al (1996) Biosci. Biotechnol. Biochem. 60: 1388–1389.). Of these molecules, the genetically engineered serpin a1-PDX is the best characterized and most specific protein inhibitor of furin (Jean, F. et al. (1998) Proc. Natl. Acad. Sci. U.S.A. 95: 7293–7298). Inhibition of processing by a1-PDX in vivo has been demonstrated both by expressing the a1-PDX gene in target cells and by adding the purified protein to tissue culture media (Watanabe, M. et al. (1995) J. Virology 69: 3206–3210; Jean, F. et al. (1998) Proc. Natl. Acad. Sci. U.S.A. 95: 7293–7298; Anderson, E. D. et al. (1993) J. Biol. Chem. 268: 24887–24891). However, the large size (~400 a.a.) and relative instability of serpin family inhibitors hamper the development of these molecules for therapeutic use.

Thus, what is needed are non-toxic inhibitors of PCs; preferably, such inhibitors would be small, stable, and reversible.

SUMMARY OF THE INVENTION

The present invention provides non-toxic inhibitors of PCs and related enzymes which are specific or selective or both. The present invention also provides inhibitors which are small, stable, and reversible. The present invention further provides inhibitors of PCs and related enzymes which can be used in treating diseases, particularly bacterial or viral diseases.

In one aspect, the invention provides a protease inhibitor that is an eglin c variant comprising at least one non-naturally occurring amino acid in an adventitious contact site. In one embodiment, at least one non-naturally occurring amino acid replaces at least one naturally occurring amino acid in an adventitious contact site. In yet another embodiment, at least one non-naturally occurring amino acid replaces at least one naturally occurring amino acid including but not limited to Asp33, Tyr35, Leu37, Glu39, Gly40, Leu47, Tyr49, Asn50, His65, or His68, wherein the numbers specify amino acid positions in native eglin c, and the amino acids are the naturally occurring amino acids at the specified amino position in native eglin c. In a particular embodiment, the non-naturally occurring amino acid Asp replaces Tyr49, or the non-naturally occurring amino acid valine replaces Asp33.

In another aspect, the present invention provides a protease inhibitor that is an eglin c variant comprising at least one non-naturally occurring amino acid in an adventitious contact site, and further comprising at least one non-naturally occurring amino acid in a reactive loop. In one embodiment, at least one non-naturally occurring amino acid in the reactive site loop replaces at least one naturally occurring amino acid in the reactive loop. In another embodiment, at least one non-naturally occurring amino acid replaces at least one naturally occurring amino acid in the reactive loop at one or more sites including but not limited to P1, P2, P3, P4, P5, or P6. In particular embodiments, at least one non-naturally occurring amino acid in the reactive loop replaces at least one naturally occurring amino acid at sites including but not limited to positions P1 or P4 or both. In other particular embodiments, a non-naturally occurring amino acid in the reactive loop is includes but is not limited to one or more of Arg (R) at position P4, Arg (R) at P1, or Lys (K) at position P1.

In another aspect, the present invention provides a protease inhibitor that is an eglin c variant comprising variants R4-, M4R1-, R4R1-, M4K1-, R4K1-, R6R4F1-, K2R1-, M4K2R1-, or R4K2R1-eglin, where amino acid substitutions in the reactive site loop are indicated by the letter of the non-naturally occurring amino acid, and the position in the reactive site loop which it occupies, and where the variant further comprises at least one non-naturally occurring amino acid in an adventitious contact site. In one embodiment, the eglin c variant inhibitor includes but is not limited to R4R1- or R4K1-eglin, where the variant further comprises at least one non-naturally occurring amino acid in an adventitious contact site. In another embodiment, the present invention provides an eglin c variant comprising an eglin c variant inhibitor includes but is not limited to eglin c variants R4-, M4R1-, R4R1-, M4K1-, R4K1-, R6R4F1-, K2R1-, M4K2R1-, R4K2R1-eglin, where the variant further comprises at least one non-naturally occurring amino acid in an adventitious contact site which replaces at least one naturally occurring amino acid, where the naturally occurring amino acid includes but is not limited to Asp33, Tyr35, Leu37, Glu39, Gly40, Leu47, Tyr49, Asn50, His65, or His68, where the numbers specify amino acid positions in native eglin c, and the amino acids are the naturally occurring amino acids at the specified amino position in native eglin c. In particular embodiments, the eglin c variant inhibitor comprises R4R1- or R4K1-eglin, and at least one non-naturally occurring amino acid in an adventitious contact site replaces at least one naturally occurring amino acid comprising Asp33, Tyr35, Leu37, Glu39, Gly40, Leu47, Tyr49, Asn50, His65, or His68. In other particular embodiments, the eglin c variant comprises R4R1- or R4K1-eglin, and the non-naturally occurring amino acid in the adventitious contact site comprises Asp replacing Tyr49, Val replacing Asp33, or both Asp replacing Tyr49 and Val replacing Asp33. In yet other particular embodiments, the eglin c variant comprises the R4R1-eglin, and the non-naturally occurring amino acids in the adventitious contact sites are Asp replacing Tyr49 and Val replacing Asp33.

The present invention also provides an isolated nucleic acid molecule comprising a nucleotide sequence encoding any of the eglin c variants described above. The present invention also provides an expression vector comprising a nucleotide sequence encoding any of the eglin c variants described above. The present invention also provides a host cell comprising a nucleotide sequence encoding any of the eglin c variants described above. In some embodiments, the host cells include but are not limited to bacterial cells, yeast cells, plant cells, and animal cells. In other embodiments, the animal cells include but are not limited to insect cells, avian cells, and mammalian cells.

The present invention also provides a composition comprising any of the eglin c variants expressed by a host cell which comprises a nuleotide sequence encoding an eglin c variant as described above.

The present invention also provides an eglin c variant as described above which blocks endoproteolytic activation of a bacterial toxin. In some embodiments, the bacterial toxin includes but is not limited to anthrax toxin protective antigen, dipthera toxin, *Pseudomonas* aeruogenosa exotoxin A, and shiga toxin. The present invention also provides an eglin c variant as decscribed above which blocks endoproteolytic activation of a viral coat glycoprotein. In some embodiments, the viral coat glycoprotein includes but is not limited to respiratory syncytial viruses, measles viruses, ebola viruses, paramyxoviruses, encephalitis viruses, hantaviruses, fowl plague or type A influenza viruses, human immunodeficiency viruses, human cytomegaloviruses, mouse mammary tumor virus-7, Newcastle disease viruses, Sindbis viruses, and human parainfluenza virus type 3. The present invention also provides an eglin c variant as described above which blocks endoproteolytic activation of a fungal protein. In some embodiments, the fungal protein is from a fungus including but not limited to candidiasis, *aspergillus* infections and *pneumocystis* pneumonia.

The present invention also provides a pharmaceutically acceptable composition comprising a therapeutically effective amount of any of the eglin c variants described above; in some embodiments, the composition further comprises a pharmaceutically effective carrier or diluent.

The present invention further provides a method of inhibiting bacterial infection of cells comprising contacting cells with an eglin c variant as described above. In some embodiments, the bacteria include but are not limited to *Bacillus anthracis, Corynebactrium diptheriae, Pseudomonas aeruogenosa*, and shiga. The present invention also provides a method of inhibiting viral infection of cells comprising contacting cells with an eglin c variant as described above. In some embodiments, the viruses include but are not limited to respiratory syncytial viruses, measles viruses, paramyxoviruses, encephalitis viruses, hanta viruses, fowl plague or type A influenza viruses, human immunodeficiency viruses, human cytomegaloviruses, mouse mammary tumor virus-7, Newcastle disease viruses, Sindbis viruses, and human parainfluenza virus type 3. The present invention also provides a method of inhibiting fungal infection of cells comprising contacting cells with an an eglin c variant as described above. In some embodiment, the fungi include but are not limited to candidiasis, *aspergillus* infections and *pneumocystis* pneumonia.

The present invention also provides a method of blocking endoproteolytic activation of a bacterial toxin comprising contacting a cell in the presence of the toxin with an eglin c variant as described above. In some embodiments, the bacterial toxin includes but is not limited to anthrax toxin protective antigen, dipthera toxin, *Pseudomonas* aeruogenosa exotoxin A, and shiga toxin. The present invention also provides a method of blocking endoproteolytic activation of a viral coat glycoprotein, comprising contacting a cell in the presence of the glycoprotein with an eglin c variant as described above. In some embodiments, the viral coat glycoprotein includes but is not limited to respiratory syncytial viruses, measles viruses, ebola viruses, paramyxoviruses, encephalitis viruses, hantaviruses, fowl plague or type A influenza viruses, human immunodeficiency viruses, human cytomegaloviruses, mouse mammary tumor virus-7, Newcastle disease viruses, Sindbis viruses, and human parainfluenza virus type 3. The present invention also provides a method of blocking endoproteolytic activation of a fungal protein, comprising contacting a cell in the presence of the fungal protein with an eglin c variant as described above. In some embodiments, the fungal protein is from a fungus including but not limited to candidiasis, *aspergillus* infections and *pneumocystis* pneumonia.

The present invention also provides a method of treating a patient acutely infected with an infectious agent, comprising administering to the patient a therapeutically effective amount of an eglin c variant as described above. In some embodiments, the infectious agent is a bacterial, viral, or fungal disease, where disease progression is dependent upn a proprotein processing convertase or similar enzyme. In some embodiments, bacteria include but are not limited to *Bacillus anthracis*, Corynebactrium diptheriae, *Pseudomonas* aeruogenosa, and shiga. In other embodiments, viruses include but are not limited to respiratory syncytial viruses, measles viruses, paramyxoviruses, encephalitis viruses, hanta viruses, fowl plague or type A influenza viruses, human immunodeficiency viruses, human cytomegaloviruses, mouse mammary tumor virus-7, Newcastle disease viruses, Sindbis viruses, and human parainfluenza virus type 3. In yet other embodiments, fungi include but are not limited to candidiasis, *aspergillus* infections and *pneumocystis* pneumonia.

The present invention also provides a method of treating a patient exposed to an infectious agent, comprising administering to the patient a therapeutically effective amount of an eglin c variant as described above, under conditions sufficient to prevent or ameliorate the appearance of disease symptoms. In some embodiments, the infectious agent is a bacterial, viral, or fungal disease, where disease progression is dependent upn a proprotein processing convertase or similar enzyme. In some embodiments, bacteria include but are not limited to *Bacillus anthracis, Corynebactrium diptheriae, Pseudomonas aeruogenosa*, and *shiga*. In other embodiments, viruses include but are not limited to respiratory syncytial viruses, measles viruses, paramyxoviruses, encephalitis viruses, hanta viruses, fowl plague or type A influenza viruses, human immunodeficiency viruses, human cytomegaloviruses, mouse mammary tumor virus-7, Newcastle disease viruses, Sindbis viruses, and human parainfluenza virus type 3. In yet other embodiments, fungi include but are not limited to candidiasis, *aspergillus* infections and *pneumocystis* pneumonia.

The present invention further provides methods of producing a protease inhibitor that is an eglin c variant comprising at least one non-naturally occurring amino acid in an adventitious contact site, where the method comprises providing an eglin c, randomly mutagenizing selected adventitious contact sites, and selecting a mutagenized eglin c comprising at least one non-naturally occurring amino acid in an adventitious contact site which inhibits a protease. In some embodiments, the mutagenized eglin c selectively inhibits the protease; in other embodiments, the mutagenized eglin c specifically inhibits the protease.

The present invention also provides a method for producing a protease inhibitor that is an eglin c variant comprising at least one non-naturally occurring amino acid in an adventitious contact site, and further comprising at least one non-naturally occurring amino acid in a reactive loop, where the method comprises providing a modified eglin c comprising at least one non-naturally occurring amino acid in a reactive loop, randomly mutagenizing selected adventitious contact sites, and selecting a mutagenized modified eglin c comprising at least one non-naturally occurring amino acid in an adventitious contact site which inhibits a protease. In some embodiments, the mutagenized modified eglin c selectively inhibits the protease; in other embodiments, the mutagenized modified eglin c specifically inhibits the protease.

The present invention further provides an affinity resin, comprising a protease inhibitor that is an eglin c variant as described above. The present invention also provides a method of purifying proteases, comprising providing an affinity resin comprising a protease inhibitor that is an eglin c variant as described above, and using the resin to purify a protease.

DESCRIPTION OF THE FIGURES

FIG. 1 shows a synthetic eglin c gene of 231 bp (SEQ ID NO: 1), and the amino acid sequence encoded by the gene (SEQ ID NO: 2). This gene encodes Arg45 in place of Leu45 (Arg45-eglin c), and utilized the high abundance *E. coli* codons, which were used to design a synthetic nucleotide sequence for Arg45-eglin. NdeI, NcoI and BamHI sites were designed for cloning into the pET27b(+) vector. AatII and BglII sites were introduced for cassette mutagenesis of the reactive site loop. For protein expression, the AatII site was silenced by mutating CGA to CGT for the Arg45 (P1 position). The N-terminal three amino acid residues (MSM) differ from that (TGF) of the naturally occurring eglin c. Target residues for site-directed mutagenesis, Gly40(P6), Pro42 (P4), Thr44 (P2), and Leu45 (P1), are indicated in bold and are underlined. Note that the amino acid sequence shown has the amino acid sequence in the reactive site loop and at adventitious contact sites of wild-type eglin c.

FIG. 2 shows a 96-well, 0.45 $\mu$m GHP (Gelman hydrophilic polypropeylene; manufactured by Gelman, Inc., Ann Arbor, Mich.) membrane filter plate containing cultures of individually transformed *E. coli* BL21(DE3) cells into which libraries were introduced.

FIG. 3 shows results from a rapid screening of the library described in Example 2.7, using Kex2 (panel A), furin (panel B), and human PC7, another mammalian furin homologue (panel C).

FIG. 4 shows the correlation of inhibition ratios of Kex2 and furin (panel A) and of PC7 and furin (panel B) by Y$_{49}$X-eglin variants.

FIG. 5 shows the sequences spanning the mutated sites in genes obtained in the screen (SEQ ID NOS: 3–24); the mutated sites are underlined. The non-mutated nucleic acid sequences are the same as that shown in FIG. 1; the location of the mutation in the sequence shown in FIG. 1 can thus be determined by aligning the non-mutated nucleic acid sequences in each sequence with the nucleic acid sequence shown in FIG. 1.

Figure 6:
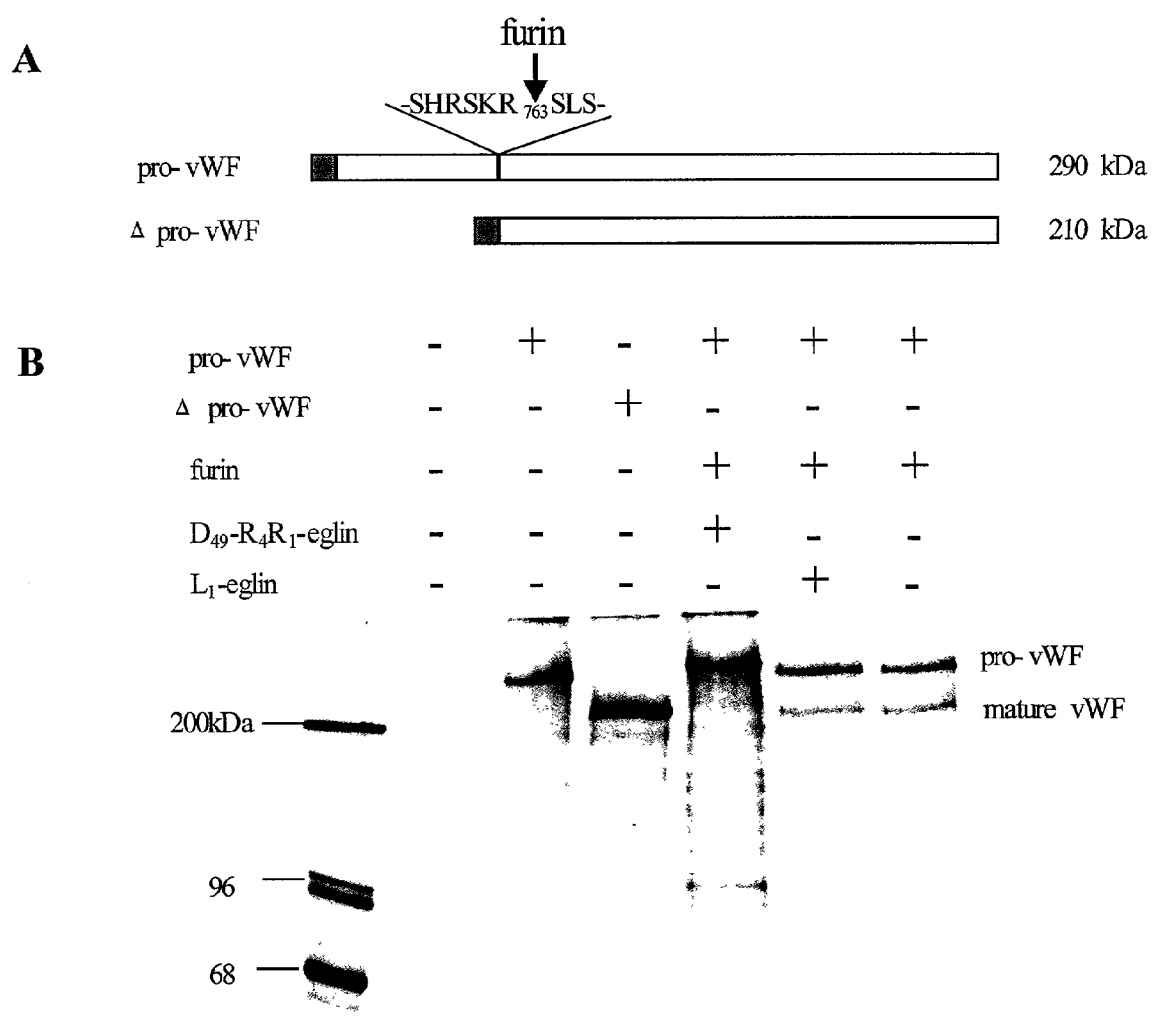

FIG. 6 shows furin dependent processing of von Willebrand factor (vWF) in COS-1 cells in the presence and absence of Asp49-R4R1-eglin. Panel A shows schematic representations of pro-vWF and mature vWF (Δ-pro vWF, where the Δ refers to deletion of the pro domain which is cleaved by furin during processing and maturation of vWF). Panel B shows the experimental results as analyzed by SDS-PAGE. After a pulse-labeling and a 6 hour chase, cell extracts were prepared with NP-40 lysis buffer, subjected to SDS-PAGE, and analyzed by autoradiography. Lane 1, mock transfection; lane 2, pro-vWF transfection; lane 3, δ-pro-vWF (lacking pro-domain of vWF) transfection; lanes 4 to 6, furin and vWF co-transfection. At 4 hours prior to the pulse-radiolabel, Asp49-R4R1-eglin was added into the conditioned medium for lane 4, and wild type eglin (Leu at P1) was added to the conditioned medium for lane 5; neither eglin was added to the conditioned medium as a control (lane 6).

DEFINITIONS

To facilitate an understanding of the present invention, a number of terms and phrases as used herein are defined below:

The terms "proprotein convertase," "PC" and "proprotein processing protease" refer to members of a family of endoproteases which are homologous with bacterial subtilisins and yeast Kex2p; proprotein convertases catalyze limited endoproteolysis of inactive precursor proteins at sites marked by paired or multiple basic amino acids, resulting in production of biologically active peptides and proteins in eukaryotic cells. Members of this family include naturally occurring enzymes, as well as mutant and modified enzymes, and synthetic enzymes.

The term "kexin" and "Kex2" refer to the protein product of the yeast *Saccharomyces cerevisiae* gene (EC 3.4.21.61). Kexin has a catalytic domain showing sequence similarity to bacterial serine proteases belonging to the subtilisin family.

The term "furin" refers to the first proprotein convertase to be identified (EC 3.4.21.85). Furin is capable of cleaving precursors of a wide variety of proteins, including growth factors, serum proteins, including proteases of the blood-clotting and complement systems, matrix metalloproteinases, receptors, viral-envelope glycoproteins and bacterial exotoxins, typically at sites marked by the consensus Arg-Xaa-(Lys/Arg)-Arg sequence.

The term "additional proteases of the present invention" refers to proteases which recognize amino acids on the P side of a scissile bond; typically, such enzymes are endopeptidases, and may be encoded by a host or by a pathogen. Examples include but are not limited to capase, for which amino acids in the P1 and P4 positions are important for substrate recognition.

The term "eglin c" refers to a polypeptide protease inhibitor from the leech *Hirudo medicinalis*. The term "native eglin c" refers to an eglin c protein which has a native reactive site loop and adventitious contact sites. The gene for a native eglin c may be a synthetic gene which is optimized for expression in different host cells, based upon host cell codon usage. Eglin c is referred to variously as "eglin c", "eglin-c" and "eglin".

The term "reactive site loop" refers to an extended active site binding loop, which flanks the hydrophobic core of eglin c on the other side from the a-helix and is exposed. The reactive site binding loop is highly complementary to the active site region of the target enzyme, and closely resembles the conformation of a peptide substrate when bound to the enzyme. The reactive site loop consists of residues 40 to 48 (numbering from the amino terminal), and contains a scissile mimetic peptide bond between Leu45 (P1) and Asp46 (P1). The reactive site loop is also referred to as the "reactive site loop" or "reactive binding loop" or "reactive binding site loop" or "binding loop" or the like.

The term "scissile bond" refers to a site of cleavage in a protein substrate which can be cleaved by an endopeptidase. It is thus an amino acid sequence which is recognized by a protease and capable of being cut or cleaved by the protease. The term "scissile mimetic bond" refers to a sequence of amino acids which resembles a scissile bond, but which isn't cleaved by a protease; this sequence thus "mimics" a scissile bond.

The term "adventitious contact site" or "adventitious interactions" refer to points of contact between an enzyme and an inhibitor, exclusive of the interactions between the substrate binding site (enzyme) and reactive site loop (inhibitor). Such contacts include incidental interactions believed to occur because the enzyme and substrate did not coevolve.

The term "random mutagenesis" refers to randomization of the codons encoding any particular amino acid residue, such that a different amino acid becomes encoded by the mutagenized codon. Thus, the mutagenesis is not directed toward a particular amino acid.

The term "inhibitor" or "inhibit" when used in reference to a protease, and in particular to a proprotein convertase or a proprotein processing protease, refers to a decrease in enzyme activity towards its substrate in the presence of the inhibitor which results in the inhibition.

The term "affinity" is used to describe the strength of the interaction between the inhibitor and an enzyme. Typically, either (i) an equilibrium dissociation constant (KD) or inhibitor constant (KI) is used (these are equivalent; higher affinity is indicated by numerically smaller values) or (ii) an equilibrium association constant (Ka) is used (higher affinity is indicated by numerically larger values; this is the reciprocal of the KD). "Specificity" refers to the degree of inhibition effected by a specific inhibitor for a specific enzyme or class of enzymes; the greater the degree of inhibition, the greater the degree of specificity. Thus, "specificity" describes the relative reactivity of an enzyme with two substrates. This is quantified as the ratio of kcat/KM of an enzyme for the two substrates, as described in Fersht, A. R. (1985) in Enzyme Structure and Mechanism (W. H. Freeman and Co., New York) pp. 105 & 112. "Selectivity" refers to the difference in degree of inhibition, or specificity, effected by a particular inhibitor for different enzymes; the greater the degree of inhibition effected for a particular enzyme, or class of enzymes, relative to other enzymes or class of enzymes, the greater the selectivity the inhibitor exhibits for that particular enzyme or class of enzymes. Such an inhibitor "selectively inhibits" or is a "selective inhibitor" for that particular enzyme or class of enzymes. The term "selectivity" thus describes the relative affinity of a specific inhibitor for two different enzymes. This is quantified by a selectivity ratio: the ratio of the Ka values for two inhibitors. This gives information about the relative affinity of a single inhibitor for two different enzymes.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "patient" refers to an individual acutely infected with an infectious agent; preferably, the infectious agent is a bacteria, virus, or fungus, resulting in a disease, where disease progression is dependent upon a proprotein processing convertase or similar enzyme. A patient is also an individual suffering from a disease caused by an endogenous proprotein convertase enzyme disfunction. A patient is any type of animal, including mammals, and preferably is a human.

The term "therapeutically effective amount" refers to the amount of an eglin c variant of the present invention which prevents and/or ameliorates symptoms of a disease. A therapeutically effective amount is an amount which renders a beneficial effect on the initiation and/or progress of the disease resulting from an infectious agent. In acute infections, the amount preferably is sufficient to attenuate the virulence of the infectious agent for a period of time sufficient to allow the host immune system to overcome the infectious agent and/or or to allow another therapy to overcome the infectious agent. In situations of exposure to an infectious agent, the amount preferably is sufficient to prevent and/or attenuate the virulence of the infectious agent for a period of time sufficient to allow the host immune system to overcome the infectious agent and/or to allow another therapy to overcome the infectious agent.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. When used in reference to eglin c, the related polypeptide has the amino acid sequence in the reactive site loop and at adventitious contact sites of wild-type eglin c, as is shown in FIG. 1. The variant may have "conservative" changes, wherein a substituted amino acid has similar structural or chemical properties. One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences.

The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5× SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining.

Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6–16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "wild-type" or "native" when made in reference to a gene refers to a gene which has the characteristics of a gene isolated from a naturally occurring source. The term "wild-type" or "native" when made in reference to a gene product refers to a gene product which has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A "naturally-occurring" amino acid in a protein, polypeptide, or peptide is any amino acid which exists in a particular position in the amino acid sequence in a naturally occurring protein, polypeptide, or peptide. A "non-naturally occurring" amino acid in a protein, polypeptide, or peptide is any other amino acid which does not exist at that particular position in the amino acid sequence in the naturally occurring protein, polypeptide, or peptide. Examples of non-naturally occurring amino acids include but are not limited to amino acid insertion and amino acid substitution or replacement. Non-naturally occurring amino acids include any of the twenty standard amino acids as well as unusual amino acids and synthetic amino acids.

A wild-type gene is that which is most frequently observed in a population and is thus arbitrarily designated the "native" or "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al.

[1989] *Molecular Cloning: A Laboratory Manual*, Cold Spring Harbor Press, NY, pp 9.31–9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39–7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabelled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

GENERAL DESCRIPTION OF THE INVENTION

The present invention relates to novel eglin c variants which inhibit proprotein convertases, and in particular to eglin c variants with mutations at adventitious contact sites for treatment of diseases including acute bacterial and viral infections.

The presently claimed invention comprises novel eglin c variants and nucleic acid sequences encoding these variants, compositions comprising such novel eglin c variants and nucleic acid sequences encoding these variants, and methods of producing and of using such eglin c variants, nucleic acid sequences, and compositions. The present invention also comprises methods of developing novel eglin c variants, and of screening the effectiveness/inhibitory selectivity and specificity of such variants.

Proprotein convertases (PCs) are endopeptidases which cleave protein substrates at specific cleavage sites within the substrate. The site of cleavage in the protein substrate is known as a scissile bond. Endopeptidases have a large active site, typically about 25 Angstroms long, within which are several subsites, typically 6–8, each of which accommodates a single amino acid residue of the protein substrate. The subsites are located on both sides of the catalytic site, and typically 3 to 4 subsites are located on each side. The subsites are numbered according to the amino acid residue and its location relative to the scissile bond of the protein substrate which the subsite accommodates, and are designated by a "S." The amino acid residues are numbered correspondingly, with a designation of "P." Thus, for example, subsites are numbered from S1 to S4 on the amino terminal side of the scissile site, with the number 1 indicating a subsite adjacent to the catalytic site, and the amino acid residues are numbered correspondingly from P1 to P4. Subsite S1 accommodates P1, and so on. On the carboxy terminal side of the scissile bond, the subsites are numbered from S1' to S4', and the protein substrate amino acid residues are numbered correspondingly P1' to P4'. This information regarding P residues and S subsites is a generic means of classifying protease interactions with substrate residues near the active site and was originally published in Schechter, I., & Berger, A. (1967) Biochem. Biophys. Res. Commun. 27: 157–162.

Proprotein convertases refer to subtilisin-related proprotein processing enzymes homologous to kexin (KEX2 gene product, also referred to Kex2), expressed in the yeast *Saccharomyces cerevisize*, and to furin, a mammalian enzyme. There are seven kexin/furin-related genes currently known in humans and other mammals: furin, PC1 (also referred to as PC3 or PC1/3), PC2, PC4, PACE4, PC6 (also referred to as PC5) and PC7 (also referred to as PC8, aka LPC). These enzymes generally share the following characteristics: (i) a high degree of sequence specificity in substrate recognition that involves recognition of clusters of basic residues, typically of the form Arg-Xaa-Lys/Arg—Arg-↓; (ii) roles in specific proprocessing in late secretory compartments (trans Golgi network or secretory granules or vesicles) as opposed to being involved in protein degradation; (iii) the presence of distinct patterns of conserved residues near active site residues; (iv) a high degree of conservation within the core subtilisin domain (~45 to 50% between the yeast and mammalian enzymes); and (v) the conservation of the ~150 residue P-domain which is essential for function in the processing enzymes but which is not found in the degradative subtilisins. Several reviews may be consulted for additional information (see, for example, Zhou A et al. (1999) J. Biol. Chem. 274 (30): 20745–8; and Fuller, R. S. (1998) in Handbook of Proteolytic Enzymes (A. J. Barrett, N. D. Rawlings & J. F. Woessner (eds.), Academic Press (England)) p. 342–345).

Due to the hypothesized important role of PCs in a variety of different types of diseases, several attempts have been made to develop drugs based upon inhibition of these enzymes. Inhibitors can be (i) small molecules which may or may not be peptides or peptide mimetics or (ii) proteins. Protein inhibitors of proteases typically are natural products that evolved to inhibit specific target proteases for a physiological reason. Such inhibitors can be endogenous or exogenous. For example, anti-thrombin III is an endogenous inhibitor of the blood clotting enzyme thrombin and thus acts as an anticoagulant. Eglin c is an exogenous inhibitor of elastase: It is produced by a leech and introduced into the parasitized target organism to block the activation of an inflammatory response induced by elastase, a protease in the host organism.

One inhibitor-based approach was directed toward the utilization of peptidyl chloromethane (aka peptidyl chloromethylketone) inhibitors. However, biological and pharmaceutical applications of this type of inhibitor are limited, due to toxicity of the compound (Angliker et al. (1993) Biochem. J. 293: 75–81). Another approach is directed to the utilization of ovomucoid third domain inhibitors engineered for inhibition of processing proteases. However, these molecules exhibit a relatively low affinity for furin (Lu et al. (1993) J. Biol. Chem. 268: 14583–14585).

Yet another approach involved the use of kexstatin, a proteinaceous inhibitor of microbial origin which belongs to *Streptomyces* subtilisin inhibitor family (SSI) and which was reported to be a potent Kex2 inhibitor. However, kexstatin has Lys at P1, suggesting that it is likely to be a less potent inhibitor of furin or Kex2 than a mutant of eglin c, R4R1-eglin described below. Indeed, no affinity constant has been published (Oda et al. (1996) Biosci. Biotechnol. Biochem. 60: 1388–1389; and Shibano et. al. (1999) U.S. Pat. No. 5,952,463). Unlike eglin c, ovomucoid third domain and Kexstatin both have Cys at the P3 position, a feature that may decrease the affinities of these inhibitors.

Another approach was directed toward utilization of a1-Antitrypsin Portland (a1-PDX), which is a potent, specific furin inhibitor. (Jean et al. (1998) Proc. Natl. Acad. Sci. U.S.A. 95: 7293–7298; Thomas et. al. (1997) U.S. Pat. No. 5,604,201; and Thomas et. al. (2000) U.S. Pat. No. 6,022,855). a1-PDX is derived from the natural elastase inhibitor, a1-antitrypsin (a serpin, also known as a1-proteinase inhibitor), in which the P1 and P4 positions (Met and Ala, respectively) have been mutated to Arg. It is believed that additional substitutions, such as Arg for Leu at P6 position in a1-PDX, might impair the unique serpin inhibition mechanism, which requires a dynamic conformational change. The conformational change in the serpin reactive site loop involves insertion of the loop into a beta sheet resulting in burial of the P6 Leu side chain. The strong positive charge of the Arg side chain would make burial highly unfavorable. The native forms of serpins are unstable, and are susceptible to hydrolysis by enzymes which are not inhibited. In addition, serpins are large molecules (350 amino acids) whose large scale production presents difficulties. It has been reported that two molecules of a1-PDX inhibit one molecule of furin, forming an irreversible complex, although other serpins are known to form 1:1 complexes. The nature of this 2:1 complex is unclear. Moreover, the reactive site loop of a1-PDX is cleaved by furin, thus destroying the inhibitor.

Yet another approach was directed toward utilizing eglin c as inhibitors of PCs. Eglins are small serine proteinase inhibitors isolated from the leech *Hirudo medicinalis*. They consist of a single polypeptide chain of 70 amino acids long, and are members of the serine proteinase inhibitor of the potato I family. Eglin b and c differ by a single amino acid at position 35 (His versus Tyr, respectively), and they are both potent inhibitors of the serine proteinases subtilisin, chymotrypsin, elastase, and cathepsin G. Although they lack disulfide bridges, eglins are very resistant to heat and acid denaturation.

The gene encoding eglin c has been isolated and cloned, and quantities of the protein are easily produced. Eglin c is a wedge shaped molecule, consisting of essentially two parts: a hydrophobic core, consisting of a twisted mixed parallel and antiparallel four-stranded B-sheet and flanked on one side by an a-helix; and an extended active site binding loop (or reactive site loop or reactive binding loop or reactive binding site loop), which flanks the core on the other side from the a-helix and is exposed. The reactive site binding loop is highly complementary to the active site region of the target enzyme, and closely resembles the conformation of a peptide substrate when bound to the enzyme.

The binding loop consists of residues 40 to 48 (numbering from the amino terminal), and contains a mimetic scissile peptide bond between Leu45 (P1) and Asp46 (P1'). (The bond between the P1 and P1' residues in the reactive site loop is referred to as a "scissile mimetic" bond because the best eglin c-derived inhibitors are not cleaved by Kex2 or furin.) In contrast to most other serine proteinase inhibitors, the eglin c binding loop is stabilized exclusively by non-covalent interactions in which two protruding core arginines (Arg51 and Arg53) and two binding loop residues flanking the scissile bond (Thr44 and Asp46) are involved. (Hipler et al. (1996) Adv Exp Med Biol 379: 43–47). The position of the binding loop relative to the core of eglin c is apparently pliant, becoming fixed only upon complex formation with its target enzyme. This broadens the inhibitory specificity of eglin c toward serine proteases, as the partly flexible reactive site, which is not fixed by disulfide bridges, can adapt to slightly different active sites (Heinz et al. (1991) J. Mol. Biol. 217: 353–371). On the other hand, the binding loop of eglin c is relatively fixed in a rigid conformation when compared to the more flexible peptide substrate, which prevents the binding loop from being cleaved at its "scissile bond." X-ray crystallographic studies indicate an induced fit of the eglin binding loop to the active site cleft of the target enzyme upon complex formation. Moreover, the inhibitory potency of eglin c decreases with apparently decreasing core-binding loop interactions (Hipler et al. (1996) Adv Exp Med Biol 379: 43–47).

Variants of eglin c have been reported, which contain one of the following: 1) A truncated N-terminal of four or six residues; and 2) Substitutions of Arg, Met, Lys, Phe, and Trp at P1, substitutions of Pro and Ser at P2, and substitutions of Ser, Glu, Gln, Ala, and Thr at P1' (Heinz et al (1991) J. Mol. Biol., 217: 353–371; Seemüler et al. (1987) U.S. Pat. No. 4,636,489; Grütter et al. (1992) U.S. Pat. No. 5,079,229; Grütter et al. (1993) U.S. Pat. No. 5,180,667). These reported recombinant eglin c variants possessed an acetylated N-terminal, and direct N-terminal sequencing was therefore not possible. Moreover, these variants did not have any amino acid substitutions at P6, P4, and P4' positions, which have been surprisingly discovered by the present inventors to be of importance for processing protease specificity.

The present invention provides a new family of genetically engineered inhibitors of PCs (also referred to as proprotein processing proteases), which is based on eglin c, a polypeptide protease inhibitor from the leech *Hirudo medicinalis*.

Eglin c offers several advantages as a template for building new inhibitors. A very important one is that because eglin c is derived from the saliva of the medicinal leech, *Hirudo medicinalis*, it is likely to be non-immunogenic in humans, as the leech has co-evolved with mammalian hosts so as to avoid causing a reaction. This is the case with the leech derived thrombin inhibitor, Hirudin, a variant of which has successfully passed through clinical trials as an anticoagulant.

Another important advantage is that eglin c is a member of the potato inhibitor family, and like most members of this family (Laskowski, M. Jr., and Kato, I. (1980) Ann. Rev. Biochem. 49: 593–626; Seemüller, U. et al. (1986) in Proteinase Inhibitors, (Barret, A. J. and Salvesen, G. Ed.) pp. 336–359, Elsevier, Amsterdam); and Bode, W., and Huber, R. (1992) Eur. J. Biochem. 204: 433–451), lacks disulfide bonds. This is in contrast to inhibitors of the Kunitz family (e.g., BPTI) or the Kazal (ovomucoid) family (Greagg, M. A. et al. (1994) Biochim. Biophys. Acta 1222: 179–186), and appears to facilitate robust expression of eglin c. Another advantage is that eglin c is thermostable (TM~86° C.) (Bae, S.-J., and Sturtevant, J. M. (1995) Biophys. Chem. 55: 247–252), despite its small size (70 a.a.) and the absence of disulfide bonds. Yet another advantage is that eglin c is a potent inhibitor of degradative subtilisins. Yet another advantage is that eglin c variants form a reversible stoichiometric complex with either Kex2 or furin, and the reactive site loop of eglin is not cleaved, but remains intact (Komiyama & Fuller (2000) Biochem 39:15156–15165); this is in contrast to a1-PDX, which forms an irreversible complex with furin, and in which the reactive site loop is cleaved by furin. Finally, eglin c is believed to have a flexible reactive site loop (based on NMR studies of members of the potato inhibitor 1 family, which have shown that these inhibiors have relatively flexible reactive site loops), and the presence of these loops may increase the ability of eglin c-based inhibitors to adapt to distinct structural features of the catalytic binding regions of new target enzymes (Li, A., and V. Daggett, V. (1995) Protein Engineering 8: 1117–1128; Hyberts, S. G. et al. (1992) Protein Sci. 1: 736–751).

Thus, attempts were made to incorporate directed sequence alterations within the eglin c reactive site loop, in an effort to create inhibitors that would dock well with the subtilisin-related processing enzymes (Komiyama et al. (2000) Biochem 39: 15156–15165). The catalytic domains of the kexin/furin processing proteases are homologous to the degradative subtilisins and, as a result, broad features of substrate recognition are conserved between both types of enzymes, even though specificity, per se, is not. The processing enzymes conserve the propensity, found in degradative subtilisins, to recognize the P1, P2 and P4 residues of substrates (Grøon, H. et al. (1992) Biochemistry 31: 6011–6018; Grøon, H., and Breddam, K. (1992) Biochemistry 31: 49–53). However, the nature of recognition at the sites differs markedly. The degradative enzymes exhibit generic specificity, tending to prefer hydrophobic residues at P1 and P4 and small residues at P2. In contrast, Kex2 and furin tend to prefer basic residues at these positions. The two enzymes exhibit high selectivity for Arg at P1 (100- to 10,000-fold) (Brenner, C., and Fuller, R. S. (1992) Proc. Natl. Acad. USA 89: 922–926; and 4747; Rockwell, N. C. et al. (1997) Biochemistry 36, 1912–1917.). Kex2 also exhibits stringent selection for the P2 side chain (Lys or Arg) and a less, but still measurable, selectivity for the P4 residue (basic or aliphatic) (Rockwell, N. C. et al. (1997) Biochemistry 36, 1912–1917; Rockwell, N. C., and Fuller, R. S. (1998) Biochemistry 37: 3386–3391.). In contrast, furin exhibits stringent specificity for Arg at P4 and more relaxed specificity for a basic residue at P2 (Watanabe, M. et al. (1995) J. Virology 6:, 3206–3210; Krysan, D. J. et al. (1999) J. Biol. Chem. 36: 23229–23234; and Watanabe, T. et al. (1993) FEBS Lett. 320: 215–218). In addition, furin is selective for Arg at P6 (Watanabe, M. et al. (1995) J. Virology 6:, 3206–3210; Krysan, D. J. et al. (1999) J. Biol. Chem. 36: 23229–23234; and Watanabe, T. et al. (1993) FEBS Lett. 320: 215–218), whereas Kex2 is indifferent to the P6 residue (Krysan, D. J. et al. (1999) J. Biol. Chem. 36: 23229–23234).

In designing sequence alterations within the eglin c reactive site loop, substitutions were introduced into the reactive site loop of eglin c at the P1 (Leu45), P2 (Thr44), P4 (Pro42) and P6 (Gly40) positions (Komiyama et al. (2000) Biochemistry 39: 15156–15165). Ten reactive site variants were generated by cassette mutagenesis of a synthetic eglin gene which had Arg at P1. A "wild-type" eglin c with Leu at P1 was created to serve as a control. Several of the engineered eglin c variants were found to bind tightly and form stable, reversible complexes with both Kex2 and furin at a stoichiometry of 1:1.

As described below, the substitutions made in eglin at P2 and P6 represented attempts to generate even higher-affinity inhibitors for furin and Kex2, but these substitutions did not have the desired effects. Substitutions at P1, P2, P4 and P6 within the reactive site loop exhausted the possibilities to optimize substrate-like contacts between eglin c and the processing proteases. Surprisingly, it has now been discovered that non-reactive site loop variants of eglin c are also effective as inhibitors of PCs.

Thus, the present invention provides novel eglin c variants which are improved inhibitors of PCs, based upon optimizing adventitious interactions between the enzyme and an eglin c-based inhibitor at positions lateral to the active site/reactive site loop interface, resulting in non-reactive site loop variants of eglin c. Such improved inhibitors have optimized adventitious contact sites.

The present invention also provides methods of developing such improved eglin c-based inhibitors of PCs, based upon identifying adventitious sites which can be optimized by screening variants produced by randomly mutagenizing specific selected amino acid residues in the eglin template outside the reactive site loop. A variant with at least one optimized adventitious contact site combined with at least one optimized reactive loop site results in an inhibitor that exhibits affinities up to 15-fold higher than that seen in a variant with the optimized reactive site alone. Combining optimized advantageous contact sites can produce even higher affinities. As noted, different members of the family of human processing enzymes exhibit rather similar specificities at P1, P2 and P4. Thus, the present invention further provides highly selective, high affinity inhibitor molecules that are selective for each of these different enzymes, and methods for producing the same, based upon randomly mutagenizing adventitious contact sites.

The eglin c variants with at least one optimized adventitious contact site combined with at least one optimized reactive loop site provides several advantages over PC inhibitors currently available. For example, in contrast to peptidyl chloromethane, which have toxicity concerns, the eglin c variants of the present invention have low toxicity. The eglin c variants of the present invention also have higher affinities for furin than do ovomucoid inhibitors and kexstatin. Kexstatin also has Lys at P1, suggesting that it is likely to be a less potent inhibitor of furin or Kex2 than an eglin c variant R4R1-eglin, described below. In contrast to a1-PDX, which forms irreversible complexes with furin and in which the reactive site loop is cleaved by the protease, eglin c variants of the present invention form reversible stoichiometric complexes with either Kex2 or furin, and the reactive site loop of eglin c variants is not cleaved. And in contrast to the eglin c modifications reported by Ciba-Geigy, in which the N-terminal was acetylated and direct N-terminal sequencing was not possible, all the eglin c variants of the present invention are not acetylated and could be sequenced, and therefore can be shown to have identical N-terminal sequences (Komiyama and Fuller (2000) Biochemistry, 39:15156–15165).

The present invention further provides nucleic acid sequences encoding the novel eglin c variants described above, as well as vectors and host cells comprising such nucleic acid sequences, as well as methods of using the same.

The invention also provides methods of using the novel eglin c variants described above in the treatment of bacterial, viral, and fungal diseases. Such treatment is based upon the inhibition of bacterial protoxin maturation, the inhibition of viral envelope glycoprotein maturation, and the inhibition of fungal growth by the improved inhibitors of the present invention. The eglin c variant inhibitors are preferably utilized in treatment of acute disease, and they are administered to a patient in need of such treatment by any number of methods. The invention also provides methods for screening the improved eglin c based inhibitors for their effectiveness in treating bacterial, viral, and fungal diseases.

The invention also provides methods of using the improved inhibitors described above as reagents for general biological applications. Such applications include but are not limited to use as affinity purification reagents, use as a fluorescence tags, as for example for identification of cells containing target proteases, for subcellular localization of proteases, and for tracking internalization of drugs, and use for examining physiological functions of processing or other proteases in cell cultures or in transgenic animals, as for example by selectively inhibiting the enzymes.

I. Methods of Developing Improved Inhibitors of PCs

A. First Generation Eglin c Variants: Reactive Loop Site Variants

A first generation of eglin c variants were created by site-directed mutagenesis in the reactive site loop. The reactive site loop is the primary site of contact between PC inhibitors and the target enzyme. The first generation variants contained amino acid substitutions in the reactive site loop; certain substitutions resulted in increased affinity between the variant and processing proteases.

The creation of first generation of eglin c variants is exemplified in Example 1 and as reported by Komiyama and Fuller (2000) Biochemistry, 39:15156–15165.

1. Characterization of First Generation Eglin Variants

The parent eglin c construction was based on a synthetic eglin c gene optimized for E. coli codon usage and based upon a published DNA sequence of eglin c (55 and 53; see FIG. 1). Consistent with this, expression of all eleven eglin c variants using the pET vector system resulted in extremely high yields of the recombinant proteins. Unexpectedly, although the constructs did not incorporate a secretory signal peptide, the eglin c variants were quantitatively recovered from the cells by osmotic shock. Eglin c polypeptides were passed through Q-Sepharose to remove nucleotides and nucleic acids and subjected to ion-exchange chromatography on S-Sepharose, yielding homogeneous product as judged by SDS-PAGE, isoelectric focusing PAGE, N-terminal sequence analysis, and MALDI mass spectrometry (Example 1, Table 1). Substitutions of positively charged residues in the reactive site loop of individual eglin c variants had the predicted effects on pI. TUG-PAGE analysis showed that all variants remained folded, like eglin c itself, in urea concentrations up to ~8 M. The concentration of the active form of the inhibitors was determined by titration with active-site titrated proteases (Example 1). Equilibrium association constants for the interactions of the eglin variants with Kex2 and furin were determined (Table 2).

2. P1 and P4 Substitutions Create Eglin c Variants with High-Affinity for Furin and Kex2.

Genes encoding eglin variants with substitutions at the P1 and P4 positions were created, the variant proteins purified and their affinities for furin and Kex2 determined by examining inhibitory potency, as described in Example 1 (Table 2). The eglin c variants are referred by the substituted amino acid and the position at which it is substituted. Thus, R1-eglin refers to substitution of Arg at position P1. Substitution of a single Arg for Leu at P1, in R1-eglin, had little effect on furin affinity (2.5-fold increase) but resulted in a dramatic increase (104-fold) in affinity for Kex2. The additional substitution of Met for Pro at P4, resulting in M4R1-eglin, increased furin affinity 15-fold. However, once again, the substitution had a much larger effect on Kex2 affinity, increasing the $K_a$ 88-fold. Relative to L1-eglin (wild-type reactive site loop), M4R1-eglin exhibited $1.5 \times 10^6$-fold increased affinity for Kex2 but only 33-fold increased affinity for furin. Unlike Kex2, which appears to bind P4 basic and aliphatic residues with comparable affinity (Rockwell, N. C., and Fuller, R. S. (1998) Biochemistry 37: 3386–3391.), furin exhibits a high degree of selectivity for Arg at P4 (Krysan, D. J., Rockwell, N. C., and Fuller, R. S. (1999) J. Biol. Chem. 36: 23229–23234). Indeed, substitution of Arg for Met at P4 in M4R1-eglin, creating R4R1-eglin, substantially increased affinity for furin (1430-fold), but only slightly altered Kex2 affinity (2.5-fold decrease). Overall, R4R1-eglin exhibited a $4.6 \times 10^4$-fold higher affinity for furin than L1-eglin. High-affinity binding of R4R1-eglin to furin involves highly cooperative binding of the P1 and P4 Arg residues because, as shown in Table 2, the presence of Arg at only P1 (mentioned above) or at P4 (in R4L1-eglin) resulted in only a 2- to 3-fold enhancement of affinity relative to L1-eglin. Kex2, on the other hand, exhibited high affinity for eglin with Arg at P1 alone but substitution of Arg alone at P4 (Table 2) only slightly increased affinity (5-fold).

Although the two enzymes exhibited distinct patterns of inhibition by this set of eglin variant molecules, both enzymes exhibited a high degree of affinity ($K_i$ ca. $10^{-9}$ M) for eglin variants with appropriate substitution at just the P1 and P4 sites. In order to examine the stability and stoichiometry of complexes formed between P4P1 variant eglins and Kex2 and furin, enzyme-inhibitor mixtures were analyzed by native and denaturing PAGE. The results indicated that a stoichiometric complex of Kex2 and M4R1-eglin formed after a 15 min preincubation. This complex migrated more rapidly than either molecule alone, indicating a significant decrease in pKa upon complex formation. In SDS-PAGE, the complex dissociated into free protease and intact inhibitor. Complexes formed between stoichiometric amounts of Kex2 or furin and eglin variants were analyzed by SDS-PAGE after overnight incubation at room temperature. With the exception of those noted as temporary inhibitors in Table 2, all eglin variants remained intact after this treatment.

3. Substitution of Arg at P2 and P6 Results in Temporary Inhibitors of Furin

Both Kex2 and, to a lesser extent, furin, recognize basic residues at P2 (Bravo, D. A., Gleason, J. B. et al. (1994) J. Biol. Chem. 269: 25830–25837; and Rockwell, N. C. et al. (1997) Biochemistry 36: 1912–1917). In addition, furin interacts with Arg at P6 (Krysan, D. J. et al. (1999) J. Biol. Chem. 36: 23229–23234.). In an attempt to produce inhibitors of even higher affinity, Arg was introduced at P2 and P6. R6R4R1-eglin was made by substituting Arg for Gly40 in R4R1-eglin. R6R4R1-eglin was a temporary inhibitor of furin: significant activity was recovered about 15 min after Boc-Arg-Val-Arg-Arg-MCA (2 μM) was added to an enzyme-inhibitor solution. SDS-PAGE analysis coupled with N-terminal sequence analysis showed that recovery of activity was due to cleavage of the inhibitor carboxyl to the P1 Arg (Arg45). The $K_a$ of furin for R6R4R1-eglin could be determined during the initial inhibitory phase and did not differ significantly from the $K_a$ of furin for R4R1-eglin (Table 2). In contrast, R6R4R1-eglin formed a stable, stoichiometric complex with Kex2, again with an affinity similar to that of R4R1-eglin (Table 2).

Substitution at the P2 position resulted in molecules that exhibited temporary inhibition of both furin and Kex2. These three eglin variants, K2R1-, M4K2R1-, and R4K2R1-eglin, initially inhibited both proteases, but reactions exhibited a slow, positive deviation from linearity. Once again, temporary inhibition was shown by SDS-PAGE and N-terminal sequence analysis to be due to cleavage of the inhibitors after the P1 Arg (Arg45) and dissociation of the complex. $K_a$ values estimated from the linear part of reaction progress curves (Table 2) indicated that none of these eglin variants showed markedly increased affinity for either furin or Kex2.

4. Substitution of Lys at P1 Differentially Affects Eglin Affinity for Furin and Kex2

Two variants, R4K1-eglin and M4K1-eglin, were designed to examine the effect of substituting Lys for Arg at P1. Furin exhibited a 15.4-fold reduced $K_a$ with R4K1-eglin, relative to R4R1-eglin (Table 2) but only a 4.7-fold decreased $K_a$ with M4K1-eglin as compared to M4R1-eglin (Table 2). In contrast, Kex2 exhibited only a 2.8-fold decrease in $K_a$ with R4K1-eglin relative to R4R1-eglin but exhibited a larger, 13.2-fold decrease in $K_a$ with M4K1-eglin relative to M4R1-eglin (Table 2). Thus substitution of Lys for Arg at P1 had a greater effect on furin affinity when Arg was present at P4, but a greater effect on Kex2 affinity when Met was at P4. Taken together, the quantitative analysis of affinities of the eglin variants for furin and Kex2 show that the two enzymes responded quite differently to substitutions at the P1, P4, and P6 positions in the inhibitor.

5. Inhibitor Association and Dissociation Rates

In some aspects of the present invention, biological application of the eglin c variants of the present invention as inhibitors of processing in vivo depends upon the rate of binding to target enzymes, where it is critical. Therefore, the rate of action of eglin variants with Kex2 and furin was examined by incubating $5 \times 10^{-10}$ M enzyme with inhibitor at molar ratios of inhibitor to enzyme ranging from 10 to 80. Typical progress curves showed that M4R1-eglin was a slow, tight binding inhibitor of Kex2. A similar progress curve was observed for furin inhibition with the R4R1-eglin. The relationship between $k_{obs}$ and inhibitor concentration was linear. The values of $k_{on}$ were determined from the slope of such curves, and dissociation rate constants ($k_{off}$) were calculated ($k_{off} = k_{on}/K_a$). For R4R1-eglin, $k_{off}$ was calculated to be $2 \times 10^{-4} s^{-1}$ for Kex2, and $3 \times 10^{-4} s^{-1}$ for furin. Thus, the half-life ($t_{1/2}$) of the complex of R4R1-eglin with Kex2 and furin was estimated to be about 1 h. Similarly, the $t_{1/2}$ of the complex of M4R1-eglin with Kex2 was estimated to be 3 h. For complex of R4K1-eglin with furin, $k_{off}$ was calculated to be $2 \times 10^{-4} s^{-1}$ implying that the $k_{off}$ and $t_{1/2}$ for this complex are similar to those for the complex of R4R1-eglin with furin.

6. Inhibition of Other Serine Proteases by Eglin c Variants

L1-eglin inhibited subtilisin Carlsberg with a $K_a$ of $6.7 \times 10^{10}$ $M^{-1}$, human neutrophil elastase with a $K_a$ of $4.5 \times 10^{10}$ $M^{-1}$, and chymotrypsin with a $K_a$ of $1.1 \times 10^{10}$ $M^{-1}$ under our standard assay conditions. These $K_a$ values are consistent with those previously reported (Braun, N. J. et al. (1987) Biol. Chem. Hoppe-Seyler 368: 299–308; Heinz, D. W. et al. (1991) J. Mol. Biol. 217: 353–371; Ascenzi, P. et al. (1991) J. Mol. Recogn. 4: 113–119; Qasim, M. A. et al. (1997) Biochemistry 36: 1598–1607; and Lu, W. et al. (1999) Chem. and Biol. 6: 419–427). The substitution of Arg for Leu45 at P1 almost completely abolished elastase inhibition. However, R1-eglin retained inhibitory activity against trypsin ($K_a = 1.8 \times 10^{10}$ $M^{-1}$) and subtilisin Carlsberg ($K_a = 1.0 \times 10^{10}$ $M^{-1}$) with affinities similar to those previously reported (Heinz, D. W. et al. (1991) J. Mol. Biol. 217: 353–371; and Lu, W. et al. (1999) Chem. and Biol. 6:

419–427). Even though R4R1-eglin and M4R1-eglin were temporary inhibitors of trypsin, it was possible to determine $K_a$ values of $8.4 \times 10^9$ M$^{-1}$ and $4.4 \times 10^{10}$ M$^{-1}$, respectively, for the interaction of these two inhibitors with trypsin. M4R1-eglin inhibited subtilisin Carlsberg with a $K_a$ of $6.6 \times 10^{10}$ M$^{-1}$. Substitution of Arg at P4 in R4R1-eglin reduced affinity for subtilisin ($K_a$ of $6.5 \times 10^8$ M$^{-1}$). Thus, subtilisin, unlike Kex2 and furin, exhibits interactions with eglin c that are largely insensitive to the identities of the P1 and P4 residues. The eglin variants were also evaluated as inhibitors human plasma kallikrein and plasmin. R1-eglin exhibited weak inhibition of these plasma proteases with $K_a$ values in the range of $10^6$ M$^{-1}$.

7. Summary

Simple substitutions at P1 and P4, in the reactive site loop of eglin c, yield high affinity (in the nanomolar range) inhibitors of the processing proteases furin and Kex2. Several characteristics of these inhibitors make them particularly useful in a wide variety of applications. Like wild-type eglin c, the engineered molecules are small, stable proteins lacking disulfide bonds that are easy to express and purify in large quantities in bacterial cultures. In general, these inhibitors form stable, stoichiometric complexes with furin and Kex2 that do not undergo enzymatic turnover. Moreover, the complex of furin with R4R1-eglin is stable over a physiological pH range, from at least 6.0 to 7.4, suggesting that inhibitory complexes formed at the cell surface should remain intact after endocytic internalization.

Several of the eglin variants described above exhibit significant selectivity between the two processing proteases studied, furin and Kex2. Selectivity is evident in the differential effects of substitutions at P1, P4 and P6 in eglin c on the two enzymes. In the case of P1, for example, R4K1-eglin exhibited ~20-fold higher affinity for Kex2 than for furin; whereas, Kex2 bound R4R1-eglin only ~3-fold more strongly than furin did. The most striking case of selectivity was seen at P4, where Kex2 exhibited ~10,000-fold higher affinity for M4R1-eglin than did furin. A different kind of selectivity was observed at P6. Although introduction of Arg at P6 failed to result in significant enhancement of affinity for either enzyme, in the case of furin, R6R4R1-eglin was a temporary inhibitor; whereas, the same molecule formed a stable complex with Kex2.

Selectivity was also apparent in the degree of cooperativity observed in interactions with the P1 and P4 side chains. Previous studies of Kex2 and furin using small peptide substrates demonstrated energetic cooperativity between P1 and P4 (48, 51). Such cooperativity is evident in the interactions of both enzymes with the eglin variants, but is much greater in the case of furin where R4R1-eglin exhibited ~5.5 kcal/mol greater relative binding energy than would be predicted by the sum of the relative binding energies of R1-eglin and R4-eglin. (See table 2 in Komiyama, T. and Fuller, R. S. (2000) Biochemistry 39: 15156–15165).

The substitutions made in eglin at P2 and P6 represented attempts to generate even higher-affinity inhibitors for furin and Kex2, but these substitutions did not have the desired effects. Substitutions at P1, P2, P4 and P6 exhausted the possibilities to optimize substrate-like contacts between eglin c and the processing proteases.

Surprisingly, it was discovered that further improvements in affinity could be achieved by optimizing adventitious interactions between the enzyme and inhibitor at positions lateral to the active site/reactive site loop interface. Such optimization at adventitious contact sites may be made in native eglin c. Preferably, such optimization is made in eglin c variants with substitutions at P1 and P4 which exhibit high specific and selective inhibition of PCs. Thus, the first generation eglin c variants can be used as a platform for the development of second generation eglin c variants, resulting in eglin c variants which are PC inhibitors of even greater specific and selective inhibitory activity.

B. Second Generation Eglin c Variants: Adventitious Contact Site Variants

A second generation of eglin c variants were created by mutagenesis of non-reactive site loop sites. These variants, and the method used to produce them, as provided by the present invention and described below, are unexpectedly powerful.

This approach was based upon the observations that eglin c did not evolve to interact with proprotein processing enzymes of the Kex2/furin family, nor did it evolve to interact with degradative subtilisins, even though eglin c is found to be a high affinity inhibitor of such enzymes. Thus, the interaction of eglin c or eglin c variants with subtilisins and proprotein processing enzymes can be termed "non-orthologous". It was speculated that points of contact between an enzyme and an inhibitor exclusive of the interactions between the substrate binding site (enzyme) and reactive site loop (inhibitor) were unlikely to be optimal. These points of contact are referred to as "adventitious contact sites" as they are incidental interactions believed to occur because the enzyme and substrate did not co-evolve. It was further speculated that substitutions at such non-reactive loop sites might provide not only the possibility of obtaining inhibitors with increased affinity but also the possibility of creating inhibitors that display substantial differences in affinity for different proprotein processing enzymes. That is, eglin c variants could be developed to exhibit selectivity for individual proprotein processing enzymes. This approach is referred to as the "optimization of adventitious contacts," and it is an approach that is anticipated to be more generally applicable to the engineering of protease inhibitors and other proteins for non-orthologous interactions.

The optimization strategy involves five steps. First, eglin c residues outside of the reactive site loop, but with the potential to make contact with the target enzyme, are selected. Second, libraries are constructed within "template" genes that encode a native eglin c or one of the eglin c variants previously engineered within the reactive site loop at the P1 and P4 positions to interact with Kex2 and furin, as described above. Individual libraries are made by randomizing the codon for each "adventitious contact residue" using a partial randomization approach to decrease library complexity. Third, because the libraries are constructed in the context of an expression vector, the libraries can be introduced directly into the expression strain and clonal transformants can be grown in a 96-well format. Fourth, the use of 96-well filter plates makes it possible to both purify inhibitors expressed by the individual transformants in situ and to screen them for inhibitory potency against Kex2, furin and other enzymes using a 96-well fluorescence-based activity assay. Plotting these data as % inhibition in comparison to the control (i.e., the product of the template gene) allows identification of variants that exhibit increased or decreased affinity relative to the control. Correlation plots of data for two enzymes (e.g., Kex2 and furin) allow identification of inhibitors that exhibit selectivity between the two enzymes. Fifth, DNA sequences of promising variants are then determined, and the encoded inhibitors purified on a larger scale for further evaluation. Such evaluations include quantitative determination of affinity of inhibitors for Kex2, furin and other enzymes.

This approach is exemplified in Example 2. Candidates for amino acid substitution were selected by examining the crystal structure of the eglin c-subtilisin Carlsberg complex; those within 5 Angstroms of the surface were selected, resulting in ten candidates, as indicated in Table 4. Eight sites were subjected to limited randomization (see Table 5), and the effects of these amino acid substitutions on PC activity initially surveyed, as described in Example 2. The positions and identities of 19 substitutions found at the eight targeted positions are shown in Table 7. These novel variants were expressed and purified, and affinities for both Kex2 and furin were examined. At five targeted positions, the novel eglin c variants exhibited no significant enhancement of affinity for either Kex2 or furin. Substitution of Gly for Leu37 resulted in a minor effect on affinities for both Kex2 and furin. Substitutions for Glu39 exhibited enhanced affinity for furin, but they behaved as temporary inhibitors for these two enzymes. However, substantial enhancement of affinity at two targeted positions was found. These are Tyr49, and to a lesser degree, Val33.

Tyr49 emerged as a major site for optimization of affinity of eglin c (see Table 8). Novel eglin c variants at this position are referred to by the naturally occurring amino acid and the site which it occupies, followed by the non-naturally occurring amino acid which replaced it; the template from which the novel eglin c is derived is indicated following a hyphen. Tyr49Asp-R4R1-eglin, isolated in the initial survey of potential adventitious contact sites (in which only limited randomization was done), exhibited a 10-fold enhanced affinity for furin and a 16-fold enhanced affinity for Kex2. Position 49 corresponds to P4', a residue which has not been examined previously in studies of the specificity of either Kex2/furin processing proteases or degradative subtilisins. Ala and Cys substitutions for Tyr49 were also found using the rapid furin inhibition assay. The Ala substitution did not affect Kex2 affinity, but did increase furin affinity approximately 2-fold. The Cys variant appears to exhibit higher affinity for both enzymes, but accurate determination of affinities was difficult because the inhibitor purified as a monomer/dimer mixture.

Subsequently, the codon for Tyr49 was completely randomized, as described in Example 2 Section 7. The effects of these Tyr49Aaa eglin c variants (where Aaa represents any amino acid) on three enzymes, Kex2, furin, and human PC7, were then examined. More than 36% of the novel eglin c variants were better inhibitors of tested enzymes than the template from which they were derived, although 10% of the novel eglin c variant proteins were not inhibitors of these particular enzymes tested.

The inhibition pattern of Kex2, furin, and PC7 by the randomized Tyr49 eglin variants were distinct from each other, as shown in FIG. 3, indicating that the method of the present invention can be used to identify specific inhibitors for each member of the processing proteases. This figure shows the response of three enzymes, Kex2, furin and PC7 (a mammalian furin), to a set of eglin variants (more than 180) based on R4R1-eglin with random substitutions at codon 49. Note that the numbers on the x axis refer to individual inhibitors which are the same in each graph. The results shown in FIG. 3 show that for each enzyme there are inhibitors that are more effective against one enzyme than against the other two; such inhibitors are then selective for the enzyme for which they are more effective.

Correlation of inhibition ratios of each enzyme by the randomized Tyr49A-eglin variants are shown in FIG. 4. The most potent inhibitors are not necessarily selective between different members of the Kex2/furin family (for example, between furin and PC7), but potent inhibitors of each of tested enzymes which are also selective can be found. Thus, potent inhibitors of Kex2 also inhibit furin equally well (FIG. 4A). However, two species exhibited an inhibition ratio of ~0.2, or ~0.4 with furin, while exhibiting almost no inhibition of Kex2 (FIG. 4A). Considerably greater divergence was seen when furin inhibition ratios were plotted against PC7 inhibition ratios (FIG. 4B), suggesting that inhibitors that discriminate between PC7 and furin can be distinguished, and that PC7 has a rather unique specificity for the side chain position 49 in R4R1-eglin.

Several data points in FIG. 4 indicate the existence of inhibitors which exhibited a unique inhibition ratio to each member of the enzyme family that was tested. This is additional evidence that selective inhibitors can be obtained by this screening method. Thus, the method of the present invention, of randomization of adventitious contacts, can be used to find both potent, or specific, and selective, inhibitors of individual members of a protease enzyme family.

C. Screening Method for Potent, Specific Inhibitors for Proprotein Processing Enzymes The present invention also provides a novel screening method for potent, specific inhibitors for proprotein processing enzymes. It is simple, rapid, and a sufficiently comprehensive screening technology to be applicable to developing inhibitors of existing as well as other newly discovered proteoltyic enzymes. Kex2/furin family enzymes exhibit rather similar specificities at the primary side of substrate reactive site loop at P1, P2, and P4 position. The present invention provides a method directed to randomizing adventitious interactions between a protease and inhibitor residues both N-terminal and C-terminal to the scissile mimetic bond, to develop specific and selective inhibitors to each member of Kex2/furin, or PC, family of enzymes, as described previously. These methods are also applicable to developing specific and selective inhibitors to other proteolytic enzymes for which an eglin c, appropriately modified, can act as an inhibitor. The eglin c variants developed in accordance with the present invention can then be rapidly screened for their effectiveness as protease inhibitors by the screening method of the present invention, which is based upon the facts that the expressed eglin c variants are stable, and easy to express with resulting high yield.

In the screening method of the present invention, nucleic acid sequences encoding eglin c variants of the present invention in an expression vector under control of a promoter, preferably an inducible promoter, are cloned into appropriate host cells; preferably, the host cell is *E. coli*. Appropriate vectors and host cells are described in further detail subsequently. The cells are then cultured in a multiwell culture plate; preferably, the plate is a 96 well culture plate. The eglin c variants are expressed, preferably in response to an inducing agent, and cell extracts containing the expressed eglin c variants are assayed for the effects of the eglin c variant on protease activity. The extracts are crude or purified to different degrees; one or more proteases can be screened for each eglin variant. Illustrative but non-limiting examples are provided by Komiyama and Fuller (2000) Biochemistry 39: 15156–15165, which is hereby incorporated in its entirety.

In one embodiment of the screening method of the present invention, crude extracts of eglin variants are obtained from *E. coli* cultures grown in 96 well filter plates, induced for eglin expression, and subjected to osmotic shock after freeze thaw to release expressed eglin (as described in the Examples and Komiyama and Fuller (2000) Biochemistry 39: 15156–1515). Extracts diluted 50-fold in total 100 $\mu$L enzyme assay buffer are incubated with a battery of target enzymes in the presence of an appropriate fluorogenic peptide substrate for an appropriate length of time (e.g., 15 min) in 96-well format. Fluorescence is determined with a fluorescence micro titer plate reader, which is inexpensive and widely available. Those variants which reveal potent inhibition are selected and further characterized by DNA sequence analysis. The whole screening method requires about seven days after library construction. Selected eglin c variants are then expressed on a large scale (as described in the Examples and Komiyama and Fuller (2000) Biochemistry 39: 15156–15165).

Alternative embodiments comprise the use of chromogemc or other substrates of the target protease. Other substrates include the use of peptidyl para-nitroanilide substrates (chromogenic) such as Ala-Lys-Arg-pNA or other similar substrates, or internally quenched fluorescent substrates such as Arg-Glu(EDANS)-Pro-Met-Tyr-Lys-Arg↓Glu-Ala-Glu-Ala-Lys(DABCYL)-Arg (SEQ ID NO: 64) or Arg-Lys(DABCYL)-Xaa—Xaa—Xaa—Xaa↓Glu-Ala-Glu-Ala-Glu(EDANS)-Arg (SEQ ID NO: 65) (where Xaa represents any amino acid) (see, for example, Rockwell, N. et al. (1997) Biochem. 36:1912–1917), or other similar substrates. Any of these or similar substrates can be used to assay Kex2, furin or other Kex2/furin-related proprotein processing enzymes. Use of the internally quenched substrates is described in:

Yet other embodiments comprise the construction of libraries for the development of different eglin c variant inhibitors for different enzymes, and the use of different target enzymes for which variants are developed. A non-limiting example of a target enzyme or target enzyme family is the Caspase family of thiol proteases involved in induction of apoptosis. These enzymes are known to cleave substrates of the form Asp-Xaa-Xaa-Asp-↓(SEQ ID NO:66) or members of the Interleukin converting enzyme family (ICE) family of thiol enzymes that cleave substrates of the form Aromatic-Xaa-Xaa-Asp-↓.

This method is also applicable to enzymes whose specificity is unknown at the outset by first determining the specificity of the enzyme using standard approaches used in protease enzymology. Furthermore, this method is applicable to investigation of protein—protein interactions in general when an appropriate template is used, as described below.

D. Optimization of Affinity Toward Kex2/Furin Family Enzymes; Identification of Inhibitors for Other Enzymes.

The present invention offers a powerful method for finding potent, specific inhibitors to each member of proprotein processing proteases, as demonstrated by the Examples. Thus, in one aspect of the present invention, the strategy and approach described above is applicable to the rapid screening for potent inhibitors of any protease that can interact with the eglin reactive site loop. In another aspect of the present invention, the strategy and approach described above is applicable for optimization of heterologous protein—protein interactions in an even more general sense. Thus, in one embodiment, the present invention provides a method, utilizing the strategy and approach described above and in the Examples, to adapt a cAMP-dependent protein kinase inhibitor identified in one species to exhibit optimal inhibition of a homologous kinase from another species. It is anticipated that interactions between such inhibitors and their physiological targets may not be optimized for affinity because of physiological needs for reversibility and similar considerations. In another aspect of the present invention, optimization of adventitious contacts is used to obtain hyper-inhibitory variants that are useful as drugs or drug models.

II. Compositions

The present invention comprises novel eglin c variants, and nucleic acid sequences encoding the novel eglin c variants. The present invention also comprises compositions comprising at least one eglin c variant of the present invention. The present invention also comprises compositions comprising nucleic acid sequences encoding at least one eglin c variant of the present invention. The present invention further comprises vectors comprising nucleic acid sequences encoding at least one eglin c variant of the present invention. The present invention further comprises host cells comprising nucleic acid sequences encoding at least one eglin c variant of the present invention.

A. Eglin c Variant Proteins

The present invention comprises novel eglin c variants, which comprise at least one non-naturally occurring amino acid in an adventitious contact site, where the eglin c variant is a proprotein processing convertase inhibitor; preferably, the non-naturally occurring amino acid confers an increase in selectivity or selectivity or both for at least one proprotein processing convertase enzyme. Adventitious contact sites are eglin c residues outside of the reactive site loop but with the potential to make contact with the target enzyme. The inhibitory potency of such eglin c adventitious contact site variants against Kex2, furin and other enzymes, preferably PCs, are measured, and those variants which exhibit increased or decreased affinity relative to the control enzyme are identified as particularly useful.

The term "affinity" is used to describe the strength of the interaction between the inhibitor and an enzyme. Typically, either (i) an equilibrium dissociation constant (KD) or inhibitor constant (KI) is used (these are equivalent; higher affinity is indicated by numerically smaller values) or (ii) an equilibrium association constant (Ka) is used (higher affinity is indicated by numerically larger values; this is the reciprocal of the KD). The term "selectivity" is used to describe the relative affinity of a specific inhibitor for two different enzymes. This is quantified by a selectivity ratio: the ratio of the $K_a$ values for two inhibitors. This gives information about the relative affinity of a single inhibitor for two different enzymes. The term "specificity" is used to describe the relative reactivity of an enzyme with two substrates. This is quantified as the ratio of kcat/KM of an enzyme for the two substrates, as described in Fersht, A. R. (1985) in Enzyme Structure and Mechanism (W. H. Freeman and Co., New York) pp. 105 & 112.

In some embodiments, the non-naturally occurring amino acid replaces a naturally occurring amino acid in an adventitious contact site. In particular embodiments, the non-naturally occurring amino acid replaces a naturally occurring amino acid, selected from the group consisting of Asp33, Tyr35, Leu37, Glu39, Gly40, Leu47, Tyr49, Asn50, His65, and His68, where the numbers specify amino acid positions in native eglin c, and the amino acids are the naturally occurring amino acids at the specified amino position in native eglin c. In some particular embodiments, the non-naturally occurring amino acid Asp replaces Tyr49 (D4'), or the non-naturally occurring amino acid Val replaces Asp33, or both Asp replaces Tyr49 and Val replaces Asp33.

In an alternative aspect, the present invention provides an eglin c variant comprising at least one non-naturally occurring amino acid in an adventitious contact site, and further comprising at least one non-naturally occurring amino acid in the reactive site loop, where the eglin c variant is a proprotein processing convertase inhibitor; preferably, the non-naturally occurring amino acids confer increased specificity or selectivity or both on at least one proprotein processing enzyme.

In some embodiments of this aspect, the non-naturally occurring amino acid in the reactive site loop replaces a naturally occurring amino acid in the reactive site loop. In particular embodiments, the non-naturally occurring amino acid in the reactive site loop replaces a naturally occurring amino acid at sites selected from the group P1, P2, P3, P4, P5, and P6. In some particular embodiments, the non-naturally occurring amino acid in the reactive site loop replaces a naturally occurring amino acid at sites selected from the group consisting of positions P1 and P4. In some particular embodiments, non-naturally occurring amino acid Arg (R) occurs at position P4, and amino Arg (R) or Lys (K) occurs at position P1.

In other embodiments, the eglin c variant inhibitor is selected from the group consisting of eglin c variants R4-, M4R1-, R4R1-, M4K1-, R4K1-, R6R4F1-, K2R1-, M4K2R1-, R4,K2R1-eglin, where amino acid substitutions in the reactive site loop are indicated by the letter of the non-naturally occurring amino acid, and the position in the reactive site loop which it occupies, and where the variant further comprises at least one non-naturally occurring amino acid in an adventitious contact site. In particular embodiments, the eglin c variant inhibitor is selected from the group consisting of R4R1- and R4K1-, where the variant further comprises at least one non-naturally occurring amino acid in an adventitious contact site.

In yet other embodiments, the eglin c variant inhibitor is selected from the group consisting of eglin c variants R4-, M4R1-, R4R1-, M4K1-, R4K1-, R6R4F1-, K2R1-, M4K2R1-, R4,K2R1-, where the variant further comprises a non-naturally occurring amino acid in an adventitious contact site which replaces a naturally occurring amino acid, where the naturally occurring amino acid is selected from the group consisting of Asp33, Tyr35, Leu37, Glu39, Gly40, Leu47, Tyr49, Asn50, His65, and His68, where the numbers specify amino acid positions in native eglin c, and the amino acids are the naturally occurring amino acids at the specified amino position in native eglin c. In particular embodiments, the eglin c variant inhibitor is selected from the group consisting of R4R1- and R4K1-, and the non-naturally occurring amino acid in an adventitious contact site replaces a naturally occurring amino acid, selected from the group consisting of Asp33, Tyr35, Leu37, Glu39, Gly40, Leu47, Tyr49, Asn50, His65, and His68. In some particular embodiments, the inhibitor is selected from the group consisting of eglin c variants R4R1- and R4K1-, and the non-naturally occurring amino acid in the adventitious contact site is either Asp replacing Tyr49 (D4'), or the Val replacing Asp33, or both Asp replacing Tyr49 and Val replacing Asp33. Additional exemplary but non-limiting embodiments are described in the Examples.

The present invention also provides compositions comprising at least one eglin c variant of the present invention. The novel eglin c variants can be not only in free form, but also in the form of their salts, especially their pharmaceutically acceptable salts. Since they contain several amino acid residues having free amino groups or guanidino groups, the compounds of the invention may, for example, be in the form of acid addition salts. Suitable acid addition salts are especially physiologically tolerable salts with customary therapeutically acceptable acids. Suitable inorganic acids are hydrohalic acids (such as hydrochloric acid) but also sulfuric and phosphoric or pyrophosphoric acid; suitable organic acids are especially sulfonic acids (such as benzene or p-toluenesulfonic acid or lower alkanesulfonic acids, such as methanesulfonic acid) and also carboxylic acids, such as acetic acid, lactic acid, palmitic and stearic acid, malic acid, tartaric acid, ascorbic acid and citric acid. Since the eglin compounds also contain amino acid residues having free carboxy groups, they may also be in the form of metal salts, especially alkali metal or alkaline earth metal salts, for example sodium, potassium, calcium or magnesium salts, or in the form of ammonium salts, derived from ammonia or from a physiologically tolerable organic nitrogen-containing base. Since they may, however, contain free carboxy groups and free amino (and guanidino) groups simultaneously, they may also be present in the form of internal salts.

B. Nucleic Acid Sequences

The present invention also provides compositions comprising an isolated nucleic acid sequence encoding at least one eglin c variant of the present invention.

In some embodiments, the present invention provides a nucleic acid sequence encoding a novel eglin c variant, where the novel eglin c variant comprises at least one non-naturally occurring amino acid in an adventitious contact site, where the non-naturally occurring amino acid confers an increase in selectivity or selectivity or both for at least one proprotein processing convertase enzyme, as described previously. In other embodiments, the invention also provides a nucleic acid sequence encoding an eglin c variant comprising at least one non-naturally occurring amino acid in an adventitious contact site, and further comprising at least one non-naturally occurring amino acid in a reactive loop, where the non-naturally occurring amino acids confer increased specificity or selectivity or both on at least one proprotein processing enzyme, as described previously.

In some embodiments of the invention, the coding sequence of eglin c variants are produced by mutagenesis of adventitious contact sites or reactive loop sites or both in a naturally occurring or synthetic sequence encoding an eglin c, as described herein and in the Examples. In alternative embodiments of the invention, the coding sequence of an eglin c variant is synthesized, whole or in part, using chemical methods well known in the art (See e.g., Caruthers et al., (1980) Nucl. Acids Res. Symp. Ser., 7: 215–233; Crea and Horn (1980) Nucl. Acids Res., 9: 2331; Matteucci and Caruthers (1980) Tetrahedron Lett., 21: 719; and Chow and Kempe (1981) Nucl. Acids Res., 9:2807–2817).

Embodiments of nucleic acid sequences of the present invention include but are not limited to a nucleic acid sequence encoding eglin c variant as described above or comprising a nucleic acid sequence shown in FIG. 5.

C. Vectors and Transgenic Cells

The present invention further comprises vectors comprising nucleic acid sequences encoding at least one elgin c variant of the present invention, as is described further below. Vectors include both cloning vectors, and expression vectors; such vectors are well-known in the art, and are described further below.

The present invention further comprises host cells comprising nucleic acid sequences encoding at least one eglin c variant of the present invention, as is described further below.

III. Methods of Producing Eglin c Variants

The present method provides methods of producing eglin c variants of the present invention. In one aspect, eglin c variants of the present invention are expressed recombinantly. In one embodiment, the variants are expressed in vivo, in host cells transformed with nucleic acid sequences encoding an eglin c variant of the present invention. In another embodiment, eglin c variants of the present invention are expressed in an in vitro expression system. In another aspect, eglin c variants are produced synthetically.

A. Expression of Eglin c Variants

In aspect of the present invention, nucleic acid sequences corresponding to the eglin c variants of the present invention as described above are used to generate recombinant DNA molecules that direct the expression of the encoded protein product in appropriate host cells.

As will be understood by those of skill in the art, it may be advantageous to produce eglin c variant encoding nucleotide sequences possessing non-naturally occurring codons. Therefore, in some preferred embodiments, codons preferred by a particular prokaryotic or eukaryotic host (Murray et al. (1989) Nucl. Acids Res., 17) can be selected, for example, to increase the rate of DES expression or to produce recombinant RNA transcripts having desirable properties, such as a longer half-life, than transcripts produced from naturally occurring sequence. An example of such a sequence is provided in Example 1, Section 8.

1. Vectors for Production of Eglin c Variants

The nucleic acid sequence of the present invention can be cloned by techniques well-known in the art; exemplary techniques are described in Example 1, and include but are not limited to the use of cloning vector pBS-SK+ and pET27b(+), as described in materials and methods of Example 1.

The nucleic acid sequences of the present invention are also employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above (e.g., nucleic acid sequences encoding an eglin c variant of the present invention). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX74, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, the nucleic acid sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. Other useful promoters include inducible promoters; for example, the vector described in Example 1, pET27b(+), is induced by inducing the synthesis of T7 RNA polymerase, on a gene in the *E. coli* chromosome under the lac promoter, by adding IPTG. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

An exemplary cloning vector pET27b(+) is described in Example 1.

2. Host Cells for Production of Eglin c Variants

In a further embodiment, the present invention provides host cells containing the above-described constructs. Host cells are employed both for producing and cloning the nucleic acid sequences encoding eglin c variants, and for expressing the nucleic acid sequences encoding eglin c variants of the present invention.

In some embodiments of the present invention, the host cell is a higher eukaryotic cell (e.g., an insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomyces cerivisiae, Schizosaccharomycees pombe*, Drosophila S2 cells, *Spodoptera* Sf9 cells, Chinese hamster ovary (CHO) cells, COS-7 lines of monkey kidney fibroblasts, (Gluzman (1981) Cell 23:175), 293T, C127, 3T3, HeLa and BHK cell lines, NT-1 (tobacco cell culture line), root cell and cultured roots in rhizosecretion (Gleba et al. (1999) Proc Natl Acad Sci USA 96: 5973–5977).

The constructs in host cells can be used in a conventional manner to produce the polypeptide product encoded by the recombinant sequence. In some embodiments, introduction of the construct into the host cell can be accomplished by calcium phosphate transfection, DEAE-Dextran mediated transfection, or electroporation (See e.g., Davis et al. (1986) Basic Methods in Molecular Biology). In other embodiments, host cells are transfected by biolistic bombardment and *Agrobacterium* transfection. Yet other embodiments utilize methods of introducing DNA which include but are not be limited to the use of viral vectors of baculovirus, vaccinia virus, retroviruses, rhinoviruses and adenoviruses.

Proteins can be expressed in eukaryotic cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of Eglin c Variants

The present invention also provides methods for recovering and purifying eglin c variants from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In some embodiments of the present invention, the protocol of Example 1 Section 5 is used to purify eglin c variants. In this illustrative example, eglin c variants were purified from thawed bacterial cell wash extracts using Q and S Sepharose chromatography.

The present invention further provides nucleic acid sequences having the coding sequence (e.g., a nucleic acid sequence encoding an eglin c variant of the present invention) fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminal of an eglin c variant and which results in expression of the polypeptide in the case of a bacterial host, or for example by vector PT-23B, which adds a hexahistidine tag to the C terminal of an eglin c variant and which results in improved ease of purification of the polypeptide fused to the marker in the case of a bacterial host, or, for example, the marker sequence may be a hemagglutinin (HA) tag when a mammalian host is used. The HA tag corresponds to an epitope derived from the influenza hemagglutinin protein (Wilson et al. (1984) Cell, 37:767). Other non-limiting examples of fusions to facilitate purification of eglin c variants include fusion to glutathione-S-transferase (GST), cellulose binding domains and chitin binding domains. The fusion domains may then be cleaved off after purification.

B. Eglin c Variant Polypeptides

The present invention provides eglin c variant polypeptides. In some embodiments of the present invention, the polypeptide may be produced by recombinant techniques using a prokaryotic or eukaryotic host (e.g., by bacterial, yeast, higher plant, insect and mammalian cells in culture), while in other embodiments it may be a product of chemical synthetic procedures. In some embodiments, depending upon the host employed in a recombinant production procedure, the polypeptide of the present invention may be glycosylated or may be non-glycosylated. In other embodiments, the polypeptides of the invention may also include an initial methionine amino acid residue.

1. Purification of Eglin c Variants

In some embodiments of the present invention, eglin c variant polypeptides are purified from recombinant organisms as described above. In one embodiment, eglin c variants are partially purified by washing frozen and thawed bacterial cells with Tris-HCl buffer containing EDTA, as described in Example 1 Section 5. In another embodiment, eglin c variants are further purified by Q and S Sepharose column chromatography, as described in Example 1 Section 5.

2. Chemical Synthesis of Eglin c Variant Polypeptides

Alternatively, in some embodiments of the present invention, the polypeptides of the invention can be synthetically produced by conventional peptide synthesizers. In an embodiment of the present invention, the protein itself is produced using chemical methods to synthesize either an entire eglin c variant amino acid sequence or a portion thereof. For example, peptides are synthesized by solid phase techniques, cleaved from the resin, and purified by preparative high performance liquid chromatography (See e.g., Creighton (1983) Proteins Structures And Molecular Principles, W H Freeman and Co, New York N.Y.). In other embodiments of the present invention, the composition of the synthetic peptides is confirmed by amino acid analysis or sequencing (See e.g., Creighton, supra).

Direct peptide synthesis can be performed using various solid-phase techniques (Roberge et al (1995) Science, 269: 202–204) and automated synthesis may be achieved, for example, using ABI 431A Peptide Synthesizer (Perkin Elmer) in accordance with the instructions provided by the manufacturer. Additionally, the amino acid sequence of an eglin c variant, or any part thereof, may be altered during direct synthesis and/or combined using chemical methods with other sequences to produce a variant polypeptide.

Chemical synthesis of eglin c has been accomplished by Lu and Kent (Lu W. et al. (1999) Chemistry and Biology, July, 6(7):419–27).

IV. Methods of Using Eglin c Variants of the Present Invention

A. Use to Treat Diseases

1. Use of Eglin Variants as Antiviral, Antibacterial, and Antifungal Drug Candidates Eglin c variants of the present invention that exhibit high-affinity inhibition of furin are anticipated to inhibit endogenous furin activity in cells, and thus provide a platform for development of a general class of anti-viral and anti-bacterial drugs targeted against the host enzyme furin or furin-like enzymes.

Furin is thought to be involved in processing of numerous viral envelope glycoproteins and bacterial protoxins (Molloy, S. S. et al. (1999) Trends in Cell Biol. 9: 28–35). For example experiments utilizing peptidyl chloromethylketones and the a1-antitrypsin variant, a1 —PDX, have shown that inhibition of furin in tissue culture cells can block processing of HIV gp160 and other viral envelope glycoproteins (Klenk H D and Garten W. (1994) Trends in Microbiology 2: 39–43; Garten, W et al. (1994) Biochimie 76: 217–227; Anderson, E. D. et al. (1993); Jean, F. et al. (1998) Proc. Natl. Acad. Sci. U.S.A. 95: 7293–7298; and Jean F et al. (2000) Proc. Natl. Acad. Sci. U.S.A. 97: 2864).

Knocking out the furin gene in mouse results in embryonic lethality (Roebroek A J et al. (1998) Development 125: 4863–4876). Indeed, the catalogue of known and suspected targets for furin processing (Molloy, S. S. et al. (1999) Trends in Cell Biol. 9: 28–35) suggests that prolonged inhibition of furin ought to be toxic to adults as well as to mammalian development. However, furin deficient cell lines are viable and have even been selected by their virus-resistance or bacterial toxin-resistance (Inocencio N M et al. (1993) J. Virol. 67: 593–595; Moehring J M et al. (1993) J. Biol. Chem. 268: 2590–2594; Takahashi S et al. (1993) BBRC 195: 1019–1026; and Takahashi S et al. (1995) J. Biol. Chem. 270: 26565–26569). Therefore, although chronic inhibition of furin activity in a clinical setting does not appear feasible, acute inhibition of furin or furin-like processing enzymes in the case of acute viral infection or bacterial toxemia is anticipated to provide a powerful therapeutic approach to such infections.

Furin-directed inhibitors offer several advantages as antiviral and bacterial agents. One important advantage is that because the inhibitors are directed at a host enzyme, resistant viral or bacterial variants will not arise. Another important advantage is that furin-directed inhibitors are anticipated to act against a broad spectrum of viruses and bacterial toxins. For examples, viruses that require furin-like processing include but are not limited to respiratory syncytial viruses (Bolt G et al. (2000) Virus Research 68: 25–33), measles viruses, ebola viruses (Volchkov V E et al. (1998) Proc. Natl. Acad. Sci. USA 95: 5762–5767), paramyxoviruses, encephalitis viruses (Stadler K et al. (1997) J. Virol. 71: 8475–8481), hanta viruses, fowl plague or type A influenza viruses (Subbarao et al. (1998)), human immunodeficiency viruses, human cytomegaloviruses, mouse mammary tumor virus-7, Newcastle disease viruses, Sindbis viruses, and human parainfluenza virus type 3 (Nakayama, K (1997) Biochem J. 327: 625–635). For most of these viruses, there are no chemotherapies available, but rather only symptom management. Each of these is an acutely infectious agent which could be overcome by a host immune response, if virulence were attenuated for a period of time by a chemotherapeutic strategy. A similar argument applies to the inhibition of bacterial toxin processing; examples of bacterial toxins processed by furin or furin-like processing include but are not limited to Pseudomonas aeruginosa exotoxin A, anthrax protective antigen (Molloy, S. S. et al. (1999) Trends in Cell Biol. 9: 28–35), Shiga toxin (Garred O et al (1995) J. Biol. Chem. 270: 10817–10821), and Diphtheria toxin (Tsuneoka M et al (1993) J. Biol. Chem. 268: 26461–26465).

Thus, a patient acutely infected with an infectious agent, such as a bacterial, viral, or fungal disease, where disease progression is dependent upon a proprotein processing convertase or similar enzyme, is a patient in need of treatment. In particular embodiments, the treatment attenuates the virulence of the infectious agent for a period of time sufficient to allow the host immune system to overcome the infectious agent and/or to allow another therapy to overcome the infectious agent; in some preferred embodiments, the treatment results in inhibition of a proprotein processing convertase or similar enzyme necessary to the disease progression. A therapeutically effective amount is an amount which renders a beneficial effect on the progress of the disease resulting from the infectious agent; preferably, the amount is sufficient to attenuate the virulence of the infectious agent for a period of time sufficient to allow the host immune system to overcome the infectious agent and/or to allow another therapy to overcome the infectious agent. The patient is a mammal or other animal.

A patient exposed to an infectious agent, such as a bacterial, viral, or fungal disease, where disease progression is dependent upon a proprotein processing convertase or similar enzyme, is also a patient in need of treatment. In particular embodiments, the treatment prevents and/or attenuates the virulence of the infectious agent for a period of time sufficient to allow the host immune system to overcome the infectious agent and/or to allow another therapy to overcome the infectious agent; in preferred embodiments, the treatment results in inhibition of a proprotein processing convertase or similar enzyme necessary to the disease progression. A therapeutically effective amount is an amount which renders a beneficial effect on the initiation and/or progress of the disease resulting from the infectious agent; preferably, the amount is sufficient to prevent and/or attenuate the virulence of the infectious agent for a period of time sufficient to allow the host immune system to overcome the infectious agent and/or to allow another therapy to overcome the infectious agent. The patient is a mammal or other animal.

The present invention provides several eglin c variants which are potent inhibitors of furin or furin-like processing proteases. As described previously, furin or furin-like enzymes are involved in the entry of bacterial toxins and viruses into host cells. The inhibitors of the present invention are anticipated to block the activation of bacterial protoxins (e.g. Anthrax protective antigen) and the essential viral envelope glycoproteins for diverse viruses, e.g. Ebola virus and avian influenza virus A (fowl plague influenza virus (Horimoto T et al. (1994) J. Virol. 68: 6074–6078.). Thus, in one aspect of the present invention, an eglin-c based variant of the present invention is administered to a patient in need thereof, in therapeutically effective amounts. The following paragraphs provide further descriptions of non-limiting exemplary diseases for which the administration of an eglin c based variant of the present invention is contemplated.

Anthrax

Anthrax is a fatal bacterium infection resulting from entry of *Bacillus anthracis* endospores, a soil organism, into the body through abrasions in the skin or by inhalation. Anthrax toxin infections involve agricultural workers in direct contact with infected herbivores, or industrial workers in direct contacts with infected animal products such as wool (Pile et al. (1998)). Anthrax has been a zoonotic illness reported world-wide for millennia. The incidence of anthrax currently appears to be considerably lower than it has been in the past, but the apparent decrease may be incorrect, as anthrax is not reported in many nonindustrialized countries. Anthrax spores are resistant to harsh conditions and many disinfectants, and may be dormant in soils for decades. Their dormancy allowed anthrax spores to be developed as biological weapons by a number of nations. U.S. military personnel have been treated with a costly vaccination program since 1997.

*Bacillus anthracis* secretes three proteins to form toxic complexes at the surface of mammalina cells. These three proteins are two toxins, lethal factor (LD) and edema factor (EF), and a third protein, protective antigen. The two toxins are independently synthesized and secreted by the bacteria, and must pass through a pore in a mammalian cell in order to express their toxicity. The protective antigen is also synthesized independently and secreted by the bacteria, and froms a pore in a cell plasma membrane via a multi-step process and through which the two toxins gain entry into a cell. Secreted protective antigen first binds to a receptor on the surface of a cell, and is then proteolytically activated. The activating protease is furin, which is present at the cell surface of macrophages and monocytes within the lungs, and which cleaves protective antigen from an 83 dDa protein to a 63 kDa fragment. The 63 kDa fragment oligomerizes and then binds to either or both toxins; development of a proton gradient across the cell membrane results of translocation of the toxins into the cell. Thus, activation of the protective antigen (PA63) of *Bacillus anthracis* is integral to the mechanism of anthrax toxicity, and results in the endocytosis of the toxin factors.

Several of the eglin-c based variants are effective as inhibitors of furin; some exhibit increased selectivity for furin (as described in Example 2). Moreover, the inventors have shown that the addition of eglin-c based variants to extracullular media of tissue culture cells results in inhibition of processing of pro-on Willebrand factor in the cultured cells (as described in Example 3); these results show that it is possible to inhibit cellular processing by additiona of a purified elgine variant protein. It is anticipated that eglin variants of the present invention provide an economical approach to combating Anthrax toxicity (as described in Example 4). Therefore, in another aspect of the invention, an eglin-c based variant of the present invention is administered to a patient in need thereof, in therapeutically effective amounts, where the patient is exposed to and/or infected with *Bacillus anthracis*.

Ebola Haemorrhagic Fever

As of 16 Oct. 2000, the World Health Organization (WHO) reported outbreak of Ebola haemorrhagic fever in Uganda, including 71 suspected cases and 35 death. Ebola haemorrhagic fever is one of the most virulent viral diseases known to humankind, and it is transmitted through direct contact with a patient's body or bodily fluids. No specific treatment is available (WHO 1997). It is anticipated that eglin c based inhibitors of the present invention can be utilized as economical, nontoxic anti-viral reagents. Thus, in one aspect of the present invention, an eglin-c based inhibitor of the present invention is administered to a patient in need thereof, in therapeutically effective amounts, where the patient is infected with Ebola virus.

Fowl Plague Viruses

Fowl plague viruses are highly contagious Type A Influenza viruses that act as pathogens for both wild and domestic bird populations. The virus is particularly pathogenic for domestic fowl such as chickens, where lethality can reach 100% of birds confined to a common space. A zoonotic disease involving a Type A Flu which was transmitted to humans from chickens or ducks in Hong Kong in 1998 was known as Hong Kong chicken virus. The virus caused 87.5 to 100 percentage mortality in experimentally inoculated animals and 30 to 40% mortality to human patients. Sequence analysis of the virus revealed the presence of a furin cleavage site within the viral envelope glycoprotein, the hemagglutinin of the zoonotic virus (Subbarao et al. (1998)), a signature of fowl plague viruses, and the reason for their high degree of pantropism and consequent mortality (due to productive infection of multiple organ systems and CNS instead of just the gut and lung). It is likely that additional zoonotic fowl plague virus transmission events will occur, and it is possible that such events will involve more easily transmissible viruses. It is anticipated that eglin c based inhibitors of the present invention can be utilized block fowl plague virus replication in humans and to provide a defense against such events. As fowl plague viruses are highly pathogenic in poultry, it is anticipated that use of eglin c based proprotease inhibitors of the present invention as protective reagents against fowl plague virus could be useful agriculturally. Therefore, in another aspect of the invention, an eglin-c based inhibitor of the present invention is administered to a patient in need thereof, in therapeutically effective amounts, where the patient is infected with a fowl plague virus.

Fungal Diseases

It is also anticipated that eglin c variants of the present invention are effective against fungal diseases, including but not limited to infections such as candidiasis, aspergillus infections and pneumocystis pneumonia. Fungal infections are especially problematic for immune suppressed patients, as for example, transplant and AIDS patients. Mutation of the KEX2 gene in *Candida albicans* results in defects in hyphal formation and presumably reduced pathogenicity (Newport G, and Agabian N. (1997) Journal of Biological Chemistry, November 14, 272 (46): 28954–61). In one aspect of the invention, an eglin c variant of the present invention is administered to a patient in need thereof, in therapeutically effective amounts, where the patient is infected with a fungal disease. In some embodiments, eglin c variants of the present invention are utilized as inhalant drugs in anti-fungal applications, such as against the GPI-anchored major surface Kex2-like protease in *Pneumocystis carinii*. A large family of such enzymes are localized to the cell surface and are thought to be involved in processing the major surface glycoprotein which is the principal immunodeterminant (Lugli E B et al. (1999) Molecular Microbiology, March, 31(6):1723–33). In other embodiments, eglin c variants of the present invention are utilized as a systemic drug against other fungal agents.

2. Use of Eglin c Variants in Other Therapies

The present invention provides a method for developing eglin c variants which are inhibitors highly specific for furin (as opposed to other proprotein processing proteases and other proteases) or for other proprotein processing proteases; the methods, as described previously, are based upon the randomization of adventitious contacts sites, and testing the resulting variants for protease inhibitor activity. It is anticipated that eglin c variants specific for selected proprotein processing proteases are effective against normal processing reaction and pathogenic processing reaction of Kex2/furin family enzymes in vivo, and can be employed to regulate such enzymes in vivo.

In some embodiments, the invention provides eglin c-based caspase inhibitors which are known to exhibit specificity for the primary side and prime side of substrates; such inhibitors are particular useful for use in blocking caspases which are involved in programmed cell death. In other embodiments, the invention provides eglin c-based inhibitors for other serine, metallo, aspartyl and thiol proteases. For example, degenerative diseases, such as Alzheimer's disease and Huntington's disease, are by anti-apoptotic drugs directed against the Caspase family of thiol proteases, and are anticipated to respond well to treatment with an eglin c variant of the present invention.

In yet other embodiments, viral diseases are targeted by creating inhibitors of virally encoded proteases such as the picornavirus thiol proteases (e.g. the rhinoviruses, the enteroviruses (including polioviruses, coxsackieviruses and echoviruses) and the hepatoviruses (including hepatitis A virus) (Rotbart H A, (2000) Antiviral Chemistry and Chemotherapy, July, 11(4):261–71).

Because furin undergoes a natural pathway of transport between the trans Golgi network, the major site of processing of biosynthetic secretory proproteins and the cell surface (Molloy, S. S. et al. (1999) Trends in Cell Biol. 9: 28–35.), it is possible to inhibit all of the intracellular furin by exposing the exterior of the cell over a period of time to a furin inhibitor. As a result, it is anticipated that variants of eglin c which are inhibitors of proprotein processing proteases will easily have bioaccess to its target protease, as eglin c is a small polypeptide of only 70 amino acids. However, the present invention also provides embodiments by which eglin c variants of the present invention have access to intracellular compartments. In one aspect, the present invention comprises a membrane-translocation promoting peptide attached to an eglin c variant of the present invention, thus as providing a means by which eglin c variants can access the intracellular space. Preferably, such a peptide is the membrane-translocation promoting TAT peptide of HIV-1. It is anticipated that such modified eglin c variants of the present invention would render cytosolic proteases, such as caspases (cell death proteases) accessible to eglin-based inhibitors.

3. Pharmaceutical Compositions

The present invention further provides pharmaceutical compositions which comprise at least one eglin c variant of the present invention, alone or in combination with at least one other agent, such as a stabilizing compound, and which may be administered in any sterile, biocompatible pharmaceutical carrier, including, but not limited to, saline, buffered saline, dextrose, and water.

The methods of the present invention find use in treating diseases or altering physiological states as described above in which a PC or an enzyme for which an eglin c variant of the present invention is an inhibitor plays a role. The invention provides methods for inhibiting PCs by administering an elgin c variant of the present invention. Eglin c variants of the present invention may be administered by any number of routes, including but not limited to by injection, by inhalation, and by ingestion; preferred routes are by injection and by inhalation.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, at least one eglin c variant of the present invention is administered to a patient alone, or in combination with other nucleotide sequences, drugs or hormones or in pharmaceutical compositions, where it may be further mixed with excipient(s) or other pharmaceutically acceptable carriers. In one embodiment of the present invention, the pharmaceutically acceptable carrier is pharmaceutically inert.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

Peptides can be administered to the patient by injection in a pharmaceutically acceptable carrier such as physiological saline. Thus, pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal.

In other embodiments, therapeutic amounts of eglin c variants of the present invention are administered by inhalation. The administration of therapeutic compositions to the respiratory airways is a well developed art in the field, and such methods are applicable here. Typically, an aerosolized or nebulized (vaporous) liquid composition containing a therapeutically-effective amount of an eglin c variant of the present invention is delivered to the respiratory airways by breathing in the vaporous composition, or by forced (pressurized) periodic inflation breathing of the lungs with the vapor. Means for delivering a therapeutic composition comprises a device which produces an aerosol of a liquid composition, which devices are generally well known in the art. These devices can be nebulizers, small particle aerosol generators, inhalers with a propellant, and the like devices.

In yet other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of an eglin c variant may be that amount that inhibits a targeted PC activity. Determination of effective amounts is well within the capability of those skilled in the art, especially in light of the disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition.

The pharmaceutical composition may be provided as a salt and can be formed with many acids, as described previously. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts levels of an eglin c variant of the present invention.

A therapeutically effective dose refers to that amount of an eglin c variant of the present invention which ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature.

B. Use as Reagents for General Biological Applications

The present invention also provides eglin c variants which are optimized at adventitious contact sites alone (eg, optimized at non-reactive loop sites), or at both reactive site and adventitious contact sites (eg, optimized at reactive loop sites and non-reactive loop sites) as reagents for general biological applications. In one embodiment of the present invention, an eglin c variant of the present invention is utilized as an affinity-purification reagent. In another embodiment of the present invention, an eglin c of the present invention is utilized as a fluorescence tag for identification of cells containing target proteases, subcellular localization of proteases, and tracking internalization of drug. In yet another embodiment of the present invention, an eglin c variant of the present invention is utilized as an inhibitor for selective inhibition of processing or other proteases in cell culture or transgenic animals as a method of determining the physiological functions of those proteases.

In one embodiment of the present invention, an eglin c variant of the present invention is used as an affinity purification reagent for affinity purification of proprotein processing proteases. A variant of eglin c which is a selective inhibitor of a particular processing protease is utilized to separate that processing protease from other proteins. The eglin c variant of the present invention is bound to an affinity reagent and utilized for protein purification by techniques well-known in the art; exemplary affinity resin preparation and use is described in Example 3.

In another embodiment of the present invention, an eglin c of the present invention is utilized as a fluorescence tag for identification of cells containing target proteases, for subcellular localization of proteases, and for tracking internalization of drug. In one aspect of the invention, a Cys residue introduced into Glu39Cys-R4R1-, Tyr49Cys-R4R1-, and His65Cys-R4K1-eglin variants by randomization at adventitious contact sites is modified with thiol-reactive probes such as coumarin derivatives or fluorescent dyes. These residues are located out side of the reactive site, and are used to monitor interaction of the inhibitor with processing proteases in vivo.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); 1 or L (liters); ml (milliliters); μl (microliters); cm (centimeters); mm (millimeters); μm (micrometers); nm (nanometers); ° C. (degrees Centigrade); Sigma (Sigma Chemical Co., St. Louis, Mo.); and AMC, 7-amino-4-methylcoumarin; BCA, bicichonnic acid; CI2, Chymotrypsin inhibitor 2; IPTG, isopropyl thio galactoside; MALDI, matrix-assisted laser desorption/ionization; LB, a specific type of bacterial growth medium; MES, 2-(N-morpholino)ethanesulfonic acid; MUTMAC, 4-methylumbelliferyl p-(N,N,N-trimethylammonium)cinnamate; NPGB, p-nitrophenyl p-guanidinobenzoate hydrochloric acid; PAGE, polyacrylamide gel electrophoresis; PC, proprotein convertase; TUG, transverse urea gradient.

Example 1

Creation of First Generation Eglin c Variants: Reactive Loop Site Variants

1. Reagents used in Examples 1 and 2. All restriction enzymes, Vent DNA polymerase and DNA modifying enzymes were from New England BioLabs. NuSieve GTG agarose was from FMC. The pET27b(+) vector was from Novagene. A chromogenic substrate, H-D-Ile-Pro-Arg-pNA, was from DiaPharma (OH). Fluorogenic substrates, Boc-Pro-Val-Arg-MCA, Boc-Arg-Val-Arg-Arg-MCA, and pyrArg-Thr-Lys-Arg-MCA were from Bachem Bioscience. 4-Methylumbelliferyl p-(N,N,N-trimethylammonium)cinnamate (MUTMAC) was from Sigma. Oligonucleotides (University of Michigan DNA Core Facility) were purified by PAGE in 7 M urea. Secreted, soluble Kex2 (hereafter, "Kex2") was purified and active-site titrated as described (Li, A., and V. Daggett, V. (1995) Protein Engineering 8, 1117–1128; and Rockwell, N. C., and Fuller, R. S. (1998) Biochemistry 37: 3386–3391). Serum free media adopted insect cells (sf-9 cells) were from Gibco BRL. Human neutrophil elastase, plasma kallikrein, and plasmin were from Athens Research and Technology. The micro BCA assay kit was from Pierce.

2. Synthesis and structure of eglin c gene. Techniques well known in the art for molecular biology and bacterial cell growth were utilized (see, for example, Sambrook, J. et al. (1989) Molecular Cloning, Cold Spring Harbor Laboratory Press, New York). A synthetic gene (231 bp, FIG. 1) encoding Arg45 in place of Leu45 was designed following a previously published eglin c synthetic gene as a guide (Rink, H. et al. (1984) Nucleic Acid Research 12: 6369–6387). The synthetic gene (231 bp) was divided into six fragments of ~55 bp. Assembly of the paired segments was performed by PCR using Vent DNA polymerase. The final gene product was subcloned into pBS-SK+ and sequenced. NdeI and BamHI sites were created at the 5' and 3' ends of the final PCR product to facilitate subcloning of the synthetic gene into the expression vector pET27b(+) (see below). AatII and BglII restriction sites flanking the DNA sequences encoding the reactive site loop of eglin c were also introduced in the sequence of the synthetic gene to permit replacement of sequences encoding the reactive site loop with oligonucleotides that would encode altered amino acid sequences.

3. Mutagenesis of reactive site loop. The reactive site loop from Arg45 (P1) to Gly40 (P6) was mutated by replacing the AatII-BglII fragment with synthetic, double-stranded oligonucleotides with appropriate stick ends. These oligonucleotides were designed to destroy the AatII and BglII sites after ligation as a means of diagnosing their insertion. Using these sites, a series of substitutions was made at the P2, P4 and P6 positions in the R1-eglin. A gene encoding a recombinant eglin having the reactive site sequence of naturally occurring eglin c was also constructed. The product of this gene was termed "L1-eglin". L1-eglin ("wild type eglin") has the N-terminal sequence SMGSELK (SEQ ID NO: 25), in contrast to the naturally occurring eglin c N-terminal sequence of TEFGSELK (SEQ ID NO:26). Other variants were designated by according to the substitutions made at the P1, P2, P4 and P6 positions (see Table 1). Automated DNA sequencing was used to confirm each construction. Table 1 shows the amino acid sequences of the eglin variants and their specific designations. Oligonucleotides used for cassette mutagenesis are shown in Table 2.

Table 1. Amino acid substitutions in the reactive site loop are shown relative to the wild type sequence. Each variant is termed as in the first column. Residues identical to the L1-eglin are indicated by "-".

Summary of MWs of Eglin Variants Determined by MALDI Mass Spectrometry[a].

[a]The N-terminal sequences of the eglin variants were determined to be Ser-Met-Gly-Ser-Glu-Leu- (SEQ ID NO:27), implying removal of the N-terminal Met residue; therefore, calculated MWs assume the absence of the N-terminal Met. Residues identical to L1-eglin are indicated by "-".

Summary of MWs of eglin variants determined by MALDI Mass spectrometry[a].

| Eglin variant | P6 | P5 | P4 | P3 | P2 | P1 | MW obsd | MW calcd |
|---|---|---|---|---|---|---|---|---|
| L1- | Gly | Ser | Pro | Val | Thr | Leu | 7932 | 7931 |
| R1- | — | — | — | — | — | Arg | 7970 | 7974 |
| R4- | — | — | Arg | — | — | — | 7988 | 7990 |
| M4R1- | — | — | Met | — | — | Arg | 8011 | 8008 |
| R4R1- | — | — | Arg | — | — | Arg | 8034 | 8033 |
| M4K1- | — | — | Met | — | — | Lys | 7981 | 7983 |
| R4K1- | — | | Arg | — | — | Lys | 8006 | 8006 |
| R6R4R1- | Arg | — | Arg | — | — | Arg | 8137 | 8133 |
| K2R1- | — | — | — | — | Lys | Arg | 8004 | 8001 |
| M4K2R1- | — | — | Met | — | Lys | Arg | 8038 | 8035 |
| R4K2R1- | — | — | Arg | — | Lys | Arg | 8062 | 8060 |

[a]The N-terminal sequences of the eglin variants were determined to be Ser-Met-Gly-Ser-Glu-Leu- (SEQ ID NO:27), implying removal of the N-terminal Met residue; therefore, calculated MWs assume the absence of the N-terminal Met.
Residues identical to L1-eglin are indicated by "—".

TABLE 2

Oligonucleotides for cassette mutagenesis in the reactive site loop from Arg45 (P1) to Gly40 (P6).

| | | |
|---|---|---|
| L1- | 5' TTACTTCCTGCCGGAAGGTTCTCCTGTTACCCTG 3' | (SEQ ID NO:28) |
| | 5' GATCCAGGGTAACAGGAGAACCTTCCGGCAGGAAGTAAACGT 3' | (SEQ ID NO:29) |
| R1- | 5' TTACTTCCTGCCGGAAGGTTCTCCTGTTACCCGT 3' | (SEQ ID NO:30) |
| | 5' GATCACGGGTAACAGGAGAACCTTCCGGCAGGAAGTAAACGT 3' | (SEQ ID NO:31) |
| R4- | 5' TTACTTCCTGCCGGAAGGTTCTCGTGTTACCCTG 3' | (SEQ ID NO:32) |
| | 5' GATCCAGGGTAACAGGAGAACCTTCCGGCAGGAAGTAAACGT 3' | (SEQ ID NO:33) |
| M4R1 - | 5' TTACTTCCTGCCGGAAGGTTCTATGGTTACCCGT 3' | (SEQ ID NO:34) |
| | 5' GATCACGGGTAACCATAGAACCTTCCGGCAGGAAGTAAACGT 3' | (SEQ ID NO:35) |
| R4R1- | 5' TTACTTCCTGCCGGAAGGTTCTCGTGTTACCCGT 3' | (SEQ ID NO:36) |
| | 5' GATCACGGGTAACACGAGAACCTTCCGGCAGGAAGTAAACGT 3' | (SEQ ID NO:37) |
| R6R4R1- | 5' TTACTTCCTGCCGGAACGTTCTCGTGTTACCCGT 3' | (SEQ ID NO:38) |
| | 5' GATCACGGGTAACACGAGAACGTTCCGGCAGGAAGTAAACGT 3' | (SEQ ID NO:39) |
| K2R1- | 5' TTACTTCCTGCCGGAAGGTTCTCCTGTTAAACGT 3' | (SEQ ID NO:40) |
| | 5' GATCACGTTTAACAGGAGAACCTTCCGGCAGGAAGTAAACGT 3' | (SEQ ID NO:41) |
| M4K2R1- | 5' TTACTTCCTGCCGGAAGGTTCTATGGTTAAACGT 3' | (SEQ ID NO:42) |
| | 5' GATCACGTTTAACCATAGAACCTTCCGGCAGGAAGTAAACGT 3' | (SEQ ID NO:43) |
| R4K2R1- | 5' TTACTTCCTGCCGGAAGGTTCTCCTGTTAAACGT 3' | (SEQ ID NO:44) |
| | 5' GATCACGTTTAACACGAGAACCTTCCGGCAGGAAGTAAACGT 3' | (SEQ ID NO:45) |

4. Expression of eglin c variants. Variant genes were subcloned into expression vector pET27b(+). The plasmid DNA were transformed into bacterial host strain BL21(DE3) following standard methods for molecular biology. Protein expression was induced with IPTG when cells grown in LB medium containing 30 μM kanamycin reached an OD600 of 0.4. The harvested cells were washed with 150 mM NaCl and frozen (−80° C.).

5. Purification of eglin c variants. Surprisingly, although the synthetic eglin c gene encoded no signal peptide, washing thawed cells with 50 mM Tris-HCl (pH 8) containing 2 mM EDTA released the eglin proteins quantitatively without extensive cell lysis. To remove medium contaminants, the tris extract was treated with Q-Sepharose in 20 mM Tris-HCl (pH 8.0). At this stage proteins were free from main contaminants, but were further purified by S-Sepharose chromatography in 20 mM sodium acetate (pH 5.0), ) and eluted with a linear NaCl gradient, 0.0 to 0.6 M NaCl. Purified eglin variants were judged to be homogeneous by SDS-PAGE. The percentage of active species was determined to be 99.5 by comparing results of inhibition and protein (BCA) assays. Eglin inhibitory activity was titrated as described below. Total yields of purified proteins were ~7 mg from 100 ml of bacterial culture. Molecular weights of eglin variants were determined by MALDI mass spectrometry. All purified eglin variants have Ser-Met-Gly-Ser-Glu-Leu- (SEQ ID NO:67) at the N-terminal. The N-terminal sequence of the naturally occurring eglin c is Thr-Glu-Phe-in place of Ser-Met-in engineered eglin variants in present work. MWs of eglin variants determined by MALDI Mass spectrometry were consistent to calculated values within experimental error.

6. Characterization of interaction of eglin c variants with processing proteases. Inhibitor concentrations of eglin variants were determined by titrating them with active site titrated trypsin or Kex2. Active site titration of Kex2 and furin was performed using an RQF-3 rapid-quenched flow apparatus as described (Brenner, C. and Fuller, R. S. (1992) Proc. Natl. Acad. Sci. USA 89: 922–926). Furin was titrated by measuring the initial burst of AMC product from hydrolysis of pyrArg-Thr-Lys-Arg-MCA (SEQ ID NO:68) (307 μM) at 21° C. with reaction times ranging from 4 msec to 60 sec. Active-site titration of trypsin was done using the chromogenic substrate p-nitrophenylguanidinobenzoate (NPGB) (Chase, T., and Shaw, E. (1969) Biochemistry 8: 2212–2224).

Purified eglin variants were titrated with active-site titrated Kex2 or trypsin, by measuring hydrolysis of chromogenic substrates H-D-Ile-Pro-Arg-pNA or Boc-Arg-pNA on a Uvikon Spectrophotometer (Kontron) at 21° C., in either: Kex2 assay buffer: 200 mM Bistris containing 1 mM $CaCl_2$, 0.1% (v/v) Triton-X-100; or in furin assay buffer: 20 mM NaMES containing 1 mM $CaCl_2$, 0.1% (v/v) Triton-X-100. R1-, M4K1-, and R4K1-eglin variants were incubated with trypsin (0.5 μM) until the inhibition reached equilibrium. Bz-Arg-pNA hydrolysis by residual trypsin activity was monitored. M4R1-, R4R1-, and R6R4R1-variants were titrated with the active site titrated Kex2 (0.1 μM). All titration mixtures were analyzed by SDS-PAGE after titration. When no cleavage products of the inhibitors were detected, the accuracy of the titration was confirmed. Three eglin variants, K2R1-, M4K2R1-, and R4K2R1-eglin were not titratable with tested enzymes. For these inhibitors, protein concentration determined by BCA assay was used as the inhibitor concentration. L1-eglin was titrated with chymotrypsin which was active-site titrated with MUTMAC.

Affinities of eglin variants with secreted, soluble Kex2 (hereafter "Kex2"; Brenner, C. and Fuller, R. S. (1992) Proc. Natl. Acad. Sci. USA 89: 922–926) and secreted, soluble furin (hereafter, "furin"; Bravo, D. A. et al (1994) J. Biol. Chem. 269: 25830–25837; and Komiyama & Fuller (2000) Biochemistry 39: 15156–15165) were measured by incubating variants with the enzymes (~0.5 to 2.0 nM) for 45 min to 1 h at 21° C. in one of two enzyme assay buffers. For Kex2, the buffer was 200 mM Bistris (pH 7.27) containing 1 mM $CaCl_2$ and 0.1% Triton X-100; and for furin, the buffer was 20 mM NaMES (pH 7.0) containing 1 mM $CaCl_2$ and 0.1% Triton X-100 for furin. 100 to 200 μL aliquots of reaction mixtures were transferred into triplicate wells of opaque 96 well plates (Costar), and residual enzyme activity was measured with an fmax fluorescence micro plate reader (Molecular Devices) by monitoring hydrolysis of a fluorogenic substrate Boc-Arg-Val-Arg-Arg-MCA. Data were graphically analyzed (KaleidaGraph) with an equation developed by Green and Work (1953). $K_i$ values for eglin variants are summarized in Table 3. Site-directed mutagenesis at P2 and P6 of eglin c generated temporary inhibitors (Table 3) and exhausted possibility to improve affinity further with this approach.

TABLE 3

Affinity $K_i$ (M) of eglin variants with Kex2 and furin.

| Eglin variant | $K_i$ (M) | |
|---|---|---|
| | Kex2 | Furin |
| L1- | ~5 × 10-4 | 1.2 × 10-4 |
| R1- | 3.0 × 10-8 | 5.3 × 10-5 |
| R4- | 1.0 × 10-4 | 5.6 × 10-5 |
| M4R1- | 3.4 × 10-10 | 3.6 × 10-6 |
| R4R1- | 9.1 × 10-10 | 2.5 × 10-9 |
| R4K1- | 2.5 × 10-9 | 3.8 × 10-8 |
| M4K1- | 4.5 × 10-9 | 1.7 × 10-5 |
| R6R4R1- | 2.9 × 10-10 | 2.0 × 10-9* |
| K2R1- | 6.7 × 10-10* | 1.0 × 10-7* |
| M4K2R1- | 5.9 × 10-10* | 8.3 × 10-8* |
| R4K2R1- | ~5 × 10-10* | ~5 × 10-10* |

*indicates temporary inhibition. Note that R6R4R1-eglin is a stable inhibitor of Kex2 and a temporary inhibitor of furin.

Example 2

Creation of Second Generation Eglin c Variants: Adventitious Contact Site Variants 1. Identification of sites of potential adventitious contacts. Ten residues were selected from close examination of the crystal structure of the eglin c-subtilisin Carlsberg complex (Bode, W. et al. (1986) EMBO J. 5: 813–818.). Eglin c residues within 5 Å of the subtilisin Carlsberg surface were chosen. The ten selected residues are shown in Table 4.

TABLE 4

Ten selected residues as "Adventitious contact sites", for randomization, and defined substitutions for equal or enhanced inhibition of furin relative to inhibition by the template.

| | | |
|---|---|---|
| Asp33 | Gly40 | His65 |
| Tyr35 | Leu47 | His68 |
| Leu37 | Tyr49 | |
| Glu39 | Asn50 | |

2. Limited randomization of potential sites of adventitious contacts and creation of libraries. Limited randomization of eight sites was performed as an initial survey of potential adventitious contact residues (Table 5).

In this Example, R4R1-eglin and R4K1-eglin template genes were used. Limited randomization of the eight codons (see Table 5) was achieved by complete randomization of the first two positions of each codon and partial randomization (C or T only) in the coding strand at the third position of each codon. This reduced the complexity of the libraries, eliminated the possibility of generating nonsense mutations and therefore simplified screening procedures. This approach eliminated codons for Gln, Glu, Met, Lys, and Trp. The resulting eglin c variants created are shown in Table 5; this table includes the starting template gene, and each naturally occurring amino acid and the site it occupies, as well as the non-naturally occurring amino acids which replaced it.

TABLE 5

Eight selected residues as "Adventitious contact sites", for the limited randomization, and defined substitutions for equal or enhanced inhibition of furin relative to inhibition by the template.

| R4R1-Template | R4K1-Template |
|---|---|
| Tyr35 Ile | Asp33 Gly, Ile, Val |
| Glu39 Gly, Ser, Cys, His, Pro, Tyr | Leu37 Gly |
| Gly40 Ala, Pro, Arg | Asn50 Asp |
| Leu47 Val | |
| Tyr49 Ala, Asp, Cys | |

To construct libraries, two approaches were used. Oligonucleotide cassette mutagenesis utilizing unique AatII and BglII restriction sites was used for residues 35 to 40. A PCR-based strategy, the "QUICKCHANGE site-directed mutagenesis" system from Stratagene was used for residues 33 and 47 to 50. The oligonucleotides used, having NNC or NNT in place of individual target codons, are listed in Table 6.

TABLE 6

Oligonucleotides for random mutagenesis.

| | | |
|---|---|---|
| Asp33NNY 5' | CCGCAGTACNNYGTTTACTTCCTGCCGGAA 3' | (SEQ ID NO:46) |
| 5' | GAAGTAAACRNNGTACTGCGGGTAATGCAG 3' | (SEQ ID NO:47) |
| Tyr35NNY 5' | TNNYTTCCTGCCGGAAGGTTCTCGTGTTACCCGT 3' | (SEQ ID NO:48) |
| 5' | GATCACGGGTAACACGAGAACCTTCCGGCAGGAARNNAACGT 3' | (SEQ ID NO:49) |
| Leu37NNY 5' | TTACTTCNNYCCGGAAGGTTCTCGTGTTACCCGT 3' | (SEQ ID NO:50) |
| 5' | GATCACGGGTAACACGAGAACCTTCCGGRNNGAAGTAAACGT 3' | (SEQ ID NO:51) |
| Glu39NNY 5' | TTACTTCCTGCCGNNYGGTTCTCGTGTTACCCGT 3' | (SEQ ID NO:52) |
| 5' | GATCACGGGTAACACGAGAACCRNNCGGCAGGAAGTAAACGT 3' | (SEQ ID NO:53) |
| Gly40NNY 5' | TTACTTCCTGCCGGAANNYTCTCGTGTTACCCGT 3' | (SEQ ID NO:54) |
| 5' | GATCACGGGTAACACGAGARNNTTCCGGCAGGAAGTAAACGT 3' | (SEQ ID NO:55) |
| Leu47NNY 5' | ACCCGTGATNNYCGTTACAACCGTGTTCGC 3' | (SEQ ID NO:56) |
| 5' | GTTGTAACGRNNATCACGGGTAACACGAGA 3' | (SEQ ID NO:57) |
| Tyr49NNY 5' | GATCTGCGTNNYAACCGTGTTCGCGTTTTC 3' | (SEQ ID NO:58) |
| 5' | AACACGGTTRNNACGCAGATCACGGGTCAA 3' | (SEQ ID NO:59) |
| Asn50NNY 5' | CTGCGTTACNNYCGTGTTCGCGTTTTCTAC 3' | (SEQ ID NO:60) |
| 5' | GCGAACACGRNNGTAACGCAGATCACGGGT 3' | (SEQ ID NO:61) |

3. Rapid screening of libraries. Libraries were introduced into E. coli BL21 (DE3) cells and individual, cloned transformants were grown by shaking at 37° C. in 200 µl LB containing 30 µM kanamycin in 96-well, 0.45 µm GHP membrane filter plates (Gelman) (FIG. 2). When O.D. 600 values reached 0.4, 60 µl of culture were transferred to secondary 96-well plates (Falcon), adjusted to 10% glycerol, and stored at −80° C. These frozen stocks served as master copies of the libraries. IPTG was added to the cultures to a final concentration of 1 mM, and the cultures were allowed to express eglin c variants for one hour in the filter plate. Expressed eglin c variants were extracted from the cells with 50 mM Tris-HCl pH 8.0 containing 2 mM EDTA following freezing and thawing. These extracts were collected as filtrates by centrifugation of the filter plate above a second plate. The filtrates, representing partially purified eglin c variants, were analyzed using a rapid fluorescence-based assay for processing enzyme inhibition as described below in Section 5. Variants exhibiting inhibition greater than the template, R4R1-eglin or R4K1-eglin, were sequenced from the frozen stock as follows. Frozen cells were cultured in 50 to 100 ml culture volumes, and DNA maxipreps were performed; the DNA preparations were then sequenced by automated DNA sequencing. Selected variants were expressed and purified on a larger scale, and affinities for furin or Kex2 were examined quantitatively (see below).

4. Quality control experiments. To set up rapid screening in the 96-well format, well-dependent fluctuation of protein production was tested by expressing R4R1-eglin in the 96-well format. Randomly selected wells were analyzed by SDS-PAGE. Fluctuation of protein yield was within ±10%. The possibility of cross-contamination between wells was tested by filling alternate wells of a 96-well filter plate with solutions containing either the fluorescent compound 7-aminomethylcoumarin (AMC) or Tris-HCl buffer, shaking the plates to simulate growth conditions, and then centrifuging the plates to collect filtrates. No cross-contamination of neighboring wells was found under the conditions used for protein expression and extraction.

5. Rapid protease inhibition assay. Novel eglin variants were diluted 50-fold and incubated with secreted, soluble furin (0.5 nM) for 15 min in 96-well plates. The furin substrate (Boc-Arg-Val-Arg-Arg-MCA) was added, and release of AMC was monitored continuously in a 96-well fluorescence plate reader for 20 min, as described under Example 1. Concentrations of enzyme and substrate were chosen so that under the reaction conditions, the amount of control eglin c protein expressed by the control template would exhibit approximately 60% inhibition of furin. When the data were plotted as % inhibition, comparison to this control value permitted identification of eglin c variant inhibitors exhibiting higher affinity than the control eglin c template. The plasmid DNA encoding such eglin c variant inhibitors were isolated and sequenced.

Similarly, inhibition of Kex2 ($0.8 \times 10^{-10}$ M) was assayed by incubating the enzyme with the 50-fold diluted eglin c variants, and monitoring the release of AMC from Boc-Arg-Val-Arg-Arg-MCA). For PC7 ($1.2 \times 10^{-9}$ M), inhibition of the enzyme by the diluted eglin c variants was monitored by utilizing as substrate Pyr-Glu-Arg-Thr-Lys-Arg-MCA. Active concentrations of these enzymes were determined by active site titration as described previously (Komiyama and Fuller (2000).

The positions and identities of 19 substitutions found at the eight targeted positions are shown in Table 7. These novel variants were expressed and purified, and affinities for both Kex2 and furin were examined. At five targeted positions, novel eglin c variants exhibited no significant enhancement of affinity for either Kex2 or furin. However, as described below, substantial enhancement of affinity at two targeted positions was found. Substitutions for Glu39 exhibited enhanced affinity for furin, but they behaved as temporary inhibitors for these two enzymes.

TABLE 7

| Identified residues. | |
|---|---|
| R4R1-Template | R4K1-Template |
| Tyr35 Ile | Asp33 Gly, Ile, Val |
| Glu39 Gly, Ser, Cys, His, Pro, Tyr | Leu37 Gly |
| Gly40 Ala, Pro, Arg | Asn50 Asp |
| Leu47 Val | |
| Tyr49 Ala, Asp, Cys | |

6. Identification of novel sites that affect enzyme-inhibitor interactions in the initial survey. Tyr49 emerged as an effective site for optimization of affinity (Table 8, see also below under "Full randomization of position 49"). Novel eglin c variants at this position are referred to by the naturally occurring amino acid and the site which it occupies, followed by the non-naturally occurring amino acid which replaced it; the template from which the novel eglin c is derived is indicated following a hyphen. Tyr49Asp-R4R1-eglin, isolated in the initial survey of potential adventitious contact sites, exhibited a 10-fold enhanced affinity for furin and a 16-fold enhanced affinity for Kex2. Position 49 corresponds to P4', a residue which has not been examined previously in studies of the specificity of either Kex2/furin processing proteases or degradative subtilisins. Ala and Cys substitutions for Tyr49 were also found using the rapid furin inhibition assay. The Ala substitution did not affect Kex2 affinity, but did increase furin affinity approximately 2-fold. The Cys variant appears to exhibit higher affinity for both enzymes, but accurate determination of affinities was difficult because the inhibitor purified as a monomer/dimer mixture. Substitution of Gly for Leu37 resulted in a minor effect on affinities for both Kex2 and furin. Affinity data obtained with these novel variants are summarized in Table 8.

TABLE 8

| Improved affinity by Tyr49Asp substitution on the R4R1-template. | | | | |
|---|---|---|---|---|
| | Kex2 | | furin | |
| | $K_i$ | $K_i$ ratio | $K_i$ | $K_i$ ratio |
| R4R1- | $9.1 \times 10^{-10}$ | 1 | $2.5 \times 10^{-9}$ | 1 |
| Tyr49Ala-R4R1- | $1.0 \times 10^{-9}$ | 1.1 | $1.3 \times 10^{-9}$ | 1/1.9 |
| Tyr49Asp-R4R1- | $4.5 \times 10^{-11}$ | 1/20 | $3.3 \times 10^{-10}$ | 1/7.6 |
| R4K1- | $2.5 \times 10^{-9}$ | 1 | $3.8 \times 10^{-8}$ | 1 |
| Asp33Val-R4K1- | $1.2 \times 10^{-9}$ | 1/2.1 | $1.7 \times 10^{-8}$ | 1/2.2 |
| Leu37Gly-R4K1- | $1.6 \times 10^{-9}$ | 1/1.6 | $2.9 \times 10^{-8}$ | 1/1.3 |

7. Full randomization at position 49. Following the discovery of the importance of position 49, a library was constructed in which this codon was fully randomized using the following pair of oligonucleotides:

5' CTGCGTNNNAACCGTGTACGCGTTTTC 3'  (SEQ ID NO:62)

5' CGCGTACACGGTTNNNACGCAGATCAC 3'  (SEQ ID NO:63)

Figure 3A:
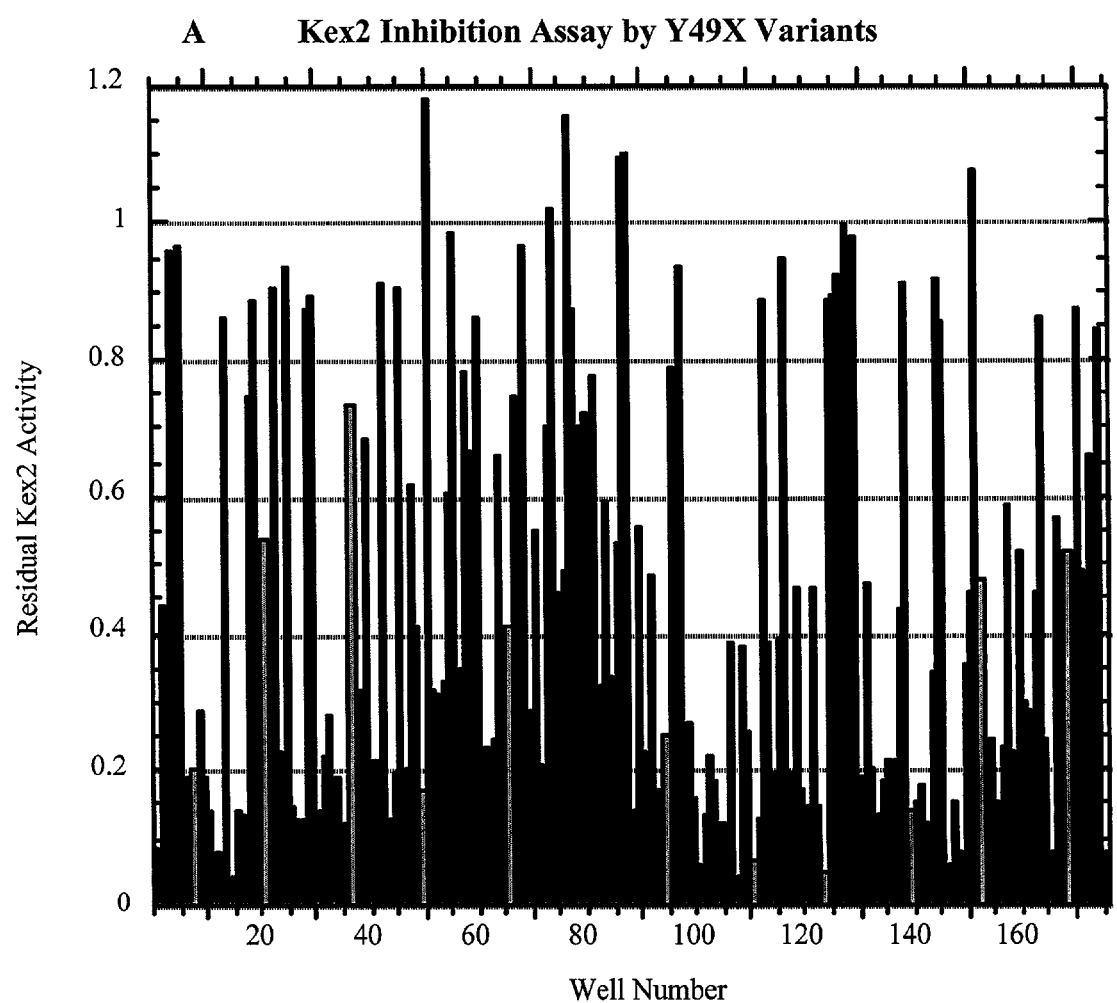
Figure 3B:
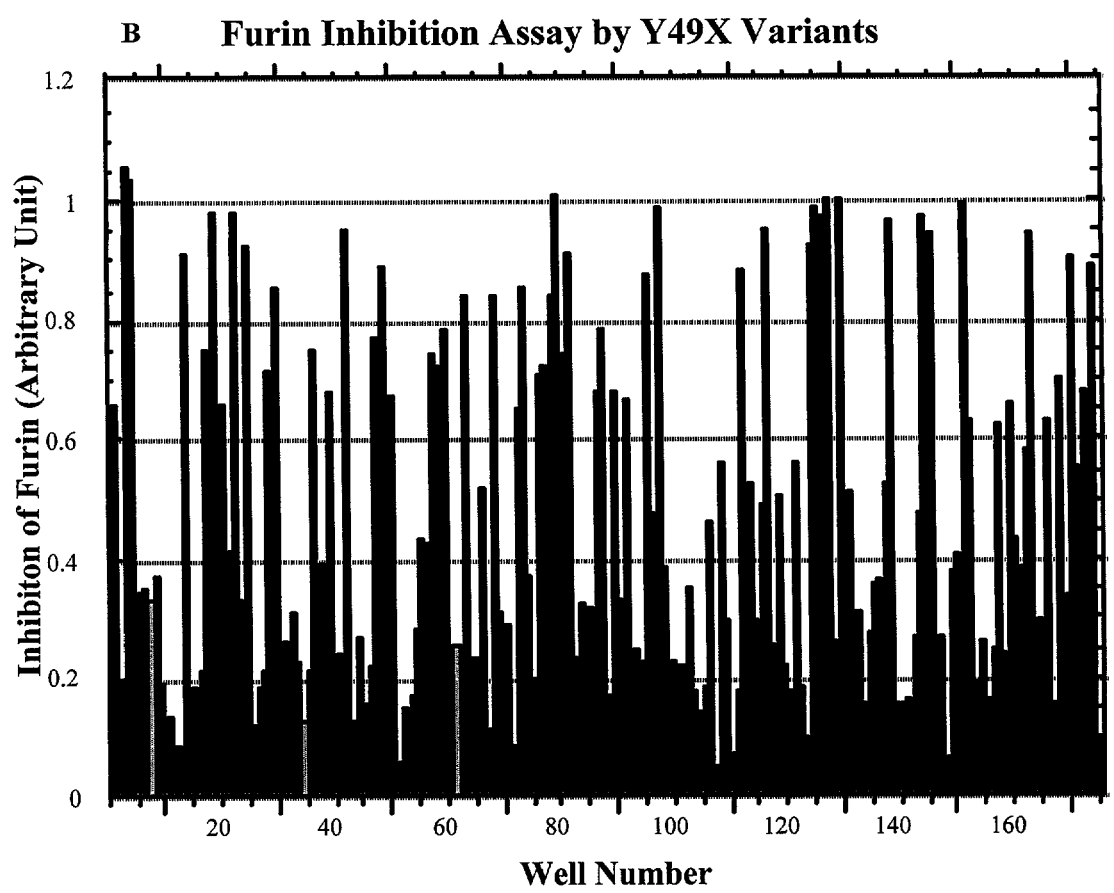
Figure 3C:
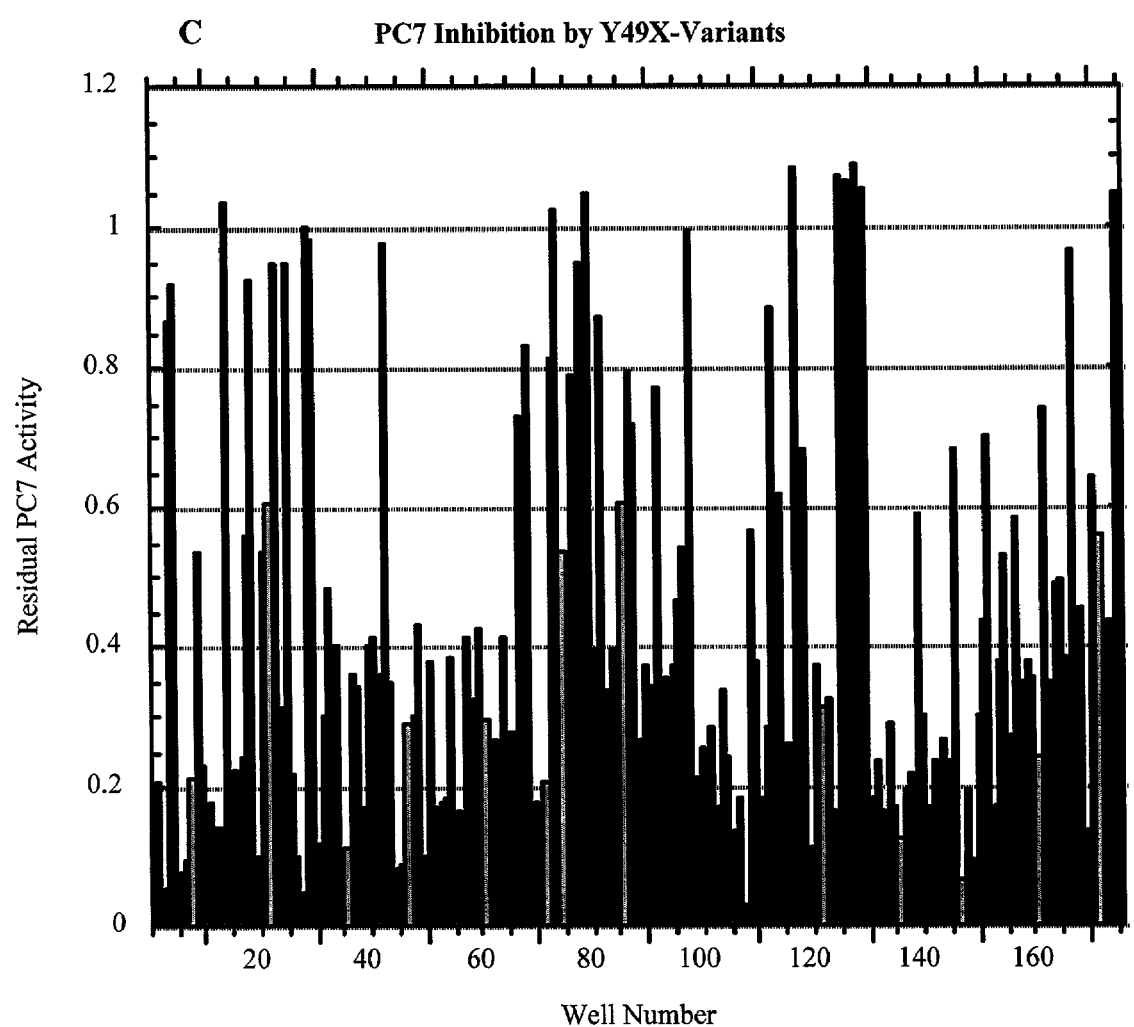

Eglin variants were expressed as described above. Results from rapid screening of the library using Kex2, furin, and human PC7, another mammalian furin homologue (Meerabux, J. et al. (1996) Cancer Research 56: 448–451; and Siedah et al. (1996)) are shown in FIG. 3. The inhibition of the enzymes was assayed as described. Under the conditions used in these assays, the R4R1-eglin template exhibited 60% inhibition of Kex2 and furin, and 70% inhibition of PC7. Substrates for Kex2 and PC7, respectively, were Boc-Arg-Val-Arg-Arg-MCA (SEQ ID NO:69) and pyroGlu-Arg-Thr-LysArg-MCA (SEQ ID NO:70). More than 36% of the novel eglin c variants were better inhibitors of tested enzymes than the template from which they were derived, although 10% of the novel eglin c variant proteins were not inhibitors of these particular enzymes tested.

The inhibition pattern of Kex2, furin, and PC7 by the randomized Tyr49 eglin variants were distinct from each other, as shown in FIG. 3, indicating that the method of the present invention can be used to identify specific inhibitors for each member of the processing proteases. This figure shows the response of three enzymes, Kex2, furin and PC7 (a mammalian furin), to a set of eglin variants (more than 180) based on R4R1-eglin with random substitutions at codon 49. Note that the numbers on the x axis refer to individual inhibitors which are the same in each graph. The results shown in FIG. 3 show that for each enzyme there are inhibitors that are more effective against one enzyme than against the other two; such inhibitors are then selective for the enzyme for which they are more effective.

Figure 4A:
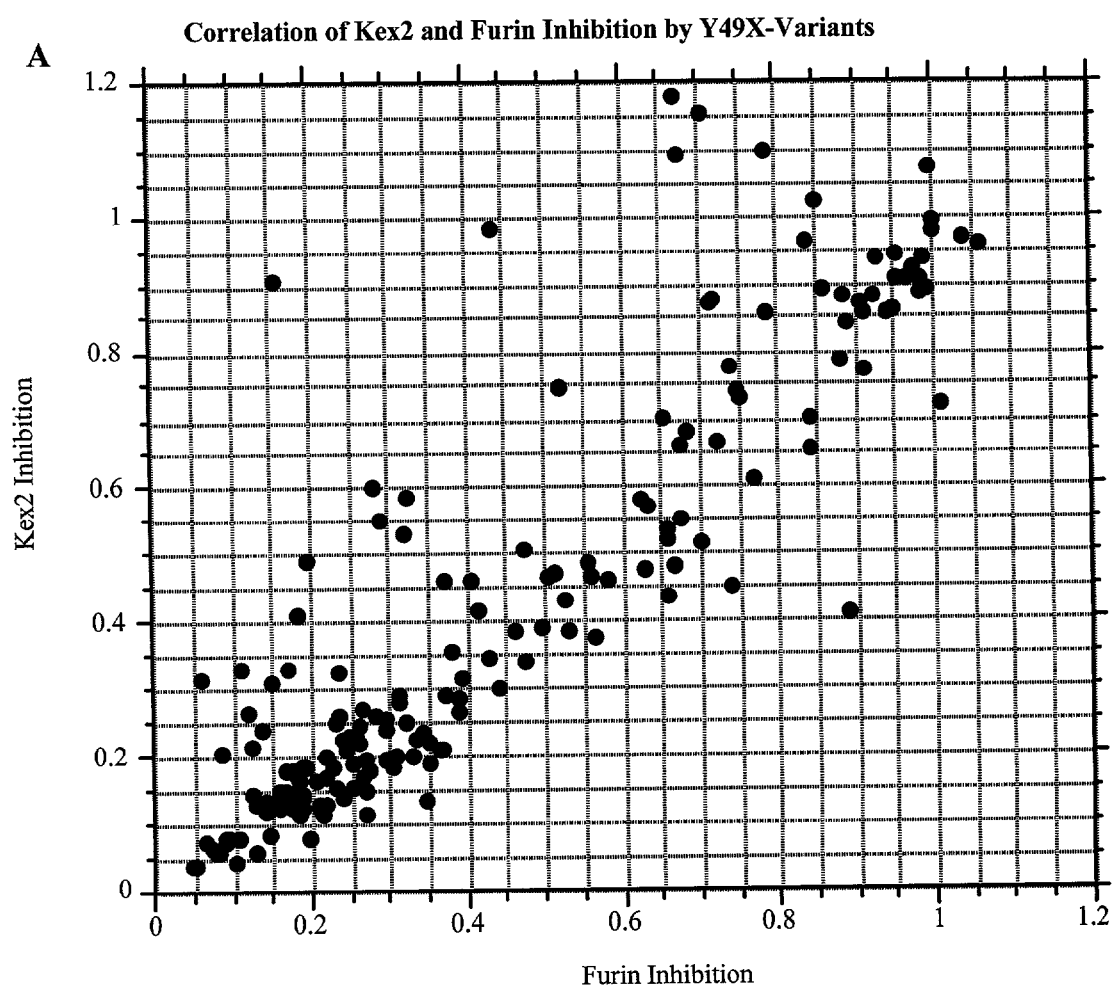
Figure 4B:
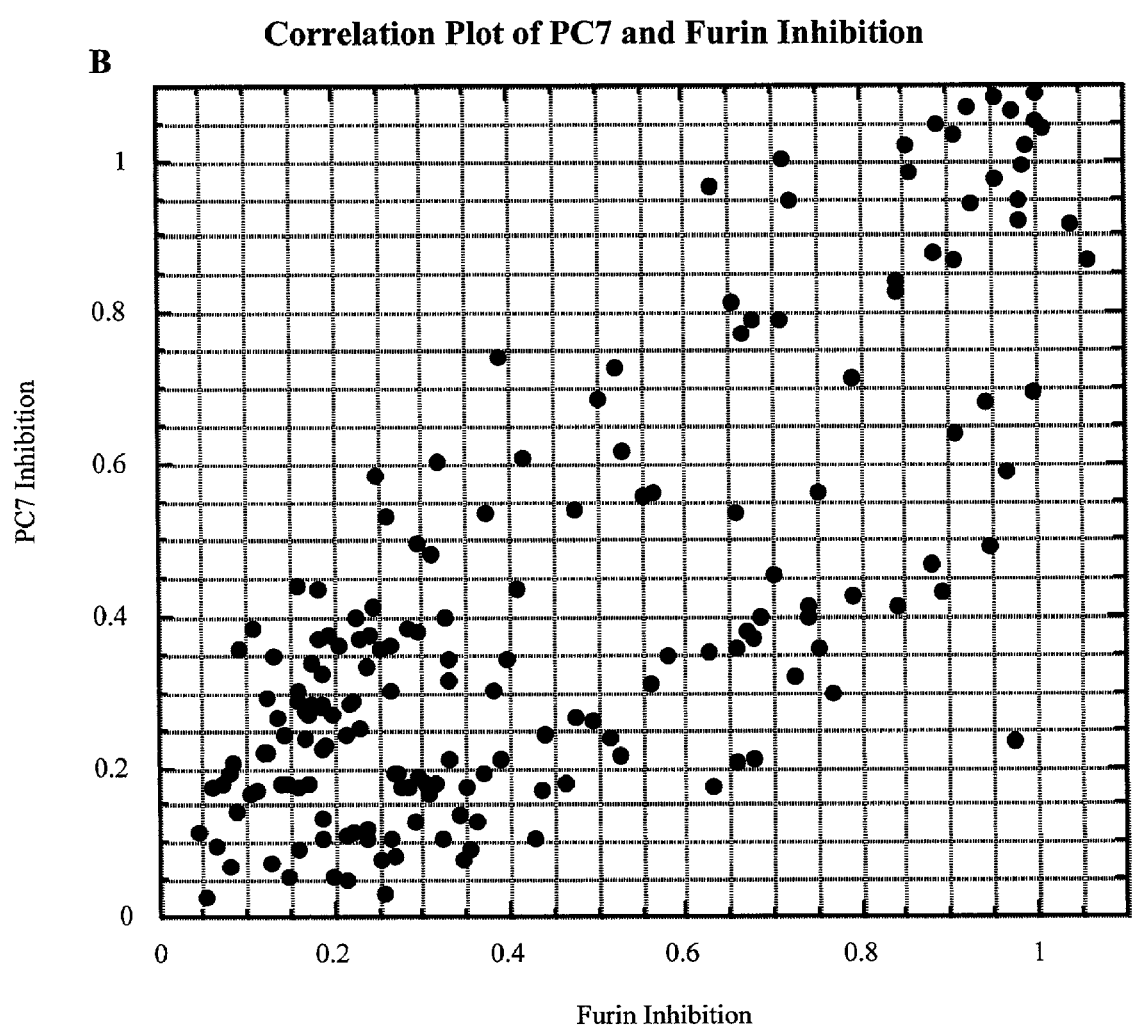

Correlation of inhibition ratios of each enzyme by the randomized Tyr49A-eglin variants are shown in FIG. 4. The most potent inhibitors are not necessarily selective between different members of the Kex2/furin family (for example, between furin and PC7), but potent inhibitors of each of tested enzymes which are also selective can be found. Thus, potent inhibitors of Kex2 also inhibit furin equally well (FIG. 4A). However, two species exhibited an inhibition ratio of ~0.2, or ~0.4 with furin, while exhibiting almost no inhibition of Kex2 (FIG. 4A). Considerably greater divergence was seen when furin inhibition ratios were plotted against PC7 inhibition ratios (FIG. 4B), suggesting that inhibitors that discriminate between PC7 and furin can be distinguished, and that PC7 has a rather unique specificity for the side chain position 49 in R4R1-eglin.

Several data points in FIG. 4 indicate the existence of inhibitors which exhibited a unique inhibition ratio to each member of the enzyme family that was tested. This is additional evidence that selective inhibitors can be obtained by this screening method. Thus, the method of the present invention, of randomization of adventitious contacts, can be used to find both potent, or specific, and selective, inhibitors of individual members of a protease enzyme family.

8. Sequence determination of novel Tyr49Xaa eglin c variants exhibiting potent inhibition of Kex2, furin and/or PC7. Table 9 shows newly found residues in position Tyr49 that yield potent inhibitors of the tested enzymes in R4R1-eglin. Kex2 and furin exhibited overlapping selectivity for certain variants, but PC7 selects a distinct set of Tyr49 substitutions. Table 10 shows the data for the affinities of variants at position 49 in the context of R4R1-eglin. These results indicate that substitution of Asp or Glu at for Tyr at position 49 favor interaction of the resulting eglin variant with furin and Kex2, while substitution of Trp for Tyr at position 49 favors interaction of the resulting eglin variant with PC7. Thus, various substitutions at one position can yield both increased affinity and selectivity of a particular eglin variant.

TABLE 9

Tyr49 substitution of potent inhibitors of Kex2, furin and PC7, which were obtained from rapid inhibition assay. Cys+ includes unexpected, spontaneous substitution at Pro38Leu in the R4R1-template besides of Tyr49Cys.

| Kex2 | Val, Asp, Glu, Cys, |
| Furin | Gly, Ser, Asp, Glu, Cys, Cys+ |
| PC7 | Ala, Val, Met, Trp, Cys+ |

TABLE 10

Effect of Tyr49 substitution in R4R1-eglin on inhibition constants ($K_i$ (M)) determined by purified eglin variants, for Kex2, furin, and PC7. Experimental errors of $K_i$ determinations were ± 20%. The variant is indicated by the amino residue present at position 49.

|  | Kex2 | furin | PC7 |
|---|---|---|---|
| Tyr49-R4R1- | $9.1 \times 10^{-10}$ | $2.5 \times 10^{-9}$ | $1.3 \times 10^{-9}$ |
| Ala49-R4R1- | $1.0 \times 10^{-9}$ | $1.8 \times 10^{-9}$ | $2.9 \times 10^{-9}$ |
| Asp49-R4R1- | $5.6 \times 10^{-11}$ | $3.0 \times 10^{-10}$ | $1.8 \times 10^{-9}$ |
| Glu49-R4R1- | $3.6 \times 10^{-11}$ | $5.3 \times 10^{-10}$ | $2.9 \times 10^{-9}$ |
| Ser49-R4R1- | $2.1 \times 10^{-10}$ | $4.8 \times 10^{-9}$ | $2.5 \times 10^{-9}$ |
| Trp49-R4R1- | $1.2 \times 10^{-9}$ | $1.0 \times 10^{-8}$ | $4.7 \times 10^{-10}$ |
| Met49-R4R1- | $1.0 \times 10^{-9}$ | $1.6 \times 10^{-9}$ | $1.4 \times 10^{-9}$ |

9. Effect of full versus limited randomization on number of effective eglin variants. Full randomization at Tyr49 generated many more potent inhibitors than limited randomization. To test whether limited randomization might have resulted in missing important variants at other positions, two remaining "adventitious contacts sites," His65 and His68, were fully randomized by using oligonucleotide pairs shown in Table 11. To detect marginal enhancement of affinity, R4K1-eglin was used as a template for mutagenesis. This mutant was used because the Lys at P1 in R4K1 eglin results in lower affinity, and therefore provides more latitude in discovering novel variants with higher affinity. If the starting inhibitor has a very high affinity, then only tiny concentrations can be used, and fluctuations in the concentration of the cell extract can have a huge effect on inhibition levels. Thus, the level of inhibitor and substrate are set at a point at which only partial inhibition is observed, such that both increases and decreases in inhibitor affinity can be detected. The results show that His65Cys and His68Arg substitutions yielded minor enhancements of affinity. This established that Tyr49 is identified as an important residue for both specificity and affinity, and that use of the limited randomization approach did not result in missing important sites. Thus, it is anticipated that in the process of optimizing affinity between any given set of protein ligands, limited randomization of potential adventitious contact sites will lead to identification of the important contacts which can then be optimized by full randomization.

TABLE 11

Oligonucleotide pairs used for randomization of
His65 and His68 on the R4K1 -template.

| | | |
|---|---|---|
| His65NNN | 5' GTTAACNNNGTTCCGCATGTTGGCTAAC 3' | (SEQ ID NO:64) |
| | 5' CCAACATGCGGAACNNNGTTAACAAC 3' | (SEQ ID NO:65) |
| His68NNN | 5' CATGTTCCGNNNGTTGGTTAACGGA 3' | (SEQ ID NO:66) |
| | 5' CGTTAACCAACNNNCGGAACATGGT 3' | (SEQ ID NO:67) |

"NN" refers to a fully randomized codon where N = any nucleotide.

Based upon results from the above and similar experiments, it is contemplated that the following substitutions at His65 and His68 will further improved eglin affinity for furin:

the substitution of Ile for Leu47 in the context of R4R1-eglin;

the substitution of Cys for His65 in the context of R4R1-eglin;

the substitution of Arg for His68 in the context of R4R1-eglin.

10. Double adventitious contact site mutant eglin-c variants. Data obtained from inhibition studies of Asp49Val33-R4R1-eglin-c variants demonstrate that amino acid substitution at Val33 increases the selectivity of Asp49-R4R1-eglin-c, by decreasing inhibition of another processing enzyme, PC7, without affecting inhibition of furin, as shown in Table 12. As described above, the methods used to generate and evaluate mutations at adventitious contact sites have the potential to create inhibitors with both higher affinity and higher selectivity. In these experiments, the Tyr49Asp mutation introduced into R4R1-eglin significantly increases affinity for human furin (and for the yeast homologue Kex2) and slightly decreases affinity for another human homologue, PC7. Addition of the Asp33Val substitution further decreases affinity for PC7 without affecting affinity for furin (or Kex2). Thus the quadruple mutant, V33D49-R4R1-eglin (where the designation refers to the substituted amino acid at the position indicated), exhibits both high affinity for furin ($K_i$=2.7×10[10] M) and high selectivity for furin (42-fold preference for furin over PC7).

TABLE 12

Effect of Tyr49 and Val33 substitution in R4R1-eglin on inhibition constants ($K_i$ (M)) determined by purified variants, for Kex2, furin, and PC7

| R4R1-variants | Kex2* | furin* | PC7* |
|---|---|---|---|
| D33Y49 | $1.1 \times 10^9$ | $4.0 \times 10^8$ | $7.7 \times 10^8$ |
| | ⇓ | ⇓ | ↑ |
| D33D49 | $1.8 \times 10^{10}$ | $3.0 \times 10^9$ | $5.6 \times 10^8$ |
| | ↓ | ↓ | ⇑ |
| V33D49 | $2.4 \times 10^{10}$ | $3.7 \times 10^9$ | $8.7 \times 10^7$ |

*$K_{assoc}$ (equilibrium association constants in $M^{-1}$).

Example 3

Inhibition of Cellular Processing of Pro-Von Willebrand Factor by Asp49-R4R1-Eglin The potency of Asp49-R4R1-eglin to inhibit intracellular furin activity when present in cell culture media was tested by examining furin dependent processing of von Willebrand factor (vWF) in COS-1 cells (Wise, R. J. et al. (1990) Proc. Natl. Acad. Sci. USA 87, 9378–9382). Pro-vWF is believed to be a physiological substrate of furin, where the site of cleavage is shown in FIG. 6, panel A.

Methods

SV40-driven vectors, pMT2-vWF (Wise, R. J. et al. (1990) Proc. Natl. Acad. Sci. USA 87, 9378–9382) and pSRfurin (Bravo, D. A., et al. (1994) J. Biol. Chem. 269, 25830–25837) were co-transfected into COS-1 cells following previously described methods (Dorner, A. J. & R. J. Kaufman (1990) in Methods in Enzymology 185 (Academic Press: San Diego) pp. 577–596). To monitor the effect of Asp49-R4R1-eglin on furin dependent pro-vWF processing, either Asp49-R4R1-eglin or wild type-eglin (Leu 45) (5 μM) was added to the media of COS-1 cell plates 4 hours prior to a pulse radio-label with [$^{35}$S]-Met/Cys mixtures (200 μCi) for 30 minutes. Following this pulse, a chase with excess unlabeled Met/Cys was performed for 5.5 hours. Cells were lysed with NP-40 lysis buffer and were blocked with 25 μl protein A Sepharose (Ammersham-Pharmacia) for 2 hours. Blocked extracts were incubated with 1 μl anti-vWF polyclonal antibody (Dako, Denmark) overnight and immunoprecipitated with 50 μl of protein A Sepharose for 2 hours. All immunoprecipitation processes were performed at 4° C. The protein conjugates were boiled for 5 minutes in SDS-loading buffer containing 50 mM DTT, and analyzed by SDS-PAGE. Gels were enhanced with ENHANCE® (NEN), dried, and autoradiographed.

Results

Furin and vWF were co-expressed in COS-1 cells, and radio labeled with [$^{35}$S]-Met/Cys as described in Methods (above). Processing of pro-vWF by furin was examined by adding Asp49-R4R1-eglin (5 μM) into the conditioned media. Either Asp49-R4R1-eglin or wild type eglin (Leu45) were added to the medium 4 hours prior to a pulse radio-label for 30 minutes, and cell lysates analyzed after a 6 hour chase by SDS-PAGE, as shown in FIG. 6, panel B. To precisely identify mature-vWF band on the gel, COS-cells was transfected with a Δ-pro-vWF construct (pMT2-del-provWF; Rehemtulla, A. and R. J. Kaufman (1992) Blood 79:2349–2355) which lacks the prodomain from the prepro-vWF construct, as shown in FIG. 6, panel A; the expression of Δ-pro-vWF thus acts as a molecular weight marker for processed or mature vWF. Mature vWF was not observed in the presence of Asp49-R4R1-eglin (FIG. 6, panel B, lane 4), showing that the processing reaction was blocked. The wild type eglin showed no effect on the processing reaction (FIG. 6, panel B, lane 5), as seen by comparison to proteins present in the absence of addition of any eglin-c at all (FIG. 6, panel B, lane 6).

The conditioned medium was also analyzed by gel electrophoresis, and the same results were observed, in that the addition of Asp49-R4R1-eglin, but not wild-type eglin, inhibited the appearance of mature vWF in the medium. The conditioned medium includes what was secreted by the cells during the experiment, where the conditions are those described for FIG. 6. These results from the conditioned medium indicate that not only do cells process the expressed pro-vWF, but also that the processed or mature vWF is biologically active, as indicated by its secretion from the cells into the medium. Moreover, the addition of Asp49-R4R1-eglin inhibits both the processing of the pro-vWF and its subsequent secretion by the cells. Thus, Asp49-R4R1-eglin is an effective inhibitor of furin in vivo, and of the activation of a proprotein into its mature form.

Example 4

Inhibition of Processing of Anthrax Protective Antigen by Purified Eglin-c Variants This experiment describes the inhibition by purified eglin c variants of the processing of anthrax protective antigen in experimental toxicity assays.

Entry of anthrax lethal factor and edema factor into target cells requires the action of anthrax protective antigen for selective translocation (Young, J A, and Collier, R J (2002) Scientific American. 286(3):48–50, 54–9). Anthrax protective antigen binds to a receptor on the animal cell surface where it is cleaved by furin (Young, J A, and Collier, R J (2002) Scientific American 286(3):48–50, 54–9; Bradley, K A et al. (2001) Nature. 414:225–9). Cleavage by furin is required both for oligomerization of the protective antigen and its endocytosis (Beauregard, K E et al. (2000) Cellular Microbiology. 2:251–8; and Sellman, B R et al. (2001) Science. 292:695–7). Once internalized, oligomeric protective antigen can translocate lethal and edema factors in response to acidification of the endocytic vesicle by vacuolar proton translocating ATPase (Young, J A, and Collier, R J (2002) Scientific American. 286(3):48–50, 54–9). Inhibition of the cleavage of anthrax toxin protective antigen will therefore abrogate toxicity of anthrax toxin, the principal pathogenic mechanism of *Bacillus anthracis*.

It is contemplated that the administration of eglin-c variants will inhibit cleavage of anthrax toxin. Because processing of anthrax protective antigen occurs at the cell surface, it is not necessary for the eglin-c variant protein to penetrate the cell; therefore, it is contemplated that inhibition of cell surface furin will be sufficient to block processing of anthrax protective antigen. As a result, it is also contemplated that much lower concentrations of eglin-c variant protein will be sufficient to inhibit processing of anthrax protective antigen, when compared to the amounts utilized to observe inhibition of pro-vWF processing, which occured internally within the cells.

*Bacillus anthracis* (Anthrax) protective antigen and lethal factor (provided as purified proteins by Joel Swanson and John Collier), when added to primary rat macrophages (provided by Joel Swanson), kill macrophages within 24 hours, as shown by propidium iodide permeability. Either Asp49-R4R1-eglin or L1-eglin (wild-type eglin) was added at 1 mM and preincubated with macrophages (grown on microscope cover slips) for 2 hours prior to addition of lethal factor and protective antigen. After addition of lethal factor and protective antigen, cells were incubated for an additional 24 hours at 37° C. Cells were then fixed and stained with propidium iodide. Cell death was scored by propidium iodide staining as determined by fluorescence microscopy. It is contemplated that the addition of Asp49-R4R1-eglin, but not L1-eglin, prevents or slows macrophage death. It is also contemplated that the addition of Asp49-R4R1-eglin, but not L1-eglin, prevents or inhibits the processing of anthrax protective antigen, as determined by analysis of proteins by SDS-PAGE, and detecting the presence of processed and unprocessed anthrax protective factor by antibody binding. It is further contemplated that the addition of Asp49-R4R1-eglin, but not L1-eglin, prevents or inhibits the entry of lethal factor into the macrophages.

Example 5

Use of Eglin Variants in Affinity Purification of Processing Proteases

M4R1-eglin and R4R1-eglin were used to synthesize affinity resins and these were tested for furin purification. Resins containing both M4R1-eglin and R4R1-eglin can be used to bind furin from crude samples.

Resins were synthesized by immobilizing purified M4R1-eglin and R4R1-eglin onto Reacti-Gel 6X (Pierce) using the manufacturer's protocol.

The resins were then used to test binding and elution of furin from these resins. Furin (250 µl of dialyzed conditioned medium, 3,460 units/ml) was bound quantitatively to 500 µl of M4R1-eglin Resin in 10 mM Tris-HCl (pH 8.0). Enzyme was eluted with 20 mM NaMES (pH 6.0) with approximately 90% yield. Furin binding capacity to the R4R1-eglin Resin was 10-fold higher relative to the M4R1-eglin Resin, but furin was not eluted by dropping pH. Instead, furin bound to the R4R1-eglin column was eluted with buffer containing 2 mM EDTA. 5 mM $CaCl_2$ was added to restore activity and 85% of the furin activity was recovered. (Unit definition: Release of 1 pmol of AMC/min in a reaction containing 100 mM Boc-Arg-Val-Arg-Arg-MCA, 1 mM $CaCl_2$ and 20 mM NaMES (pH 7.0) at 37° C.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A composition comprising a protease inhibitor that is an eglin c variant, wherein the eglin c variant comprises SEQ ID NO.2 with the exception of an amino acid change at a position selected from the group consisting of Asp33, Tyr35, Leu37, Glu39, Gly40, Leu47, Tyr49, Asn50, His65 and His68.

2. The composition of claim 1, said amino acid change is Tyr49Asp.

3. The composition of claim 1, wherein said amino acid change is Asp33Val.

4. A composition comprising a protease inhibitor that is an eglin c variant, wherein the eglin c variant comprises at least one at least one amino acid change at a position selected from the group consisting of Asp33, Tyr35, Leu37, Glu39, Gly40, Leu47, Tyr49, Asn50, His65 and His68 of SEQ ID NO:2, and further comprising at least one amino acid change at a position selected from the group consisting of Gly40, Ser41, Pro42, Val43, Thr44 and Arg45 of SEQ ID NO:2.

5. The composition of claim 4, wherein said amino acid change is selected from the group consisting of Pro42Arg and Arg45Lys.

6. A composition comprising a protease inhibitor that is an eglin c variant, wherein the eglin c variant is selected from the group consisting of eglin c variants R4-, M4R1-, R4R1-, M4K1-, R4K1-, R6R4F1-, K2R1-, M4K2R1-, R4,K2R1-eglin, wherein the variant further comprises at least one amino acid chance at a position selected from the group consisting of Asp33, Tyr35, Leu37, Glu39, Gly40, Leu47, Tyr49, Asn50, His65 and His68 of SEQ ID NO:2.

7. The composition of claim 6, wherein the eglin c variant inhibitor is selected from the group consisting of R4R1- and R4K1-eglin.

8. The composition of claim 6, wherein the eglin c variant inhibitor is selected from the group consisting of R4R1- and R4K1-eglin.

9. The composition of claim 8, wherein the eglin c variant is selected from the group consisting of R4R1- and R4K1- eglin, and wherein said eglin c variant further comprises an amino acid change selected from the group consisting of Asp replacing Tyr49, Val replacing Asp33, and both Asp replacing Tyr49 and Val replacing Asp33.

10. The composition of claim 9, wherein the eglin c variant is R4R1-eglin, and and wherein said eglin c variant further comprises Asp replacing Tyr49 and Val replacing Asp33.

* * * * *